United States Patent
Tamura et al.

(10) Patent No.: US 6,242,600 B1
(45) Date of Patent: Jun. 5, 2001

(54) 2-PIPERAZINONE-1-ACETIC ACID DERIVATIVES AND THEIR USE

(75) Inventors: Norikazu Tamura, Kobe; Zen-ichi Terashita, Toyonaka, both of (JP)

(73) Assignee: Takeda Chemical Industries, Ltd., Osaka (JP)

( * ) Notice: Subject to any disclaimer, the term of this patent is extended or adjusted under 35 U.S.C. 154(b) by 0 days.

(21) Appl. No.: 09/355,499

(22) PCT Filed: Mar. 5, 1998

(86) PCT No.: PCT/JP98/00907

§ 371 Date: Jul. 28, 1999

§ 102(e) Date: Jul. 28, 1999

(87) PCT Pub. No.: WO98/39324

PCT Pub. Date: Sep. 11, 1998

(30) Foreign Application Priority Data

Mar. 7, 1997 (JP) ................................... 9-053574

(51) Int. Cl.⁷ .................... C07D 413/14; C07D 347/00; C07D 241/04
(52) U.S. Cl. .................... 544/295; 544/298; 544/358; 544/360; 544/382
(58) Field of Search .................... 544/295, 298, 544/358, 360, 382

(56) References Cited

U.S. PATENT DOCUMENTS 5,876,756 * 3/1999 Takada et al. ................. 424/489

FOREIGN PATENT DOCUMENTS

| 0529858 | 3/1993 | (EP) . |
| 0643072 | 3/1995 | (EP) . |
| 0765660 * | 4/1997 | (EP) . |
| WO 96/33982 | 10/1996 | (WO) . |

* cited by examiner

*Primary Examiner*—Richard L. Raymond
*Assistant Examiner*—Sudhaker B Patel
(74) *Attorney, Agent, or Firm*—Philippe Y. Riesen; Mark Chao

(57) ABSTRACT

The present invention provides compounds and medicines effective for prophylaxis and therapy of various diseases by controlling or inhibiting cell-adhesion. Especially, the compounds of this invention inhibit platelet aggregation action without remarkable elongation of hemorrhagic period and can be used as a safe and long-acting antithrombotic drug as compared with known substances showing the same activity.

Compounds of this invention are piperazinones of the formula:

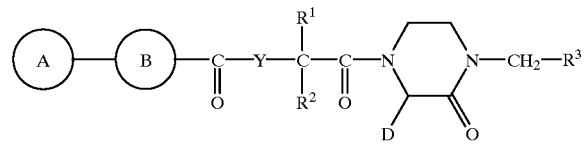

wherein the ring A is a basic heterocyclic group; the ring B is a nitrogen containing heterocyclic group or a cyclic hydrocarbon group; Y is $CH_2$; $R^1$ is H, OH, $NH_2$ or an hydrocarbon group which may be bound through CO, S, SO or $SO_2$; $R^2$ is H or a hydrocarbon group; $R^3$ is an optionally esterified or amidated carboxyl group; and D is a lower alkyl group substituted with an optionally esterified carboxyl group; or a salt thereof.

38 Claims, No Drawings

2-PIPERAZINONE-1-ACETIC ACID DERIVATIVES AND THEIR USE

This application is the National Stage of International Patent application PCT/JP98/00688, filed Feb. 19, 1998.

TECHNICAL FIELD

This invention relates to novel 2-piperazinone-1-acetic acid derivatives which are useful for a medicine, or a salt thereof and to a pharmaceutical composition for inhibiting cell-adhesion comprising these derivatives as effective components.

BACKGROUND ART

As the factors participating in adhesion to the extracellular substrate of animal cells, there have been known fibronectin, vitronectin, osteopontin, collagen, thrombospondin, fibrinogen, von willebrand factor, etc. These proteins include tripeptide sequence of -Arg-Gly-Asp- as cell recognition site. This tripeptide is recognized by at least one protein belonging to the receptors integrins, which are heterodimeric proteins consisting of sub-units combined to two membranes [Science, 238, 491 (1987)].

Structurally related integrin receptors, which recognize the amino acid sequence -Arg-Gly-Asp-, are known to express at the extracellular surface glycoprotein of platelets, endothelial cells, leucocyte, lymphocyte, monocyte and granulocyte. Compounds having the amino acid sequence -Arg-Gly-Asp- are competitively bound to the site to be bound with intracellular adhesive factors to thereby inhibit the binding of intracellular adhesive factors. As such substances for inhibiting intracellular adhesion, there has been known, for example, H-Gly-Arg-Gly-Asp-Ser-Pro-OH.

When blood vessels are injured, platelets are activated with, for example, endothelial collagens, which causes binding of fibrinogen to platelets, i.e. platelet aggregation, to form thrombus. The interaction between platelets and fibrinogen takes place through GP IIb/IIIa, this being an important characteristic feature of platelet aggregation. Cell adhesion-inhibiting substances can inhibit platelet aggregation due to substances causing platelet aggregation such as thrombin, epinephrine, ADP and collagen.

Besides, cell-adhesion inhibiting substances are expected to be useful as drugs for suppression of metastasis of tumor cells (inhibition of fixed adhesion at the site where the tumor cells are migrated).

Linear or cyclic peptides containing the amino acid sequence, -Arg-Gly-Asp- (RGD) have been known as cell-adhesion inhibiting substances [Journal of Biological Chemistry (J. Biol. Chem.), 262, 17294 (1987) and Japanese published unexamined patent application No. 174797/1990, among others].

And, non-peptide compounds having an anti-thrombotic action are disclosed in Japanese published unexamined patent application No. 264068/1992 and EPA 505868. Further, compounds having pyridyl-piperazine or pyridazinyl-piperazine, which have an anti-thrombotic action, are disclosed in WO 96-24581. And, such drugs as aspirin, heparin and ticlopidine are known to show undesirable side effects such as prolongation of bleeding time. As known platelet aggregation inhibiting substances which are slight in the action of prolonging bleeding time, cyclic peptide derivatives are described in the Japanese publication of translations of International patent application No. 509551/1994.

DISCLOSURE OF INVENTION

These known peptide derivatives mentioned above are not satisfactory in the potency of their activity, and their oral absorbability is not satisfactory from the practical viewpoint. Besides, since these peptide derivatives are hydrolyzed with enzymes including aminopeptidase, carboxypeptidase or various types of endopeptidase, e.g. serine protease, their stability in a solution containing these enzymes or in a living body is not satisfactory. Therefore, for clinical application of these peptide derivatives, there are problems still to be solved.

And, in the non-peptide compounds having an anti-thrombotic action, compounds having higher potency and being durable for a longer period as compared with the above-mentioned known compounds having an antithrombotic action have been sought for.

Further, the known platelet aggregation inhibiting substances which are slight in the action of prolonging bleeding time are far from being satisfactory in the durability of the action and oral absorbability. Therefore, such compounds as showing longer durability and capable of being administered orally have been sought for.

The present inventors diligently made extensive studies and, as a result, they succeeded in synthesizing a compound or a salt thereof [hereinafter, referred to as Compound (I)], whose characteristic feature in the chemical structure lies in having a basic heterocyclic group at terminals of substituents at 4-positions of the 2-piperazinone ring, represented by the formula (I)

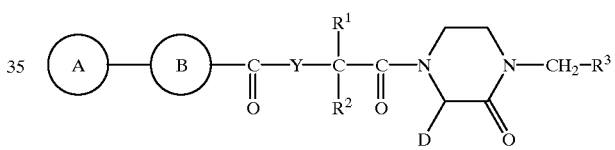

wherein the ring A is a basic 5- to 7-membered heterocyclic group which may be substituted; the ring B is a divalent 5- to 7-membered nitrogen containing heterocyclic group which may be substituted or a divalent 5- to 7-membered cyclic hydrocarbon group which may be substituted; Y is an optionally substituted methylene group; $R^1$ is a hydrogen atom, an optionally substituted hydroxy group, an optionally substituted amino group or an optionally substituted hydrocarbon group which may be bound through a carbonyl group, a thio group, a sulfinyl group or a sulfonyl group; $R^2$ is a hydrogen atom or an optionally substituted hydrocarbon group; $R^3$ is an optionally esterified or amidated carboxyl group; and D is a lower alkyl group substituted with an optionally esterified carboxyl group; a compound or a salt thereof [hereinafter, referred to as Compound (I-1)] represented by the formula (I-1)

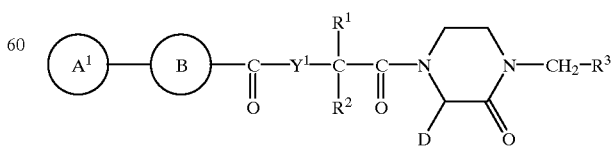

wherein the ring $A^1$ is a basic 5- to 7-membered aromatic heterocyclic group which may be substituted; the ring B is a divalent 5- to 7-membered nitrogen containing heterocyclic group which may be substituted or a divalent 5- to 7-membered cyclic hydrocarbon group which may be substituted; $Y^1$ is an optionally substituted imino group; $R^1$ is a hydrogen atom, an optionally substituted hydroxy group, an optionally substituted amino group or an optionally substituted hydrocarbon group which may be bound through a carbonyl group, a thio group, a sulfinyl group or a sulfonyl group; $R^2$ is a hydrogen atom or an optionally substituted hydrocarbon group; $R^3$ is an optionally esterified or amidated carboxyl group; and D is a lower alkyl group substituted with an optionally esterified carboxyl group; and a compound or a salt thereof [hereinafter, referred to as Compound (I-2)] represented by the formula (I-2)

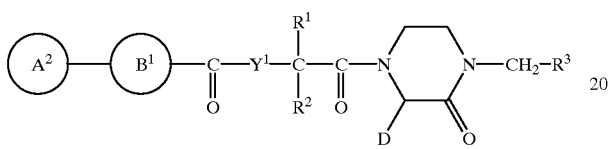

(I-2)

wherein the ring $A^2$ is a piperidyl group which may be substituted; the ring $B^1$ is a phenylene group which may be substituted; $Y^1$ is an optionally substituted imino group; $R^1$ is a hydrogen atom, an optionally substituted hydroxy group, an optionally substituted amino group or an optionally substituted hydrocarbon group which may be bound through a carbonyl group, a thio group, a sulfinyl group or a sulfonyl group; $R^2$ is a hydrogen atom or an optionally substituted hydrocarbon group; $R^3$ is an optionally esterified or amidated carboxyl group; and D is a lower alkyl group substituted with an optionally esterified carboxyl group, and further found that these compounds thus synthesized unexpectedly possess a potent and durable platelet aggregation inhibiting action. Based on this finding, the present invention was accomplished.

More specifically, the present invention relates to (1) the compound (I);
(2) the compound (I-1);
(3) the compound (I-2);
(4) a compound of the above (1), wherein the ring A is a basic 5- to 7-membered heterocyclic group containing, besides carbon atoms, 1 to 3 hetero-atoms selected from oxygen atom, sulfur atom and nitrogen atom, which may have 1 to 5 substituents selected from the class consisting of (1) a $C_{1-6}$ alkyl group, (2) a $C_{2-6}$ alkenyl group, (3) a $C_{2-6}$ alkynyl group, (4) a $C_{3-8}$ cycloalkyl group, (5) a $C_{3-8}$ cycloalkenyl group, (6) a $C_{7-12}$ aralkyl group, (7) a $C_{6-10}$ aryl group, (8) a $C_{1-6}$ alkoxy group, (9) a phenoxy group, (10) a $C_{1-6}$ alkanoyl group, (11) a benzoyl group, (12) a $C_{1-6}$ alkanoyloxy group, a benzoyloxy group, (13) a carboxyl group, (14) a $C_{1-6}$ alkoxy-carbonyl group, (15) a carbamoyl group, (16) a N-mono-$C_{1-6}$ alkyl-carbamoyl group, (17) N,N-di-$C_{1-6}$ alkyl-carbamoyl group, (18) a cyclic amino-carbonyl group, (19) a halogen atom, (20) a halogeno $C_{1-6}$ alkyl group, (21) an oxo group, (22) an amidino group, (23) an imino group, (24) an amino group, (25) a mono-$C_{1-6}$ alkylamino group, (26) a di-$C_{1-6}$ alkylamino group, (27) a 3- to 6-membered cyclic amino group, (28) a $C_{1-6}$ alkanoylamido group, (29) a benzamido group, (30) a carbamoylamino group, (31) a N-mono-$C_{1-6}$-alkyl-carbamoylamino group, (32) a N,N-di-$C_{1-6}$ alkyl-carbamoylamino group, (33) a $C_{1-3}$ alkylenedioxy group, (34) a sulfamoyl group, (35) a $C_{1-6}$ alkylsulfamoyl group, (36) a di-$C_{1-6}$ alkylsulfamoyl group, (37) a $C_{1-6}$ alkylthio group, (38) a $C_{6-10}$ arylthio group, (39) a $C_{1-6}$ alkylsulfinyl group, (40) a $C_{6-10}$ arylsulfinyl group, (41) a $C_{1-6}$ alkylsulfonyl group and (42) a $C_{6-10}$ arylsulfonyl group;

the ring B is (A) a divalent 5- to 7-membered nitrogen containing heterocyclic group which contains, besides carbon atoms, 1 to 3 nitrogen atoms and which may have 1 to 5 substituents selected from the class consisting of (1) a $C_{1-6}$ alkyl group, (2) a $C_{2-6}$ alkenyl group, (3) a $C_{2-6}$ alkynyl group, (4) a $C_{3-8}$ cycloalkyl group, (5) a $C_{3-8}$ cycloalkenyl group, (6) a $C_{7-12}$ aralkyl group, (7) a $C_{6-10}$ aryl group, (8) a $C_{1-6}$ alkoxy group, (9) a phenoxy group, (10) a $C_{1-6}$ alkanoyl group, (11) a benzoyl group, (12) a $C_{1-6}$ alkanoyloxy group, a benzoyloxy group, (13) a carboxyl group, (14) a $C_{1-6}$ alkoxy-carbonyl group, (15) a carbamoyl group, (16) a N-mono-$C_{1-6}$ alkyl-carbamoyl group, (17) a N,N-di-$C_{1-6}$ alkyl-carbamoyl group, (18) a cyclic amino-carbonyl group, (19) a halogen atom, (20) a halogeno $C_{1-6}$ alkyl group, (21) an oxo group, (22) an amidino group, (23) an imino group, (24) an amino group, (25) a mono-$C_{1-6}$ alkylamino group, (26) a di-$C_{1-6}$ alkylamino group, (27) a 3- to 6-membered cyclic amino group, (28) a $C_{1-6}$ alkanoylamido group, (29) a benzamido group, (30) a carbamoylamino group, (31) a N-mono-$C_{1-6}$ alkyl-carbamoylamino group, (32) a N,N-di-$C_{1-6}$ alkyl-carbamoylamino group, (33) a $C_{1-3}$ alkylenedioxy group, (34) a sulfamoyl group, (35) a $C_{1-6}$ alkylsulfamoyl group, (36) a di-$C_{1-6}$ alkylsulfamoyl group, (37) a $C_{1-6}$ alkylthio group, (38) a $C_{6-10}$ arylthio group, (39) a $C_{1-6}$ alkylsulfinyl group, (40) a $C_{6-10}$ arylsulfinyl group, (41) a $C_{1-6}$ alkylsulfonyl group and (42) a $C_{6-10}$ arylsulfonyl group, or (B) a divalent 5- to 7-membered cyclic hydrocarbon group which may have 1 to 5 substituents selected from the class consisting of (1) a $C_{1-6}$ alkyl group, (2) a $C_{3-8}$ cycloalkyl group, (3) a $C_{2-6}$ alkenyl group, (4) a $C_{2-6}$ alkynyl group, (5) a $C_{3-8}$ cycloalkenyl group, (6) a $C_{6-10}$ aryl group, (7) a $C_{7-12}$ aralkyl group, (8) a nitro group, (9) an oxo group, (10) a thioxo group, (11) a cyano group, (12) a carbamoyl group, (13) a carboxyl group, (14) a $C_{1-6}$ alkoxy-carbonyl group, (15) a sulfo group, (16) a halogen atom, (17) a $C_{1-4}$ alkoxy group, (19) a $C_{6-10}$ aryloxy group, (20) a $C_{1-4}$ alkylthio group, (21) a $C_{6-10}$ arylthio group, (22) a $C_{1-6}$ alkylsulfinyl group, (23) a $C_{6-10}$ arylsulfinyl group, (24) a $C_{1-6}$ alkylsulfonyl group, (25) a $C_{6-10}$ arylsulfonyl group, (26) an amino group, (27) a $C_{1-6}$ alkanoylamino group, benzoylamino, (28) a mono- or di-$C_{1-6}$ alkylamino group, (29) a $C_{3-8}$ cycloalkylamino group, (30) a $C_{6-10}$ arylamino group, (31) a $C_{1-6}$ acyl group, (32) a $C_{6-10}$ aryl-carbonyl group and (33) 5- to 6-membered heterocyclic groups containing, besides carbon atoms, 1 to 3 hetero-atoms selected from oxygen atom, sulfur atom and nitrogen atom;

Y is a methylene group which may have 1 or 2 substituents selected from the class consisting of (1) a halogen atom, (2) a hydroxy group, (3) an oxo group, (4) a $C_{1-6}$ alkoxy group, (5) a di-$C_{1-6}$ alkylamino group, (6) a $C_{1-6}$ alkyl group substituted with 1 to 3 halogen atoms, (7) a $C_{1-6}$ acyl group, (8) a hydroxy-$C_{1-6}$ alkyl group, (9) a $C_{1-6}$ alkoxy-$C_{1-6}$ alkyl group and (10) a $C_{1-6}$ alkoxy-carbonyl group;

$R^1$ is (A) a hydrogen atom, (B) a hydroxy group optionally substituted by
  (1) a $C_{1-6}$ alkyl group which may have 1 to 4 substituents selected from the class consisting of a halogen atom, a $C_{6-10}$ aryl group, a $C_{7-12}$ aralkyl group and a nitro group,
(2) a $C_{6-10}$ aryl group which may have 1 to 4 substituents selected from the class consisting of a halogen atom, a $C_{1-6}$ alkyl group, a $C_{6-10}$ aryl group, a $C_{7-12}$ aralkyl group and a nitro group,
(3) a $C_{7-12}$ aralkyl group which may have 1 to 4 substituents selected from the class consisting of a halogen atom, a $C_{1-6}$ alkyl group, a $C_{6-10}$ aryl group, a $C_{7-12}$ aralkyl group and a nitro group,
(4) a formyl group,
(5) a $C_{1-6}$ alkyl-carbonyl group which may have 1 to 4 substituents selected from the class consisting of a halogen atom, a $C_{1-6}$ alkyl group, a $C_{6-10}$ aryl group, a $C_{7-12}$ aralkyl group and a nitro group,
(6) a $C_{6-10}$ aryloxy-carbonyl group which may have 1 to 4 substituents selected from the class consisting of a halogen atom, a $C_{1-6}$ alkyl group, a $C_{6-10}$ aryl group, a $C_{7-12}$ aralkyl group and a nitro group,
(7) a $C_{6-10}$ aryl-carbonyl group which may have 1 to 4 substituents selected from the class consisting of a halogen atom, a $C_{1-6}$ alkyl group, a $C_{6-10}$ aryl group, a $C_{7-12}$ aralkyl group and a nitro group,
(8) a 5-membered aromatic heterocyclic group which may have 1 to 4 substituents selected from the class consisting of a halogen atom, a $C_{1-6}$ alkyl group, a $C_{5-10}$ aryl group, a $C_{7-12}$ aralkyl group and a nitro group, or
(10) a tri-$C_{1-4}$ alkylsilyl,
(C) an amino group which may have 1 or 2 substituents selected from the class consisting of
  (C-1) an optionally substituted hydrocarbon group selected from the class consisting of (i) a $C_{1-6}$ alkyl group, (ii) a $C_{3-8}$ cycloalkyl group, (iii) a $C_{2-6}$ alkenyl group, (iv) a $C_{2-6}$ alkynyl group, (v) a $C_{3-8}$ cycloalkenyl group, (vi) a $C_{6-10}$ aryl group and (vii) a $C_{7-12}$ aralkyl group, each of said hydrocarbon group being unsubstituted or substituted by 1 to 4 substituents selected from the class consisting of (1) a nitro group, (2) a hydroxy group, (3) an oxo group, (4) a thioxo group, (5) a cyano group, (6) a carbamoyl group, (7) a carboxyl group, (8) a $C_{1-6}$ alkoxy-carbonyl group, (9) a halogen atom, (10) a $C_{1-6}$ alkoxy group, (11) a phenoxy group, (12) a phenoxy group substituted with 1 to 3 halogen atoms, (13) a $C_{1-6}$ alkylthio group, (14) a phenylthio group, (15) a $C_{1-6}$ alkylsulfinyl group, (16) a $C_{1-6}$ alkylsulfonyl group, (17) an amino group, (18) a $C_{1-6}$ alkanoylamino group, (19) a mono- or di-$C_{1-6}$ alkylamino group, (20) a $C_{1-6}$ acyl group, (21) a benzoyl group, (22) a 5- to 6-membered heterocyclic group containing, besides carbon atoms, 1 to 3 hetero-atoms selected from oxygen atom, sulfur atom and nitrogen atom which may have 1 to 4 substituents selected from the class consisting of (a) a halogen atom, (b) a $C_{1-6}$ alkyl group and (c) a phenoxy group substituted with 1 to 3 halogen atoms, (23) a $C_{1-6}$ alkyl group substituted with 1 to 3 halogen atoms, (24) a $C_{1-6}$ alkyl group and (25) a $C_{3-8}$ cycloalkyl group, and
  (C-2) an acyl group represented by the formula:

$$R^4CO—, R^5OCO—, R^6SO_2— \text{ or } R^7SO—$$

wherein $R^4$, $R^5$, $R^6$ and $R^7$ are independently
  (C-2-1) an optionally substituted hydrocarbon group selected from the class consisting of (i) a $C_{1-6}$ alkyl group, (ii) a $C_{3-8}$ cycloalkyl group, (iii) a $C_{2-6}$ alkenyl group, (iv) a $C_{2-6}$ alkynyl group, (v) a $C_{3-8}$ cycloalkenyl group, (vi) a $C_{6-10}$ aryl group and (vii) a $C_{7-12}$ aralkyl group, each of said hydrocarbon group being unsubstituted or substituted by 1 to 4 substituents selected from the class consisting of (1) a nitro group, (2) a hydroxy group, (3) an oxo group, (4) a thioxo group, (5) a cyano group, (6) a carbamoyl group, (7) a carboxyl group, (8) a $C_{1-6}$ alkoxy-carbonyl group, (9) a halogen atom, (10) a $C_{1-6}$ alkoxy group, (11) a phenoxy group, (12) a phenoxy group substituted with 1 to 3 halogen atoms (13) a $C_{1-6}$ alkylthio group, (14) a phenylthio, (15) a $C_{1-6}$ alkylsulfinyl group, (16) a $C_{1-6}$ alkylsulfonyl group, (17) an amino group, (18) a $C_{1-6}$ alkanoylamino, (19) a mono- or di-$C_{1-6}$ alkylamino group, (20) a $C_{1-6}$ acyl group, (21) a benzoyl group, (22) a 5- to 6-membered heterocyclic group containing, besides carbon atoms, 1 to 3 hetero-atoms selected from oxygen atom, sulfur atom and nitrogen atom which may have 1 to 4 substituents selected from the class consisting of (a) a halogen atom, (b) a $C_{1-6}$ alkyl group and (c) a phenoxy group substituted with 1 to 3 halogen atoms, (23) a $C_{1-6}$ alkyl group substituted with 1 to 3 halogen atoms, (24) a $C_{1-6}$ alkyl group and (25) a $C_{3-8}$ cycloalkyl group, or
  (C-2-2) a basic 5- to 7-membered heterocyclic group containing, besides carbon atoms, 1 to 3 hetero-atoms selected from oxygen atom, sulfur atom and nitrogen atom, which may have 1 to 5 substituents selected from the class consisting of (1) a $C_{1-6}$ alkyl group, (2) a $C_{2-6}$ alkenyl group, (3) a $C_{2-6}$ alkynyl group, (4) a $C_{3-8}$ cycloalkyl group, (5) a $C_{3-8}$ cycloalkenyl group, (6) a $C_{7-12}$ aralkyl group, (7) a $C_{6-10}$ aryl group, (8) a $C_{1-6}$ alkoxy group, (9) a phenoxy group, (10) a $C_{1-6}$ alkanoyl group, (11) a benzoyl group, (12) a $C_{1-6}$ alkanoyloxy group, a benzoyloxy group, (13) a carboxyl group, (14) a $C_{1-6}$ alkoxy-carbonyl group, (15) a carbamoyl group, (16) a N-mono-$C_{1-6}$ alkyl-carbamoyl group, (17) N,N-di-$C_{1-6}$ alkyl-carbamoyl group, (18) a cyclic aminocarbonyl group, (19) a halogen atom, (20) a halogeno $C_{1-6}$ alkyl group, (21) an oxo group, (22) an amidino group, (23) an imino group, (24) an amino group, (25) a mono-$C_{1-6}$ alkylamino group, (26) a di-$C_{1-6}$ alkylamino group, (27) a 3- to 6-membered cyclic amino group, (28) a $C_{1-6}$ alkanoylamido group, (29) a benzamido group, (30) a carbamoylamino group, (31) a N-mono-$C_{1-6}$ alkylcarbamoylamino group, (32) a N,N-di-$C_{1-6}$ alkylcarbamoylamino group, (33) a $C_{1-3}$ alkylenedioxy group, (34) a sulfamoyl group, (35) a $C_{1-6}$ alkylsulfamoyl group, (36) a di-$C_{1-6}$ alkylsulfamoyl group, (37) a $C_{1-6}$ alkylthio group, (38) a $C_{6-10}$ arylthio group, (39) a $C_{1-6}$ alkylsulfinyl group, (40) a $C_{6-10}$ arylsulfinyl group, (41) a $C_{1-6}$ alkyl-sulfonyl group and (42) a $C_{6-10}$ arylsulfonyl group, or
(D) a hydrocarbon group which may be bound through a carbonyl group, a thio group, a sulfinyl group or a sulfonyl group, said hydrocarbon group being selected from the class consisting of (i) a $C_{1-6}$ alkyl group, (ii) a $C_{3-8}$ cycloalkyl group, (iii) a $C_{2-6}$ alkenyl group, (iv) a $C_{2-6}$ alkynyl group, (v) a $C_{3-8}$ cycloalkenyl group, (vi) a $C_{6-10}$ aryl group and (vii) a $C_{7-12}$ aralkyl group, and each of said hydrocarbon group being unsubstituted or substituted by 1 to 4 substituents selected from the class consisting of (1) a nitro group, (2) a hydroxy group, (3)

an oxo group, (4) a thioxo group, (5) a cyano group, (6) a carbamoyl group, (7) a carboxyl group, (8) a $C_{1-6}$ alkoxy-carbonyl group, (9) a halogen atom, (10) a $C_{1-6}$ alkoxy group, (11) a phenoxy group, (12) a phenoxy group substituted with 1 to 3 halogen atoms, (13) a $C_{1-6}$ alkylthio group, (14) a phenylthio group, (15) a $C_{1-6}$ alkylsulfinyl group, (16) a $C_{1-6}$ alkylsulfonyl group, (17) an amino group, (18) a $C_{1-6}$ alkanoylamino group, (19) a mono- or di-$C_{1-6}$ alkylamino group, (20) a $C_{1-6}$ acyl group, (21) a benzoyl group, (22) a 5- to 6-membered heterocyclic group containing, besides carbon atoms, 1 to 3 hetero-atoms selected from oxygen atom, sulfur atom and nitrogen atom which may have 1 to 4 substituents selected from the class consisting of (a) a halogen atom, (b) a $C_{1-6}$ alkyl group and (c) a phenoxy group substituted with 1 to 3 halogen atoms, (23) a $C_{1-6}$ alkyl group substituted with 1 to 3 halogen atoms, (24) a $C_{1-6}$ alkyl group and (25) a $C_{3-8}$ cycloalkyl group;

$R^2$ is a hydrogen atom or an optionally substituted hydrocarbon group selected from the class consisting of (i) a $C_{1-6}$ alkyl group, (ii) a $C_{3-8}$ cycloalkyl group, (iii) a $C_{2-6}$ alkenyl group, (iv) a $C_{2-6}$ alkynyl group, (v) a $C_{3-8}$ cycloalkenyl group, (vi) a $C_{6-10}$ aryl group and (vii) a $C_{7-12}$ aralkyl group, each of said hydrocarbon group being unsubstituted or substituted by 1 to 4 substituents selected from the class consisting of (1) a nitro group, (2) a hydroxy group, (3) an oxo group, (4) a thioxo group, (5) a cyano group, (6) a carbamoyl group, (7) a carboxyl group, (8) a $C_{1-6}$ alkoxy-carbonyl group, (9) a halogen atom, (10) a $C_{1-6}$ alkoxy group, (11) a phenoxy group, (12) a phenoxy group substituted with 1 to 3 halogen atoms, (13) a $C_{1-6}$ alkylthio group, (14) a phenylthio group, (15) a $C_{1-6}$ alkylsulfinyl group, (16) a $C_{1-6}$ alkylsulfonyl group, (17) an amino group, (18) a $C_{1-6}$ alkanoylamino group, (19) a mono- or di-$C_{,-6}$ alkylamino group, (20) a $C_{1-6}$ acyl group, (21) a benzoyl group, (22) a 5- to 6-membered heterocyclic group containing, besides carbon atoms, 1 to 3 hetero-atoms selected from oxygen atom, sulfur atom and nitrogen atom which may have 1 to 4 substituents selected from the class consisting of (a) a halogen atom, (b) a $C_{1-6}$ alkyl group and (c) a phenoxy group substituted with 1 to 3 halogen atoms, (23) a $C_{1-6}$ alkyl group substituted with 1 to 3 halogen atoms, (24) a $C_{1-6}$ alkyl group and (25) a $C_{3-8}$ cycloalkyl group;

$R^3$ is a group of the formula:

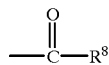

wherein $R^8$ is
(A) a hydroxy group,
(B) a $C_{1-6}$ alkoxy group optionally substituted with 1 to 3 substituents selected from the class consisting of (1) a hydroxy group, (2) an amino group, (3) a mono-$C_{1-6}$ alkylamino group, (4) a di-$C_{1-6}$ alkylamino group, (5) a piperidino group, (6) a morpholino group, (7) a halogen atom, (8) a $C_{1-6}$ alkoxy group, (9) a $C_{1-6}$ alkylthio group, (10) a $C_{1-6}$ alkoxy-carbonyl group, (11) a propylidene group, (12) a 3-phthalidylidene group and (13) a 5-methyl-2-oxo-1,3-dioxolan-4-yl group,
(C) a group of the formula: —OCH($R^{11}$)OCO$R^{12}$ in which $R^{11}$ is (1) a hydrogen atom, (2) a straight-chain or branched $C_{1-6}$ alkyl group or (3) a $C_{5-7}$ cycloalkyl group, and $R^{12}$ is (1) a straight-chain or branched $C_{1-6}$ alkyl group, (2) a $C_{2-8}$ alkenyl group, (3) a $C_{5-7}$ cycloalkyl group, (4) a $C_{1-3}$ alkyl group substituted with $C_{5-7}$ cycloalkyl or $C_{6-10}$ aryl, said aryl being optionally substituted with 1 to 3 substituents selected from the class consisting of a halogen atom, a nitro group and a $C_{1-6}$ alkyl group, (5) a $C_{2-3}$ alkenyl group substituted with $C_{5-7}$ cycloalkyl or $C_{6-10}$ aryl, said aryl being optionally substituted with 1 to 3 substituents selected from the class consisting of a halogen atom, a nitro group and a $C_{1-6}$ alkyl group, (6) a $C_{6-10}$ aryl group, said aryl being optionally substituted with 1 to 3 substituents selected from the class consisting of a halogen atom, a nitro group and a $C_{1-6}$ alkyl group, (7) a straight-chain or branched $C_{1-6}$ alkoxy group, (8) a straight-chain or branched $C_{2-8}$ alkenyloxy group, (9) a $C_{5-7}$ cycloalkyloxy group, (10) a $C_{1-3}$ alkoxy group substituted with $C_{5-7}$ cycloalkyl or $C_{6-10}$ aryl, said aryl being optionally substituted with 1 to 3 substituents selected from the class consisting of a halogen atom, a nitro group and a $C_{1-6}$ alkyl group, (11) a $C_{2-3}$ alkenyloxy group substituted with $C_{5-7}$ cycloalkyl or $C_{6-10}$ aryl, said aryl being optionally substituted with 1 to 3 substituents selected from the class consisting of a halogen atom, a nitro group and a $C_{1-6}$ alkyl group, or (12) a $C_{6-10}$ aryloxy group, said aryl being optionally substituted with 1 to 3 substituents selected from the class consisting of a halogen atom, a nitro group and a $C_{1-6}$ alkyl group,
(D) a $C_{2-8}$ alkenyloxy group,
(E) a $C_{7-12}$ aralkyloxy group, or
(F) a group of the formula:

wherein $R^9$ and $R^{10}$ are the same or different
(F-1) a hydrogen atom,
(F-2) a $C_{1-6}$ alkyl group,
(F-3) a $C_{2-8}$ alkenyl group, or
(F-4) a $C_{7-12}$ aralkyl group, the aryl group of which is unsubstituted or substituted with one or two substituents selected from the class consisting of (1) a nitro group, (2) a halogen atom, (3) a $C_{1-6}$ alkyl group and (4) a $C_{1-6}$ alkoxy group; and D is a $C_{1-6}$ alkyl group substituted with a group of the formula:

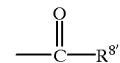

wherein $R^8$ is
(A) a hydroxy group,
(B) a $C_{1-6}$ alkoxy group optionally substituted with 1 to 3 substituents selected from the class consisting of (1) a hydroxy group, (2) an amino group, (3) a mono-$C_{1-6}$ alkylamino group, (4) a di-$C_{1-6}$ alkylamino group, (5) a piperidino group, (6) a morpholino group, (7) a halogen atom, (8) a $C_{1-6}$ alkoxy group, (9) a $C_{1-6}$ alkylthio group, (10) a $C_{1-6}$ alkoxy-carbonyl group, (11) a propylidene group, (12) a 3-phthalidylidene group and (13) a 5-methyl-2-oxo-1,3-dioxolan-4-yl group,
(C) a group of the formula: —OCH($R^{11}$)OCO$R^{12}$ in which $R^{11}$ is (1) a hydrogen atom, (2) a straight-chain or branched $C_{1-6}$ alkyl group or (3) a $C_{5-7}$ cycloalkyl group, and $R^{12}$ is (1) a straight-chain or branched $C_{1-6}$ alkyl group, (2) a $C_{2-8}$ alkenyl group, (3) a $C_{5-7}$ cycloalkyl group, (4) a $C_{1-3}$ alkyl group substituted with $C_{5-7}$ cycloalkyl or $C_{6-10}$ aryl, said aryl being optionally substituted with 1 to 3 substituents selected from the class consisting of a halogen atom, a nitro group and a $C_{1-6}$ alkyl group, (5) a $C_{2-3}$ alkenyl group substituted with $C_{5-7}$ cycloalkyl or $C_{6-10}$ aryl, said aryl being optionally substituted with 1 to 3 substituents selected from the class consisting of a halogen atom, a nitro group and a $C_{1-6}$ alkyl group, (6) a $C_{6-10}$ aryl group, said aryl being optionally substituted with 1 to 3 substituents selected from the class consisting of a halogen atom, a nitro group and a $C_{1-6}$ alkyl group, (7) a straight-chain or branched $C_{1-6}$ alkoxy group, (8) a straight-chain or branched $C_{2-8}$ alkenyloxy group, (9) a $C_{5-7}$ cycloalkyloxy group, (10) a $C_{1-3}$ alkoxy group substituted with $C_{5-7}$ cycloalkyl or $C_{6-10}$ aryl, said aryl being optionally substituted with 1 to 3 substituents selected from the class consisting of a halogen atom, a nitro group and a $C_{1-6}$ alkyl group, (11) a $C_{2-3}$ alkenyloxy group substituted with $C_{5-7}$ cycloalkyl or $C_{6-10}$ aryl, said aryl being optionally substituted with 1 to 3 substituents selected from the class consisting of a halogen atom, a nitro group and a $C_{1-6}$ alkyl group, or (12) a $C_{6-10}$ aryloxy group, said aryl being optionally substituted with 1 to 3 substituents selected from the class consisting of a halogen atom, a nitro group and a $C_{1-6}$ alkyl group, (D) a $C_{2-8}$ alkenyloxy group, or (E) a $C_{7-12}$ aralkyloxy group;

(5) a compound of the above (1), wherein the ring A is a basic 6-membered heterocyclic group which may be substituted and which contains 1 to 2 nitrogen atoms;

(6) a compound of the above (5), wherein the basic 6-membered heterocyclic group is pyridyl, pyrimidinyl or piperidyl;

(7) a compound of the above (5), wherein the basic 6-membered heterocyclic group is piperidyl;

(8) a compound of the above (5), wherein the basic 6-membered heterocyclic group is pyridyl;

(9) a compound of the above (2), wherein the ring $A^1$ is pyridyl;

(10) a compound of the above (1), wherein the ring B is a divalent 6-membered nitrogen containing heterocyclic group which contains 1 or 2 nitrogen atoms and which may be substituted or a phenylene group which may be substituted;

(11) a compound of the above (1) or (2), wherein the ring B is phenylene, piperidinydiyl or piperazinediyl, each of which may be substituted;

(12) a compound of the above (1) or (2), wherein the ring B is phenylene which may be substituted;

(13) a compound of the above (1) or (2), wherein the ring B is piperazinediyl which may be substituted;

(14) a compound of the above (2) or (3), wherein $Y^1$ is an imino group which may have 1 or 2 substituents selected from the class consisting of (1) a $C_{1-6}$ alkoxy group, (2) a $C_{1-6}$ alkyl group substituted with 1 to 3 halogen atoms, (3) a $C_{1-6}$ acyl group, (4) a hydroxy-$C_{1-6}$ alkyl, (5) a $C_{1-6}$ alkoxy-$C_{1-6}$ alkyl group and (6) a $C_{1-6}$ alkoxy-carbonyl group;

(15) a compound of the above (1), (2) or (3), wherein $R^1$ is a hydrogen atom, an optionally substituted hydroxy group, an optionally substituted lower alkyl group or an optionally substituted amino group;

(16) a compound of the above (1), (2) or (3), wherein $R^1$ is a hydroxy group optionally substituted with a $C_{1-6}$ alkyl-carbonyl group;

(17) a compound of the above (1), (2) or (3), wherein $R^1$ is an optionally substituted amino group selected from the class consisting of (1) an amino group optionally substituted with a $C_{1-6}$ acyl group, (2) a mono-$C_{1-6}$ alkylamino group, (3) a di-$C_{1-6}$ alkylamino group, (4) a $C_{1-6}$ alkoxy-carbonylamino group, (5) a $C_{1-6}$ alkylthio-carbonylamino group, (6) a $C_{7-12}$ aralkylamino group which may have 1 to 3 substituents selected from the class consisting of a halogen atom, a $C_{1-6}$ alkyl group and a $C_{1-6}$ alkoxy group, (7) a benzoylamino group which may have 1 to 3 substituents selected from the class consisting of a halogen atom, a $C_{1-6}$ alkyl group and a $C_{1-6}$ alkoxy group, (8) a benzene-sulfonylamino group which may have 1 to 3 substituents selected from the class consisting of a halogen atom, a $C_{1-6}$ alkyl group and a $C_16$ alkoxy group, and (9) a $C_{1-6}$ alkoxy-carbonylamino group which may be substituted with $C_{1-6}$ alkanoyloxy, benzoyloxy, $C_{1-6}$ alkoxy-carbonyloxy, $C_{3-8}$ cycloalkyl-oxycarbonyloxy, $C_{3-8}$ cycloalkyl-carbonyloxy, 6-membered aromatic heterocyclic group-carbonyloxy or 5-methyl-2-oxo-1,3-dioxolan-4-yl;

(18) a compound of the above (1), (2) or (3), wherein $R^1$ is an optionally substituted hydrocarbon group which may be bound through a carbonyl group, a thio group, a sulfinyl group or a sulfonyl group, being selected from the class consisting of (1) a $C_{1-6}$ alkyl-carbonyl group, (2) a $C_{1-6}$ alkylthio group, (3) a $C_{1-6}$ alkylsulfinyl group, (4) a $C_{1-6}$ alkylsulfonyl group, (5) a benzoyl group which may have 1 to 3 substituents selected from the class consisting of a halogen atom, a $C_{1-6}$ alkyl group and a $C_{1-6}$ alkoxy group, (6) a phenylthio group which may have 1 to 3 substituents selected from the class consisting of a halogen atom, a $C_{1-6}$ alkyl group, a $C_{1-6}$ alkoxy group, (7) a phenylsulfinyl group which may have 1 to 3 substituents selected from the class consisting of a halogen atom, a $C_{1-6}$ alkyl group and a $C_{1-6}$ alkoxy group, (8) a phenylsulfonyl group which may have 1 to 3 substituents selected from the class consisting of a halogen atom, a $C_{1-6}$ alkyl group and a $C_{1-6}$ alkoxy group, (9) a $C_{7-12}$ aralkyl-carbonyl group which may have 1 to 3 substituents selected from the class consisting of a halogen atom, a $C_{1-6}$ alkyl group and a $C_{1-6}$ alkoxy group, (10) a $C_{7-12}$ aralkylthio group which may have 1 to 3 substituents selected from the class consisting of a halogen atom, a $C_{1-6}$ alkyl group and a $C_{1-6}$ alkoxy group, (11) a $C_{7-12}$ aralkyl-sulfinyl group which may have 1 to 3 substituents selected from the class consisting of a halogen atom, a $C_{1-6}$ alkyl group and a $C_{1-6}$ alkoxy group, (12) a $C_{7-12}$ aralkyl-sulfonyl group which may have 1 to 3 substituents selected from the class consisting of a halogen atom, a $C_{1-6}$ alkyl group and a $C_{1-6}$ alkoxy group, and (13) a $C_{1-6}$ alkyl group optionally substituted with a $C_{6-10}$ aryl group which may have 1 to 3 substituents selected from the class consisting of a halogen atom, a $C_{1-6}$ alkyl group and a $C_{1-6}$ alkoxy group;

(19) a compound of the above (1), (2) or (3), wherein $R^2$ is a hydrogen atom;

(20) a compound of the above (1), (2) or (3), wherein $R^3$ is a carboxyl group or a $C_{1-6}$ alkoxy-carbonyl group;

(21) a compound of the above (1), (2) or (3), wherein $R^3$ is methoxycarbonyl, ethoxycarbonyl, t-butoxycarbonyl, propoxycarbonyl, pivaloyloxymethoxycarbonyl, 1-(cyclohexyloxycarbonyloxy)ethoxycarbonyl, 5-methyl-2-oxo-1,3-dioxolan-4-ylmethoxycarbonyl, acetoxymethyloxycarbonyl, propionyloxymethoxycarbonyl, n-butyryloxymethoxycarbonyl, isobutyryloxymethoxycarbonyl, 1-(ethoxycarbonyloxy)ethoxycarbonyl, 1-(acetyloxy)ethyloxycarbonyl, 1-(isobutyryloxy)ethoxycarbonyl, cyclohexylcarbonyloxymethoxycarbonyl, benzoyloxymethoxycarbonyl, cinnamyloxycarbonyl, cyclopentylcarbonyloxy-methoxycarbonyl, N,N-dimethylaminocarbonyl, 2-(iso-butyryloxycarbonyl)-2-propylideneethoxycarbonyl or 3-(phthalidylidene)ethoxycarbonyl;

(22) a compound of the above (1), (2) or (3), wherein D is a $C_{1-6}$ alkoxy-carbonyl-$C_{1-6}$ alkyl group;

(23) a compound of the above (1), wherein the ring A is pyridyl, pyrimidinyl or piperidyl; the ring B is phenylene, piperidinydiyl or piperazinediyl; Y is a methylene group; $R^1$ is (A) a hydrogen atom, (B) a hydroxy group optionally substituted with a $C_{1-6}$ alkyl-carbonyl group, (C) an amino group optionally substituted with one or two substituents selected from the class consisting of (1) a formyl group, (2) a $C_{2-6}$ alkanoyl group, (3) a $C_{1-6}$ alkyl group, (4) a $C_{1-6}$ alkoxy-carbonyl group, (5) a $C_{1-6}$ alkylthio-carbonyl group, (6) a $C_{7-12}$ aralkyl group which may have 1 to 3 substituents selected from the class consisting of a halogen atom, a $C_{1-6}$ alkyl group and a $C_{1-6}$ alkoxy group, (7) a benzoyl group which may have 1 to 3 substituents selected from the class consisting of a halogen atom, a $C_{1-6}$ alkyl group and a $C_{1-6}$ alkoxy group, (8) a benzenesulfonyl group which may have 1 to 3 substituents selected from the class consisting of a halogen atom, a $C_{1-6}$ alkyl group and a $C_{1-6}$ alkoxy group, and (9) a $C_{1-6}$ alkoxy-carbonyl group which may be substituted with $C_{1-6}$ alkanoyloxy, benzoyloxy, $C_{1-6}$ alkoxy-carbonyloxy, $C_{3-8}$ cycloalkyloxy-carbonyloxy, $C_{3-8}$ cycloalkyl-carbonyloxy, pyridyl-carbonyloxy or 5-methyl-2-oxo-1,3-dioxolan-4-yl, or (D) a $C_{1-6}$ alkyl group optionally substituted with a $C_{6-10}$ aryl group which may have 1 to 3 substituents selected from the class consisting of a halogen atom, a $C_{1-6}$ alkyl group and a $C_{1-6}$ alkoxy group; $R^2$ is a hydrogen atom; $R^3$ is a carboxyl group or a $C_{1-6}$ alkoxy-carbonyl group; and D is a $C_{1-6}$ alkoxy-carbonyl-$C_{1-6}$ alkyl group;

(24) a compound of the above (2), wherein the ring $A^1$ is pyridyl or pyrimidinyl; the ring B is phenylene, piperidinydiyl or piperazinediyl; $Y^1$ is an imino group; $R^1$ is (A) a hydrogen atom, (B) a hydroxy group optionally substituted with a $C_{1-6}$ alkyl-carbonyl group, (C) an amino group optionally substituted with one or two substituents selected from the class consisting of (1) a formyl group, (2) $C_{2-6}$ alkanoyl group, (3) a $C_{1-6}$ alkyl group, (4) a $C_{1-6}$ alkoxy-carbonyl group, (5) a $C_{1-6}$ alkylthio-carbonyl group, (6) a $C_{7-12}$ aralkyl group which may have 1 to 3 substituents selected from the class consisting of a halogen atom, a $C_{1-6}$ alkyl group and a C alkoxy group, (7) a benzoyl group which may have 1 to 3 substituents selected from the class consisting of a halogen atom, a $C_{1-6}$ alkyl group and a $C_{1-6}$ alkoxy group, (8) a benzenesulfonyl group which may have 1 to 3 substituents selected from the class consisting of a halogen atom, a $C_{1-6}$ alkyl group and a $C_{1-6}$ alkoxy group, and (9) a $C_{1-6}$ alkoxy-carbonyl group which may be substituted with $C_{1-6}$ alkanoyloxy, benzoyloxy, $C_{1-6}$ alkoxy-carbonyloxy, $C_{3-8}$ cycloalkyloxy-carbonyloxy, $C_{3-8}$ cycloalkyl-carbonyloxy, pyridyl-carbonyloxy or 5-methyl-2-oxo-1,3-dioxolan-4-yl, or (D) a $C_{1-6}$ alkyl group optionally substituted with a $C_{6-10}$ aryl group which may have 1 to 3 substituents selected from the class consisting of a halogen atom, a $C_{1-6}$ alkyl group and a $C_{1-6}$ alkoxy group; $R^2$ is a hydrogen atom; $R^3$ is a carboxyl group or a $C_{1-6}$ alkoxy-carbonyl group; and D is a $C_{1-6}$ alkoxy-carbonyl-$C_{1-6}$ alkyl group;

(25) a compound of the above (24), wherein the ring $A^1$ is pyridyl; the ring B is phenylene or piperidinediyl; $Y^1$ is an imino group; $R^1$ is (A) a hydrogen atom or (B) a $C_{1-6}$ alkyl group optionally substituted with a $C_{6-10}$ aryl group which may have a $C_{1-6}$ alkoxy group; $R^2$ is a hydrogen atom; $R^3$ is a carboxyl group or a $C_{1-6}$ alkoxy-carbonyl group; and D is a $C_{1-6}$ alkoxy-carbonyl-$C_{1-6}$ alkyl group;

(26) a compound of the above (3), wherein the ring $A^2$ is piperidyl; the ring $B^1$ is phenylene; $Y^1$ is an imino group; $R^1$ is (A) a hydrogen atom, (B) a hydroxy group optionally substituted with a $C_{1-6}$ alkyl-carbonyl group, (C) an amino group optionally substituted with one or two substituents selected from the class consisting of (1) a formyl group, (2) $C_{2-6}$ alkanoyl group, (3) a $C_{1-6}$ alkyl group, (4) a $C_{1-6}$ alkoxy-carbonyl group, (5) a $C_{1-6}$ alkylthio-carbonyl group, (6) a $C_{7-12}$ aralkyl group which may have 1 to 3 substituents selected from the class consisting of a halogen atom, a $C_{1-6}$ alkyl group and a $C_{1-6}$ alkoxy group, (7) a benzoyl group which may have 1 to 3 substituents selected from the class consisting of a halogen atom, a $C_{1-6}$ alkyl group and a $C_{1-6}$ alkoxy group, (8) a benzenesulfonyl group which may have 1 to 3 substituents selected from the class consisting of a halogen atom, a $C_{1-6}$ alkyl group and a $C_{1-6}$ alkoxy group, and (9) a $C_{1-6}$ alkoxy-carbonyl group which may be substituted with $C_{1-6}$ alkanoyloxy, benzoyloxy, $C_{1-6}$ alkoxy-carbonyloxy, $C_{3-8}$ cycloalkyloxy-carbonyloxy, $C_{3-8}$ cycloalkyl-carbonyloxy, pyridyl-carbonyloxy or 5-methyl-2-oxo-1,3-dioxolan-4-yl, or (D) a $C_{1-6}$ alkyl group optionally substituted with a $C_{6-10}$ aryl group which may have 1 to 3 substituents selected from the class consisting of a halogen atom, a $C_{1-6}$ alkyl group and a $C_{1-6}$ alkoxy group; $R^2$ is a hydrogen atom; $R^3$ is a carboxyl group or a $C_{1-6}$ alkoxy-carbonyl group; and D is a $C_{1-6}$ alkoxy-carbonyl-$C_{1-6}$ alkyl group;

(27) a compound of the above (26), wherein $R^1$ is (A) a hydrogen atom or (B) a $C_{1-6}$ alkyl group optionally substituted with a $C_{6-10}$ aryl group which may have a $C_{1-6}$ alkoxy group;

(28) a compound of the above (1), which is (S,S)-[4-[2-(4-methoxybenzenesulfonylamino)-4-oxo-(4-pyridin-4-yl-piperazin-1-yl)butyryl]-3-methoxycarbonyl-methyl-2-oxo-piperazin-1-yl]acetic acid, (S,S)-[4-[2-(4-methoxy-benzylamino)-4-oxo-(4-pyridin-4-ylpiperazin-1-yl)-butyryl]-3-methoxycarbonylmethyl-2-oxo-piperazin-1-yl]-acetic acid, or a pharmaceutically acceptable salt thereof;

(29) a pharmaceutical composition which comprises a compound or a salt thereof according to any one of the above (1)–(3);

(30) a pharmaceutical composition for inhibiting cell-adhesion which comprises a compound or a salt thereof according to the above (1)–(3);

(31) a pharmaceutical composition for treating or preventing angina pectoris, which comprises a compound or a salt thereof according to any one of the above (1)–(3), in admixture with a pharmaceutically acceptable carrier or excipient;

(32) a pharmaceutical composition for treating or preventing unstable angina, which comprises a compound or a salt thereof according to any one of the above (1)–(3), in admixture with a pharmaceutically acceptable carrier or excipient;

(33) a pharmaceutical composition for treating or preventing ischemic complication, reobstruction or restenosis after percutaneous transluminal coronary angioplasty or coronary thrombolytic therapy, which comprises a compound or a salt thereof according to any one of the above (1)–(3), in admixture with a pharmaceutically acceptable carrier or excipient;

(34) Use of a compound or a salt thereof according to any one of the above (1)–(3) for manufacturing a pharmaceutical composition;

(35) Use of a compound or a salt thereof according to any one of the above (1)–(3) for manufacturing a pharmaceutical composition for inhibiting cell-adhesion;

(36) Use of a compound or a salt thereof according to any one of the above (1)–(3) for manufacturing a pharmaceutical composition for treating or preventing angina pectoris;

(37) Use of a compound or a salt thereof according to any one of the above (1)–(3) for manufacturing a pharmaceutical composition for treating or preventing unstable angina;

(38) Use of a compound or a salt thereof according to any one of the above (1)–(3) for manufacturing a pharmaceutical composition for treating or preventing ischemic complication, reobstruction or restenosis after percutaneous transluminal coronary angioplasty or coronary thrombolytic therapy;

(39) a method for inhibiting cell-adhesion in a mammal which comprises administering an effective amount of a compound or a salt thereof according to any one of the above (1)–(3) to said mammal;

(40) a method for preventing or treating angina pectoris, in a mammal which comprises administering an effective amount of a compound or a salt thereof according to any one of the above (1)–(3) to said mammal;

(41) a method for preventing or treating unstable angina in a mammal which comprises administering an effective amount of a compound or a salt thereof according to any one of the above (1)–(3) to said mammal;

(42) a method for preventing or treating ischemic complication, reobstruction or restenosis after percutaneous transluminal coronary angioplasty or coronary thrombolytic therapy in a mammal which comprises administering an effective amount of a compound or a salt thereof according to any one of the above (1)–(3) to said mammal;

(43) a method for producing a compound of the formula:

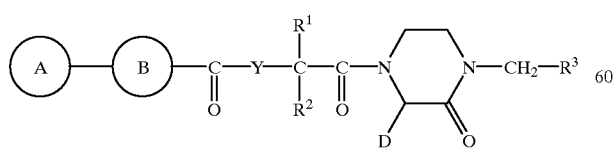

wherein the ring A is a basic 5- to 7-membered heterocyclic group which may be substituted; the ring B is a divalent 5- to 7-membered nitrogen containing heterocyclic group which may be substituted or a divalent 5- to 7-membered cyclic hydrocarbon group which may be substituted; Y is an optionally substituted methylene group; $R^1$ is a hydrogen atom, an optionally substituted hydroxy group, an optionally substituted amino group or an optionally substituted hydrocarbon group which may be bound through a carbonyl group, a thio group, a sulfinyl group or a sulfonyl group; $R^2$ is a hydrogen atom or an optionally substituted hydrocarbon group; $R^3$ is an optionally esterified or amidated carboxyl group; and D is a lower alkyl group substituted with an optionally esterified carboxyl group; or a salt thereof, which comprises subjecting a compound (II) of the formula:

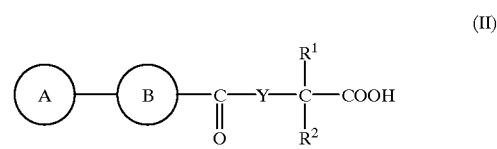

wherein each symbol is of the same meaning as defined above, or a salt thereof and a compound (III) of the formula:

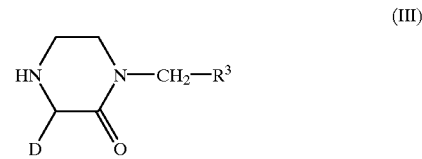

wherein each symbol is of the same meaning as defined above, or a salt thereof to condensation reaction;

(44) a method for producing a compound of the formula:

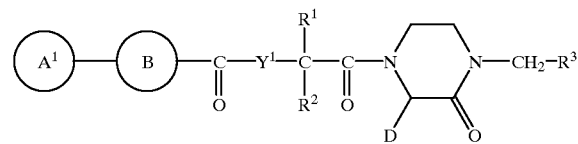

wherein the ring $A^1$ is a basic 5- to 7-membered aromatic heterocyclic group which may be substituted; the ring B is a divalent 5- to 7-membered nitrogen containing heterocyclic group which may be substituted or a divalent 5- to 7-membered cyclic hydrocarbon group which may be substituted; $Y^1$ is an optionally substituted imino group;

$R^1$ is a hydrogen atom, an optionally substituted hydroxy group, an optionally substituted amino group or an optionally substituted hydrocarbon group which may be bound through a carbonyl group, a thio group, a sulfinyl group or a sulfonyl group; $R^2$ is a hydrogen atom or an optionally substituted hydrocarbon group; $R^3$ is an optionally esterified or amidated carboxyl group; and D is a lower alkyl group substituted with an optionally esterified carboxyl group; or a salt thereof, which comprises subjecting a compound (II-1) of the formula:

(II-1)

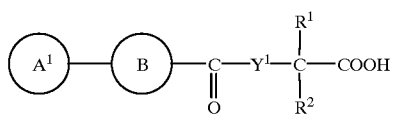

wherein each symbol is of the same meaning as defined above, or a salt thereof and a compound (III) of the formula:

(III)

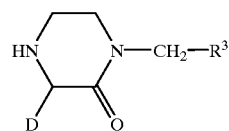

wherein each symbol is of the same meaning as defined above, or a salt thereof to condensation reaction; or subjecting a compound (IV) of the formula:

(IV)

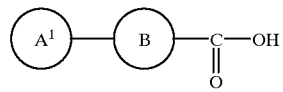

wherein each symbol is of the same meaning as defined above, or a salt thereof and a compound (V) of the formula:

(V)

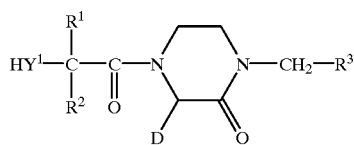

wherein each symbol is of the same meaning as defined above, or a salt thereof to condensation reaction;

(45) a method for producing a compound of the formula:

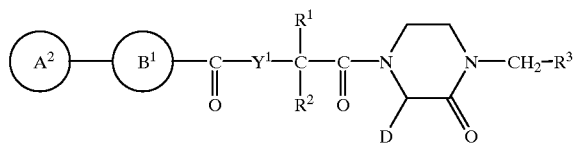

wherein the ring $A^2$ is a piperidyl group which may be substituted; the ring $B^1$ is a phenylene group which may be substituted; $Y^1$ is an optionally substituted imino group;

$R^1$ is a hydrogen atom, an optionally substituted hydroxy group, an optionally substituted amino group or an optionally substituted hydrocarbon group which may be bound through a carbonyl group, a thio group, a sulfinyl group or a sulfonyl group; $R^2$ is a hydrogen atom or an optionally substituted hydrocarbon group; $R^3$ is an optionally esterified or amidated carboxyl group; and D is a lower alkyl group substituted with an optionally esterified carboxyl group; or a salt thereof, which comprises subjecting a compound (II-2) of the formula:

(II-2)

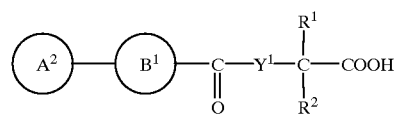

wherein each symbol is of the same meaning as defined above,
or a salt thereof and a compound (III) of the formula:

(III)

wherein each symbol is of the same meaning as defined above, or a salt thereof to condensation reaction; and

(46) a method for producing a compound of the formula:

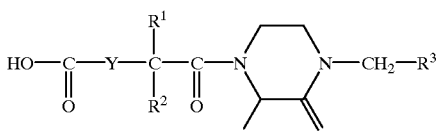

wherein the ring A is a basic 5- to 7-membered heterocyclic group which may be substituted; the ring B' is an optionally substituted piperazinediyl group; Y is an optionally substituted methylene group; $R^1$ is a hydrogen atom, an optionally substituted hydroxy group, an optionally substituted amino group or an optionally substituted hydrocarbon group which may be bound through a carbonyl group, a thio group, a sulfinyl group or a sulfonyl group;

$R^2$ is a hydrogen atom or an optionally substituted hydrocarbon group; $R^3$ is an optionally esterified or amidated carboxyl group; and D is a lower alkyl group substituted with an optionally esterified carboxyl group;

or a salt thereof, which comprises
subjecting a compound (VI) of the formula:

(VI)

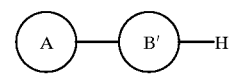

wherein B' is an optionally substituted piperazinediyl group and the other symbols are of the same meaning as defined above, or a salt thereof and a compound (VII) of the formula:

(VII)

wherein each symbol is of the same meaning as defined above, or a salt thereof to condensation reaction; etc.

In the above formula (I), the ring A represents a basic 5- to 7-membered heterocyclic group which may be substituted.

Specific examples of "5- to 7-membered heterocyclic group" in the "basic 5- to 7-membered heterocyclic group which may be substituted" represented by the ring A include a 5 -membered heterocyclic group containing, besides carbon atoms, 1 to 3 hetero-atoms selected from oxygen atom, sulfur atom, nitrogen atom, etc., such as pyrrolyl (1-, 2- or 3-pyrrolyl), pyrazolyl (1-, 3- or 4-pyrazolyl), imidazolyl (1-, 2- or 4-imidazolyl), triazolyl (1,2,3-triazolyl or 1,2,4-triazolyl), pyrrolidinyl (1-, 2- or 3-pyrrolidinyl), pyrrolinyl, imidazolinyl, pyrazolidinyl, pyrazolinyl, thiazolyl (2-, 4- or 5-thiazolyl), isothiazolyl (3-, 4- or 5-isothiazolyl), thiadiazolyl (3- or 5-(1,2,4-thiadiazolyl), 2- or 5-(1,3,4-thiadiazolyl), 4- or 5-(1,2,3-thiadiazolyl), 3- or 4-(1,2,5-thiadiazolyl)), oxazolyl (2-, 4- or 5-oxazolyl), isoxazolyl (3-, 4- or 5-isoxazolyl), oxadiazolyl (3- or 5-(1,2,4-oxadiazolyl), 1,3,4-oxadiazolyl), etc.; a 6-membered heterocyclic group containing, besides carbon atoms, 1 to 3 hetero-atoms selected from oxygen atom, sulfur atom, nitrogen atom, etc., such as pyridyl (2-, 3- or 4-pyridyl), pyrimidinyl (2-, 4- or 5-pyrimidinyl,), pyridazinyl (3- or 4-pyridazinyl), pyrazinyl, triazinyl (1,2,3-triazinyl, 1,2,4-triazinyl or 1,3,5-triazinyl), piperidyl (2-, 3- or 4-piperidyl), piperazinyl, pyridazinyl (3- or 4-pyridazinyl), pyrazinyl, thiadinyl (1,3-thiadinyl or 1,4-thiadinyl), thiomorpholinyl, morpholinyl, oxazinyl (1,2-oxazinyl, 1,3-oxazinyl or 1,4-oxazinyl), etc.; a 7-membered heterocyclic group containing, besides carbon atoms, 1 to 3 hetero-atoms selected from oxygen atom, sulfur atom, nitrogen atom, etc., such as azepinyl (1-, 2-, 3- or 4-azepinyl), diazepinyl (1-, 2-, 4- or 5-(1,3-diazepinyl), 1-, 2- or 5-(1,4-diazepinyl)), oxazepinyl (1-, 2-, 4-, 5-, 6- or 7-(1,3-oxazepinyl), 1-, 2-, 3-, 5-, 6- or 7-(1,4-oxazepinyl)), thiazepinyl (2-, 3-, 4-, 5-, 6- or 7-(1,3-thiazepinyl), 2-, 3-, 4-, 5-, 6- or 7-(1,4-thiazepinyl)), etc.; etc.

Among others, a basic 6-membered heterocyclic group containing 1 to 3 nitrogen atoms (preferably 1 to 2 nitrogen atoms) such as pyridyl, pyrimidinyl, pyridazinyl, pyrazinyl, triazinyl, piperidyl, piperazinyl, pyridazinyl, pyrazinyl, etc. is preferable. More preferable examples are pyridyl, pyrimidinyl, piperidyl, etc. and the most preferable example is pyridyl (preferably 4-pyridyl).

These heterocyclic groups may have 1 to 5 substituents (preferably 1 to 2 substituents) at any possible position.

Examples of the substituents include (1) $C_{1-6}$ alkyl groups (e.g. methyl, ethyl, propyl, isopropyl, butyl, sec-butyl, tert-butyl, etc.), (2) $C_{2-6}$ alkenyl groups (e.g. vinyl, allyl, 2-butenyl, 3-butenyl, etc.), (3) $C_{2-6}$ alkynyl groups (e.g. ethynyl, 2-propynyl, 3-hexynyl, etc.), (4) $C_{3-8}$ cycloalkyl groups (e.g. cyclopropyl, cyclobutyl, cyclopentyl, cyclohexyl, etc.), (5) $C_{3-8}$ cycloalkenyl groups (e.g. cyclopropenyl, cyclopentenyl, cyclohexenyl, etc.), (6) $C_{7-12}$ aralkyl groups (e.g. phenyl-$C_{1-6}$ alkyl groups such as benzyl, phenethyl, etc., etc.), (7) $C_{6-10}$ aryl groups (e.g. phenyl, naphthyl, etc.), (8) $C_{1-6}$ alkoxy groups (e.g. methoxy, ethoxy, propoxy, isopropoxy, butoxy, isobutoxy, sec-butoxy, tert-butoxy, etc.), (9) phenoxy,

(10) $C_{1-6}$ alkanoyl groups (e.g. formyl, acetyl, propionyl, butyryl, isobutyryl, etc.),

(11) benzoyl,

(12) $C_{1-6}$ alkanoyloxy groups (e.g. formyloxy, acetyloxy, propionyloxy, butyryloxy, isobutyryloxy, etc.), benzoyloxy,

(13) carboxyl group,

(14) $C_{1-6}$ alkoxy-carbonyl groups (e.g. methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, etc.),

(15) carbamoyl group,

(16) N-mono-$C_{1-6}$ alkyl-carbamoyl groups (e.g. N-methylcarbamoyl, N-ethylcarbamoyl, N-propylcarbamoyl, N-isopropylcarbamoyl, N-butylcarbamoyl, etc.),

(17) N,N-di-$C_{1-6}$ alkyl-carbamoyl groups (e.g. N,N-dimethylcarbamoyl, N,N-diethylcarbamoyl, N,N-dipropylcarbamoyl, N,N-dibutylcarbamoyl, etc.),

(18) cyclic amino-carbonyl groups (e.g. 1-aziridinylcarbonyl, 1-azetidinylcarbonyl, 1-pyrrolidinylcarbonyl, 1-piperidinylcarbonyl, N-methylpiperazinylcarbonyl, morpholinocarbonyl, etc.),

(19) halogen atoms (e.g. fluorine, chlorine, bromine, iodine),

(20) halogeno $C_{1-6}$ alkyl groups (e.g. $C_{1-6}$ alkyl substituted with 1 to 3 halogen atoms such as chloromethyl, dichloromethyl, trifluoromethyl, trifluoroethyl, etc., etc.),

(21) oxo group,

(22) amidino group,

(23) imino group,

(24) amino group,

(25) mono-$C_{1-6}$ alkylamino groups (e.g. methylamino, ethylamino, propylamino, isopropylamino, butylamino, etc.),

(26) di-$C_{1-6}$ alkylamino groups (e.g. dimethylamino, diethylamino, dipropylamino, diisopropylamino, dibutylamino, etc.),

(27) cyclic amino groups (e.g. 3- to 6-membered cyclic amino group optionally containing 1 to 3 hetero atoms selected from oxygen, sulfur and nitrogen, besides carbon atoms and one nitrogen atom, such as aziridinyl, azetidinyl, pyrrolidinyl, pyrrolinyl, pyrrolyl, oxazolyl, imidazolyl, pyrazolyl, imidazolidinyl, piperidino, thiomorpholino, morpholino, dihydropyridyl, pyridyl, N-methylpiperazinyl, N-ethylpiperazinyl, etc., etc.),

(28) $C_{1-6}$ alkanoylamido groups (e.g. formamido, acetamido, trifluoroacetamido, propionylamido, butyrylamido, isobutyrylamido, etc.),

(29) benzamido group,

(30) carbamoylamino group,

(31) N-mono-$C_{1-6}$ alkyl-carbamoylamino groups (e.g. N-methylcarbamoylamino, N-ethylcarbamoylamino, N-propylcarbamoylamino, N-isopropylcarbamoylamino, N-butylcarbamoylamino, etc.),

(32) N,N-di-$C_{1-6}$ alkyl-carbamoylamino groups (e.g. N,N-di-methylcarbamoylamino, N,N-diethylcarbamoylamino, N,N-dipropylcarbamoylamino, N,N-dibutylcarbamoylamino, etc.),

(33) $C_{1-3}$ alkylenedioxy groups (e.g. methylenedioxy, ethylenedioxy, etc.),

(34) sulfamoyl group,

(35) $C_{1-6}$ alkylsulfamoyl groups (e.g. N-methylsulfamoyl, N-ethylsulfamoyl, N-propylsulfamoyl, N-isopropylsulfamoyl, N-butylsulfamoyl, etc.),

(36) di-$C_{1-6}$ alkylsulfamoyl groups (e.g. N,N-dimethylsulfamoyl, N,N-diethylsulfamoyl, N,N-dipropylsulfamoyl, N,N-dibutylsulfamoyl, etc.),

(37) $C_{1-6}$ alkylthio groups (e.g. methylthio, ethylthio, propylthio, isopropylthio, butylthio, sec-butylthio, tert-butylthio, etc.),

(38) $C_{6-10}$ arylthio groups (e.g. phenylthio, etc.),

(39) $C_{1-6}$ alkylsulfinyl groups (e.g. methylsulfinyl, ethylsulfinyl, propylsulfinyl, butylsulfinyl, etc.),

(40) $C_{6-10}$ arylsulfinyl groups (e.g. phenylsulfinyl, etc.),

(41) $C_{1-6}$ alkylsulfonyl groups (e.g. methylsulfonyl, ethylsulfonyl, propylsulfonyl, butylsulfonyl, etc.), and

(42) $C_{6-10}$ arylsulfonyl groups (e.g. phenylsulfonyl, etc.), etc.

As the ring A, for example, a basic 6-membered heterocyclic group which may be substituted and which contains 1 to 3 nitrogen atoms (preferably 1 to 2 nitrogen atoms), such as pyridyl, pyrimidinyl, pyridazinyl, pyrazinyl, triazinyl, piperidyl, piperazinyl, pyridazinyl, pyrazinyl, etc. is preferable. More preferable examples are pyridyl, pyrimidinyl, piperidyl, etc. and the most preferable example is pyridyl (preferably 4-pyridyl).

In the above formula (I-1), the ring $A^1$ represents a basic 5- to 7-membered aromatic heterocyclic group which may be substituted.

Specific examples of "5- to 7-membered aromatic heterocyclic group" in the "basic 5- to 7-membered aromatic heterocyclic group which may be substituted" represented by the ring $A^1$ include a 5-membered aromatic heterocyclic group containing, besides carbon atoms, 1 to 3 hetero-atoms selected from oxygen atom, sulfur atom, nitrogen atom, etc., such as pyrrolyl (1-, 2- or 3-pyrrolyl), pyrazolyl (1-, 3- or 4-pyrazolyl), imidazolyl (1-, 2- or 4-imidazolyl), triazolyl (1,2,3-triazolyl or 1,2,4-triazolyl), thiazolyl (2-, 4- or 5-thiazolyl), isothiazolyl (3-, 4- or 5-isothiazolyl), thiadiazolyl (3- or 5-(1,2,4-thiadiazolyl) 1,3,4-thiadiazolyl, 4- or 5-(1,2,3-thiadiazolyl), 1,2,5-thiadiazolyl), oxazolyl (2-, 4- or 5-oxazolyl), isoxazolyl (3-, 4- or 5-isoxazolyl), oxadiazolyl (3- or 5-(1,2,4-oxadiazolyl), 1,3,4-oxadiazolyl), etc.; a 6-membered aromatic heterocyclic group containing, besides carbon atoms, 1 to 3 hetero-atoms selected from oxygen atom, sulfur atom, nitrogen atom, etc., such as pyridyl (2-, 3- or 4-pyridyl), pyrimidinyl (2-, 4- or 5-pyrimidinyl), pyridazinyl (3- or 4-pyridazinyl), pyrazinyl, triazinyl (1,2,3-triazinyl, 1,2,4-triazinyl or 1,3,5-triazinyl), thiadinyl (1,3-thiadinyl or 1,4-thiadinyl), oxazinyl (1,2-oxazinyl, 1,3-oxazinyl or 1,4-oxazinyl), etc.; etc.

Among others, a 6-membered aromatic heterocyclic group containing 1 to 3 nitrogen atoms (preferably 1 to 2 nitrogen atoms) such as pyridyl, pyrimidinyl, pyridazinyl, pyrazinyl, triazinyl, etc. is preferable. More preferable examples are pyridyl, pyrimidinyl, etc. and the most preferable example is pyridyl (preferably 4-pyridyl).

Examples of "substituents" on the "basic 5- to 7-membered aromatic heterocyclic group which may be substituted" represented by the ring $A^1$ are similar to the above-mentioned "substituents" on the "basic 5- to 7-membered heterocyclic group which may be substituted" represented by the ring A.

As the ring $A^1$, for example, a basic 6-membered heterocyclic group which may be substituted and which contains 1 to 3 nitrogen atoms (preferably 1 to 2 nitrogen atoms), such as pyridyl, pyrimidinyl, pyridazinyl, etc. is preferable. More preferable example is pyridyl (preferably 4-pyridyl).

In the above formula (I-2), the ring $A^2$ represents a piperidyl which may be substituted.

Specific examples of "piperidyl" in the "piperidyl which may be substituted" represented by the ring $A^2$ include 2-, 3- or 4-piperidyl, and 4-piperidyl is preferable.

Examples of "substituents N on the "piperidyl which may be substituted" represented by the ring $A^2$ are similar to the above-mentioned "substituents" on the "basic 5- to 7-membered heterocyclic group which may be substituted" represented by the ring A.

As the ring $A^2$, piperidyl is preferable and 4-piperidyl is more preferable.

In the above formulas (I) and (I-1), the ring B represents a divalent 5- to 7-membered nitrogen containing heterocyclic group which may be substituted or a divalent 5- to 7-membered cyclic hydrocarbon group which may be substituted.

Specific examples of "divalent 5- to 7-membered nitrogen containing heterocyclic group" in the "divalent 5- to 7-membered nitrogen containing heterocyclic group which may be substituted" represented by the ring B include a divalent 5-membered nitrogen containing heterocyclic ring which contains, besides carbon atoms, 1 to 3 nitrogen atoms, such as pyrrolediyl, pyrazolediyl, imidazolediyl, triazolediyl, pyrrolidinediyl, pyrrolinediyl, imidazolidinediyl, imidazolinediyl, pyrazolidinediyl, pyrazolinediyl, etc.; a divalent 6-membered nitrogen containing heterocyclic group which contains, besides carbon atoms, 1 to 3 nitrogen atoms, such as pyridinediyl, pyrimidinediyl, pyridazinediyl, pyrazinediyl, triazinediyl, piperidinediyl, piperazinediyl, etc.; a divalent 7-membered nitrogen containing heterocyclic group which contains, besides carbon atoms, 1 to 3 nitrogen atoms, such as azepinediyl (1-, 2-, 3- or 4-azepinediyl), diazepinediyl (1-, 2-, 4- or 5-(1,3-diazepinediyl), 1-, 2- or 5-(1,4-diazepinediyl)), etc.; etc.

Among others, a divalent 6-membered heterocyclic group containing 1 to 3 nitrogen atoms (preferably 1 to 2 nitrogen atoms) is preferable. More preferable examples are piperidinediyl, piperazinediyl, etc. and the most preferable example is piperazinediyl (preferably piperazine-1,4-diyl).

Examples of "substituents" on the "a divalent 5- to 7-membered nitrogen containing heterocyclic group which may be substituted" represented by the ring B are similar to the above-mentioned "substituents" on the "basic 5- to 7-membered heterocyclic group which may be substituted" represented by the ring A.

Specific examples of "divalent 5- to 7-membered cyclic hydrocarbon group" in the "divalent 5- to 7-membered cyclic hydrocarbon group which may be substituted" represented by the ring B include $C_{5-7}$ cycloalkylene groups (e.g. cyclopentylene, cyclohexylene, etc.); $C_{5-7}$ cycloalkenylene groups (e.g. cyclopentenylene, cyclohexenylene, etc.); phenylene; etc.

These cyclic hydrocarbon groups may have 1 to 5 substituents (preferably 1 to 2 substituents) at any possible position. Examples of the substituents include (1) $C_{1-6}$ alkyl groups (e.g. methyl, ethyl, propyl, isopropyl, butyl, sec-butyl, tert-butyl, etc.), (2) $C_{3-8}$ cycloalkyl groups (e.g. cyclopropyl, cyclobutyl, cyclopentyl, cyclohexyl, etc.), (3) $C_{2-6}$ alkenyl groups (e.g. vinyl, allyl, 2-butenyl, 3-butenyl, etc.), (4) $C_{2-6}$ alkynyl groups (e.g. ethynyl, 2-propynyl, 3-hexynyl, etc.), (5) $C_{3-8}$ cycloalkenyl groups (e.g. cyclopropenyl, cyclopentenyl, cyclohexenyl, etc.), (6) $C_{6-10}$ aryl groups (e.g. phenyl, naphthyl, etc.), (7) $C_{7-12}$ aralkyl groups (e.g. phenyl-$C_{1-6}$ alkyl groups such as benzyl, phenethyl, etc., etc.), (8) nitro group, (9) oxo group,

(10) thioxo group,

(11) cyano group,

(12) carbamoyl group,

(13) carboxyl group,

(14) $C_{1-6}$ alkoxy-carbonyl groups (e.g. methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, etc.),

(15) sulfo group,

(16) halogen atoms (e.g. fluorine, chlorine, bromine, iodine),

(17) $C_{1-4}$ alkoxy groups (e.g. methoxy, ethoxy, propoxy, isopropoxy, butoxy, isobutoxy, sec-butoxy, tert-butoxy, etc.),

(19) $C_{6-10}$ aryloxy groups (e.g. phenoxy, etc.),

(20) $C_{1-4}$ alkylthio groups (e.g. methylthio, ethylthio, propylthio, butylthio, sec-butylthio, tert-butylthio, etc.),

(21) $C_{6-10}$ arylthio groups (e.g. phenylthio, etc.),

(22) $C_{1-6}$ alkylsulfinyl groups (e.g. methylsulfinyl, ethylsulfinyl, propylsulfinyl, butylsulfinyl, etc.),

(23) $C_{6-10}$ arylsulfinyl groups (e.g. phenylsulfinyl, etc.),

(24) $C_{1-6}$ alkylsulfonyl groups (e.g. methylsulfonyl, ethylsulfonyl, propylsulfonyl, butylsulfonyl, etc.),

(25) $C_{6-10}$ arylsulfonyl groups (e.g. phenylsulfonyl, etc.),

(26) amino group,

(27) acylamino groups (e.g. $C_{1-6}$ alkanoylamino such as acetylamino, propionylamino, etc., benzoylamino, etc.),

(28) mono- or di-$C_{1-6}$ alkylamino groups (e.g. methylamino, ethylamino, propylamino, isopropylamino, butylamino, dimethylamino, diethylamino, etc.),

(29) $C_{3-8}$ cycloalkylamino groups (e.g. cyclopropylamino, cyclobutylamino, cyclopentylamino, cyclohexylamino, etc.),

(30) $C_{6-10}$ arylamino groups (e.g. anilino, etc.),

(31) $C_{1-6}$ acyl groups (e.g. $C_{1-6}$ alkanoyl group such as formyl, acetyl, propionyl, etc., etc.),

(32) $C_{6-10}$ aryl-carbonyl (e.g. benzoyl, etc.), and

(33) 5- to 6-membered heterocyclic groups containing, besides carbon atoms, 1 to 3 hetero-atoms selected from oxygen atom, sulfur atom, nitrogen atom (e.g. pyrrolyl, pyrazolyl, imidazolyl, triazolyl, pyrrolidinyl, pyrrolinyl, imidazolidinyl, imidazolinyl, pyrazolidinyl, pyrazolinyl, thienyl, thiazolyl, isothiazolyl, thiadiazolyl, furyl, oxazolyl, isoxazolyl, oxadiazolyl, pyridyl, pyrimidinyl, pyridazinyl, pyrazinyl, triazinyl (1,2,3-triazinyl, 1,2,4-triazinyl or 1,3,5-triazinyl), piperidyl, piperazinyl, pyridazinyl, pyrazinyl, thiadinyl, thiomorpholinyl, morpholinyl, pyranyl, oxazinyl, etc.), etc.

As the ring B, for example, a divalent 6-membered nitrogen containing heterocyclic group which may be substituted and which contains 1 to 3 nitrogen atoms (preferably 1 to 2 nitrogen atoms) or a phenylene group which may be substituted is preferable. Among them, phenylene, piperidinediyl, piperazinediyl, etc. are preferable and, in particular, piperazinedlyl (more preferably, piperazin-1,4-diyl), etc. are preferable.

In the above formulas (I-2), the ring $B^1$ represents a phenylene group which may be substituted.

Examples of "substituents" on the "phenylene group which may be substituted" represented by the ring $B^1$ are similar to the above-mentioned "substituents" on the "divalent 5- to 7-membered cyclic hydrocarbon group which may be substituted" represented by the ring B.

In the above formula (I), Y is an optionally substituted methylene group.

The "methylene group" in the "optionally substituted methylene group" represented by Y may have 1 or 2 substituents. Examples of the substituents include (1) halogen atoms (e.g. fluorine, chlorine, bromine, iodine), (2) a hydroxy group, (3) an oxo group, (4) $C_{1-6}$ alkoxy groups (e.g. methoxy, ethoxy, propoxy, isopropoxy, butoxy, isobutoxy, sec-butoxy, tert-butoxy, etc.), (5) di-$C_{1-6}$ alkylamino groups (e.g. dimethylamino, diethylamino, dipropylamino, etc.), (6) halogeno-$C_{1-6}$ alkyl groups (e.g. $C_{1-6}$ alkyl groups substituted with 1 to 3 halogen atoms such as chloromethyl, bromomethyl, trifluoroethyl, chloropropyl, etc., etc.), (7) $C_{1-6}$ acyl groups (e.g. $C_{1-6}$ alkanoyl group such as formyl, acetyl, propionyl, etc., etc.), (8) hydroxy-$C_{1-6}$ alkyl groups (e.g. hydroxymethyl, hydroxyethyl, hydroxypropyl, etc.), (9) $C_{1-6}$ alkoxy-$C_{1-6}$ alkyl groups (e.g. methoxymethyl, 2-ethoxyethyl, etc.), and

(10) $C_{1-6}$ alkoxy-carbonyl groups (e.g. methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, etc.), etc.

In the above formula (I-1), $Y^1$ is an optionally substituted imino group.

The "imino group" in the "optionally substituted imino group" represented by $Y^1$ may have 1 or 2 substituents. Examples of the substituents include (1) $C_{1-6}$ alkoxy groups (e.g. methoxy, ethoxy, propoxy, isopropoxy, butoxy, isobutoxy, sec-butoxy, tert-butoxy, etc.), (2) halogeno-$C_{1-6}$ alkyl groups (e.g. $C_{1-6}$ alkyl groups substituted with 1 to 3 halogen atoms such as chloromethyl, bromomethyl, trifluoroethyl, chloropropyl, etc., etc.), (3) $C_{1-6}$ acyl groups (e.g. $C_{1-6}$ alkanoyl group such as formyl, acetyl, propionyl, etc., etc.), (4) hydroxy-$C_{1-6}$ alkyl groups (e.g. hydroxymethyl, hydroxyethyl, hydroxypropyl, etc.), (5) $C_{1-6}$ alkoxy-$C_{1-6}$ alkyl groups (e.g. methoxymethyl, 2-ethoxyethyl, etc.), and (6) $C_{1-6}$ alkoxy-carbonyl groups (e.g. methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, etc.), etc.

In the above formulas (I), (I-1) and (I-2), $R^1$ is a hydrogen atom, an optionally substituted hydroxy group, an optionally substituted amino group or an optionally substituted hydrocarbon group which may be bound through a carbonyl group, a thio group, a sulfinyl group or a sulfonyl group.

Examples of "substituent" in the "optionally substituted hydroxy group" represented by $R^1$ include (1) $C_{1-6}$ alkyl groups (e.g. methyl, ethyl, propyl, isopropyl, butyl, iso-butyl, sec-butyl, tert-butyl, etc.) which may have 1 to 4 substituents selected from the class consisting of halogen atoms (e.g. chlorine, bromine, fluorine, etc.), $C_{6-10}$ aryl groups (e.g. phenyl, naphthyl, etc.), $C_{7-12}$ aralkyl groups (e.g. benzyl, phenethyl, etc.), and a nitro group, etc., (2) $C_{6-10}$ aryl groups (e.g. phenyl, naphthyl, etc.) which may have 1 to 4 substituents selected from the class consisting of halogen atoms (e.g. chlorine, bromine, fluorine, etc.), $C_{1-6}$ alkyl groups (e.g. methyl, ethyl, propyl, etc.), $C_{6-10}$ aryl groups (e.g. phenyl, naphthyl, etc.), $C_{7-12}$ aralkyl groups (e.g. phenyl-$C_{1-6}$ alkyl groups such as benzyl, phenethyl, etc., etc.), and a nitro group, etc., (3) $C_{7-12}$ aralkyl groups (e.g. phenyl-$C_{1-6}$ alkyl groups such as benzyl, phenylethyl, etc., naphtylmethyl, etc.) which may have 1 to 4 substituents selected from the class consisting of halogen atoms (e.g. chlorine, bromine, fluorine, etc.), $C_{1-6}$ alkyl groups (e.g. methyl, ethyl, propyl, etc.), $C_{6-10}$ aryl groups (e.g. phenyl, naphthyl, etc.), $C_{7-12}$ aralkyl groups (e.g. phenyl-$C_{1-6}$ alkyl groups such as benzyl, phenlethyl, etc., etc.), and a nitro group, etc., (4) a formyl group, (5) $C_{3-6}$ alkyl-carbonyl groups (e.g. $C_{1-6}$ alkanoyl group such as acetyl, propionyl, etc.) which may have 1 to 4 substituents selected from the class consisting of halogen atoms (e.g. chlorine, bromine, fluorine, etc.), $C_{1-6}$ alkyl groups (e.g. methyl, ethyl, propyl, etc.), $C_{6-10}$ aryl groups (e.g. phenyl, naphthyl, etc.), $C_{7-12}$ aralkyl groups (e.g. phenyl-$C_{1-6}$ alkyl groups such as benzyl, phenlethyl, etc., etc.), and a nitro group, etc., (6) $C_{6-10}$ aryloxy-carbonyl (e.g. phenyloxycarbonyl, naphthyloxycarbonyl, etc.) which may have 1 to 4 substituents selected from the class consisting of halogen atoms (e.g. chlorine, bromine, fluorine, etc.), $C_{1-6}$ alkyl groups (e.g. methyl, ethyl, propyl, etc.), $C_{6-10}$ aryl groups (e.g. phenyl, naphthyl, etc.), $C_{7-12}$ aralkyl groups (e.g. phenyl-$C_{1-6}$ alkyl groups such as benzyl, phenlethyl, etc., etc.), and a nitro group, etc., (7) $C_{6-10}$ aryl-carbonyl (e.g. benzoyl, naphthylcarbonyl, etc.) which may have 1 to 4 substituents selected from the class consisting of halogen atoms (e.g. chlorine, bromine, fluorine, etc.), $C_{1-6}$ alkyl groups (e.g. methyl, ethyl, propyl, etc.), $C_{6-10}$ aryl groups (e.g. phenyl, naphthyl, etc.), $C_{7-12}$ aralkyl groups (e.g. phenyl-$C_{1-6}$ alkyl groups such as benzyl, phenlethyl, etc., etc.), and a nitro group, etc., (8) 5-membered aromatic heterocyclic groups (e.g. pyranyl, furanyl, etc.) which may have 1 to 4 substituents selected from the class consisting of halogen atoms (e.g. chlorine, bromine, fluorine, etc.), $C_{1-6}$ alkyl groups (e.g. methyl, ethyl, propyl, etc.), $C_{6-10}$ aryl groups (e.g. phenyl, naphthyl, etc.), $C_{7-12}$ aralkyl groups (e.g. phenyl-$C_{1-6}$alkyl groups such as benzyl, phenlethyl, etc., etc.), and a nitro group, etc., and

(10) tri-$C_{1-4}$ alkylsilyl (e.g. trimethylsilyl, triethylsilyl, etc.), etc. Among others, $C_{1-6}$ alkyl-carbonyl groups (preferably, acetyl) are preferable.

The "amino group" in the "optionally substituted amino group" represented by $R^1$ may have 1 or 2 substituents selected from the class consisting of optionally substituted hydrocarbon groups and acyl groups, etc.

Examples of the "hydrocarbon groups" in the "optionally substituted hydrocarbon groups" as substituents of the "amino group" represented by $R^1$ include $C_{1-6}$ alkyl groups (e.g. methyl, ethyl, propyl, isopropyl, butyl, isobutyl, sec-butyl, tert-butyl, etc.), $C_{3-8}$ cycloalkyl groups (e.g. cyclopropyl, cyclobutyl, cyclopentyl, cyclohexyl, etc.), $C_{2-6}$ alkenyl groups (e.g. vinyl, allyl, 2-butenyl, 3-butenyl, etc.), $C_{2-6}$ alkynyl groups (e.g. ethynyl, 2-propynyl, 1-hexynyl, etc.), $C_{3-8}$ cycloalkenyl groups (e.g. cyclopropenyl, cyclopentenyl, cyclohexenyl, etc.), $C_{6-10}$ aryl groups (e.g. phenyl, naphthyl, etc.), $C_{7-12}$ aralkyl groups (e.g. phenyl-$C_{1-6}$ alkyl groups such as benzyl, phenlethyl, etc., etc.), etc.

These hydrocarbon groups may have 1 to 4 substituents at any possible position. Examples of the substituents include (1) nitro group, (2) hydroxy group, (3) oxo group, (4) thioxo group, (5) cyano group, (6) carbamoyl group, (7) carboxyl group, (8) $C_{1-6}$ alkoxy-carbonyl groups (e.g. methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, etc.), (9) halogen atoms (e.g. fluorine, chlorine, bromine, iodine, etc.),

(10) $C_{1-6}$ alkoxy groups (e.g. methoxy, ethoxy, propoxy, isopropoxy, butoxy, isobutoxy, sec-butoxy, tert-butoxy, etc.),

(11) phenoxy group,

(12) halogeno-phenoxy group (e.g. phenoxy substituted with 1 to 3 halogen atoms such as o-, m- or p-chlorophenoxy, o-, m- or p-bromophenoxy, etc., etc.),

(13) $C_{1-6}$ alkylthio groups (e.g. methylthio, ethylthio, propylthio, isopropylthio, butylthio, tert-butylthio, etc.),

(14) phenylthio,

(15) $C_{1-6}$ alkylsulfinyl groups (e.g. methylsulfinyl, ethylsulfinyl, propylsulfinyl, butylsulfinyl, etc.),

(16) $C_{1-6}$ alkylsulfonyl groups (e.g. methylsulfonyl, ethylsulfonyl, propylsulfonyl, butylsulfonyl, etc.),

(17) amino group,

(18) $C_{1-6}$ acylamino groups (e.g. $C_{1-6}$ alkanoylamino such as acetylamino, propionylamino, etc., etc.),

(19) mono- or di-$C_{1-6}$ alkylamino groups (e.g. methylamino, ethylamino, propylamino, isopropylamino, butylamino, dimethylamino, diethylamino, etc.),

(20) $C_{1-6}$ acyl groups (e.g. $C_{1-6}$ alkanoyl group such as formyl, acetyl, etc., etc.),

(21) benzoyl,

(22) 5- to 6-membered heterocyclic groups containing, besides carbon atoms, 1 to 3 hetero-atoms selected from oxygen atom, sulfur atom, and nitrogen atom, etc.

(e.g. pyrrolyl, pyrazolyl, imidazolyl, triazolyl, pyrrolidinyl, pyrrolinyl, imidazolidinyl, imidazolinyl, pyrazolidinyl, pyrazolinyl, thienyl, thiazolyl, isothiazolyl, thiadiazolyl, furyl, oxazolyl, isoxazolyl, oxadiazolyl, pyridyl, pyrimidinyl, pyridazinyl, pyrazinyl, triazinyl piperidyl, piperazinyl, pyridazinyl, pyrazinyl, thiadinyl, thiomorpholinyl, morpholinyl, pyranyl, oxazlnyl, etc.) which may have 1 to 4 substituents selected from the class consisting of (a) halogen atoms (e.g. fluorine, chlorine, bromine, iodine, etc.), (b) $C_{1-6}$ alkyl groups (e.g. methyl, ethyl, propyl, isopropyl, etc.), and (c) halogeno-phenoxy groups (e.g. phenoxy substituted with 1 to 3 halogen atoms such as o-, m- or p-chlorophenoxy, o-, m- or p-bromophenoxy, etc., etc.), etc., and

(23) halogeno-$C_{1-6}$ alkyl groups (e.g. $C_{1-6}$ alkyl groups substituted with 1 to 3 halogen atoms such as difluoromethyl, trifluoromethyl, trifluoroethyl, trichloroethyl, etc., etc.), etc. In addition, these hydrocarbon groups may have 1 to 4 substituents such as $C_{1-6}$ alkyl groups (e.g. methyl, ethyl, propyl, isopropyl, butyl, isobutyl, sec-butyl, tert-butyl, etc.), or $C_{3-8}$ cycloalkyl groups (e.g. cyclopropyl, cyclobutyl, cyclopentyl, cyclohexyl, etc.).

Examples of the "acyl group" as substituents of the "amino group" represented by $R^1$ include acyl groups derived from optionally substituted carboxylic acids, optionally substituted oxycarboxylic acids, optionally substituted sulfonic acids, optionally substituted sulfinic acids, etc. In particular, a group of the formula:

$$R^4CO-, R^5OCO-, R^6SO_2- \text{ or } R^7SO-$$

[wherein $R^4$, $R^5$, $R^6$ and $R^7$ are independently an optionally substituted hydrocarbon group or an optionally substituted heterocyclic group.], etc. are exemplified.

In the above formula, $R^4$, $R^5$, $R^6$ and $R^7$ are independently an optionally substituted hydrocarbon group or an optionally substituted heterocyclic group.

Examples of the "optionally substituted hydrocarbon group" represented by $R^4$, $R^5$, $R^6$ and $R^7$ are similar to the above-mentioned "optionally substituted hydrocarbon group" as substituents of the "amino group" represented by $R^1$.

Examples of the "optionally substituted heterocyclic group" represented by $R^4$, $R^5$, $R^6$ and $R^7$ are similar to the above-mentioned "5- to 7-membered heterocyclic group which may be substituted" in the "basic 5- to 7-membered heterocyclic group which may be substituted" represented by the ring A.

Specific examples of the "optionally substituted amino group" represented by $R^1$ include amino groups optionally substituted with $C_{1-6}$ acyl groups (e.g. $C_{1-6}$ alkanoyl group such as formyl, etc., etc.), mono-$C_{1-6}$ alkylamino groups (e.g. methylamino, ethylamino, propylamino, isopropylamino, butylamino, etc.), di-$C_{1-6}$ alkylamino groups (e.g. dimethylamino, diethylamino, dipropylamino, diisopropylamino, dibutylamino, etc.), $C_{1-6}$ alkoxy-carbonylamino groups (e.g. methoxy-carbonylamino, ethoxy-carbonylamino, propoxy-carbonylamino, isopropoxy-carbonylamino, butoxy-carbonylamino, etc.), $C_{1-6}$ alkylthio-carbonylamino groups (e.g. methylthio-carbonylamino, ethylthio-carbonylamino, propylthio-carbonylamino, butylthio-carbonylamino, etc.), $C_{7-12}$ aralkylamino groups (e.g. benzylamino, etc.) which may have 1 to 3 substituents selected from the class consisting of halogen atoms (e.g. chlorine, bromine, fluorine, etc.), $C_{1-6}$ alkyl groups (e.g. methyl, ethyl, propyl, isopropyl, butyl, etc.), $C_{1-6}$ alkoxy groups (e.g. methoxy, ethoxy, propoxy, isopropoxy, butoxy, etc.), etc., benzoylamino which may have 1 to 3 substituents selected from the class consisting of halogen atoms (e.g. chlorine, bromine, fluorine, etc.), $C_{1-6}$ alkyl groups (e.g. methyl, ethyl, propyl, isopropyl, butyl, etc.), $C_{1-6}$ alkoxy groups (e.g. methoxy, ethoxy, propoxy, isopropoxy, butoxy, etc.), etc., benzenesulfonylamino which may have 1 to 3 substituents selected from the class consisting of halogen atoms (e.g. chlorine, bromine, fluorine, etc.), $C_{1-6}$ alkyl groups (e.g. methyl, ethyl, propyl, isopropyl, butyl, etc.), $C_{1-6}$ alkoxy groups (e.g. methoxy, ethoxy, propoxy, isopropoxy, butoxy, etc.), etc., optionally substituted $C_{1-6}$ alkoxy-carbonylamino groups (e.g. $C_{1-6}$ alkoxy-carbonylamino groups optionally substituted with $C_{1-6}$ alkanoyloxy, benzoyloxy, $C_{1-6}$ alkoxy-carbonyloxy, $C_{3-8}$ cycloalkyl-oxycarbonyloxy, $C_{3-8}$ cycloalkyl-carbonyloxy, 6-membered aromatic heterocyclic group-carbonyloxy or 5-methyl-2-oxo-1,3-dioxolan-4-yl, etc. such as methoxycarbonylamino, 1-(acetoxy)ethoxy-carbonylamino, pyridylcarbonyl-oxymethoxycarbonylamino, pivaloyloxymethoxy-carbonylamino, 1-(cyclohexyloxy-carbonyloxy)ethoxycarbonylamino, acetyloxymethoxycarbonylamino, propionyloxymethoxycarbonylamino, n-butyryloxymethoxycarbonylamino, isobutyryloxy-methoxycarbonylamino, 1-(ethoxycarbonyloxy) ethoxycarbonylamino, 1-(isobutyryloxy) ethoxycarbonylamino, cyclohexylcarbonyloxy-methoxycarbonylamino, benzoyloxymethoxy-carbonylamino, 5-methyl-2-oxo-1,3-dioxolan-4-yl-methoxycarbonylamino, etc.), etc.

Examples of the "optionally substituted hydrocarbon group" in the "optionally substituted hydrocarbon group" which may be bound through a carbonyl group, a thio group, a sulfinyl group or a sulfonyl group" represented by $R^1$ are similar to the above-mentioned "optionally substituted hydrocarbon group" as substituents of the "amino group" represented by $R^1$.

Specific examples of the "optionally substituted hydrocarbon group which may be bound through a carbonyl group, a thio group, a sulfinyl group or a sulfonyl group" represented by $R^1$ include $C_{1-6}$ alkyl-carbonyl groups (e.g. methylcarbonyl, ethylcarbonyl, propylcarbonyl, isopropylcarbonyl, butylcarbonyl, etc.), $C_{1-6}$ alkylthio groups (e.g. methylthio, ethylthio, propylthio, isopropylthio, butylthio, etc.), $C_{1-6}$ alkylsulfinyl groups (e.g. methylsulfinyl, ethylsulfinyl, propylsulfinyl, isopropylsulfinyl, butylsulfinyl, etc.), $C_{1-6}$ alkylsulfonyl groups (e.g. methylsulfonyl, ethylsulfonyl, propylsulfonyl, isopropylsulfonyl, butylsulfonyl, etc.), benzoyl which may have 1 to 3 substituents selected from the class consisting of halogen atoms (e.g. chlorine, bromine, fluorine, etc.), $C_{1-6}$ alkyl groups (e.g. methyl, ethyl, propyl, isopropyl, butyl, etc.), $C_{1-6}$ alkoxy groups (e.g. methoxy, ethoxy, propoxy, isopropoxy, butoxy, etc.), etc.

phenylthio which may have 1 to 3 substituents selected from the class consisting of halogen atoms (e.g. chlorine, bromine, fluorine, etc.), $C_{1-6}$ alkyl groups (e.g. methyl, ethyl, propyl, isopropyl, butyl, etc.), $C_{1-6}$ alkoxy groups (e.g. methoxy, ethoxy, propoxy, isopropoxy, butoxy, etc.), etc., phenylsulfinyl which may have 1 to 3 substituents selected from the class consisting of halogen atoms (e.g. chlorine, bromine, fluorine, etc.), $C_{1-6}$ alkyl groups (e.g. methyl, ethyl, propyl, isopropyl, butyl, etc.), $C_{1-6}$ alkoxy groups (e.g. methoxy, ethoxy, propoxy, isopropoxy, butoxy, etc.), etc., phenylsulfonyl which may have 1 to 3 substituents selected from the class consisting of halogen atoms (e.g. chlorine, bromine, fluorine, etc.), $C_{1-6}$ alkyl groups (e.g. methyl, ethyl, propyl, isopropyl, butyl, etc.), $C_{1-6}$ alkoxy groups (e.g. methoxy, ethoxy, propoxy, isopropoxy, butoxy, etc.), etc., $C_{7-12}$ aralkyl-carbonyl groups (e.g. phenyl-$C_{1-6}$ alkylcarbonyl groups such as benzylcarbonyl, etc., etc.) which may have 1 to 3 substituents selected from the class consisting of halogen atoms (e.g. chlorine, bromine, fluorine, etc.), $C_{1-6}$ alkyl groups (e.g. methyl, ethyl, propyl, isopropyl, butyl, etc.), $C_{1-6}$ alkoxy groups (e.g. methoxy, ethoxy, propoxy, isopropoxy, butoxy, etc.), etc., $C_{7-12}$ aralkylthio groups (e.g. phenyl-$C_{1-6}$ alkylthio groups such as benzylthio, etc., etc.) which may have 1 to 3 substituents selected from the class consisting of halogen atoms (e.g. chlorine, bromine, fluorine, etc.), $C_{1-6}$ alkyl groups (e.g. methyl, ethyl, propyl, isopropyl, butyl, etc.), $C_{1-6}$ alkoxy groups (e.g. methoxy, ethoxy, propoxy, isopropoxy, butoxy, etc.), etc., $C_{7-12}$ aralkylsulfinyl groups (e.g. phenyl-$C_{1-6}$ alkylsulfinyl groups such as benzylsulfinyl, etc., etc.) which may have 1 to 3 substituents selected from the class consisting of halogen atoms (e.g. chlorine, bromine, fluorine, etc.), $C_{1-6}$ alkyl groups (e.g. methyl, ethyl, propyl, isopropyl, butyl, etc.), $C_{1-6}$ alkoxy groups (e.g. methoxy, ethoxy, propoxy, isopropoxy, butoxy, etc.), etc., $C_{7-12}$ aralkylsulfonyl groups (e.g. phenyl-$C_{1-6}$ alkylsulfonyl groups such as benzylsulfonyl, etc., etc.) which may have 1 to 3 substituents selected from the class consisting of halogen atoms (e.g. chlorine, bromine, fluorine, etc.), $C_{1-6}$ alkyl groups (e.g. methyl, ethyl, propyl, isopropyl, butyl, etc.), $C_{1-6}$ alkoxy groups (e.g. methoxy, ethoxy, propoxy, isopropoxy, butoxy, etc.), etc., $C_{1-6}$ alkyl groups (e.g. methyl, ethyl, propyl, isopropyl, butyl, etc.) optionally substituted with a $C_{6-10}$ aryl group (e.g. phenyl, naphthyl, etc.) which may have 1 to 3 substituents selected from the class consisting of halogen atoms (e.g. chlorine, bromine, fluorine, etc.), $C_{1-6}$ alkyl groups (e.g. methyl, ethyl, propyl, isopropyl, butyl, etc.), $C_{1-6}$ alkoxy groups (e.g. methoxy, ethoxy, propoxy, isopropoxy, butoxy, etc.), etc., etc.

As the group $R^1$, a hydrogen atom, an optionally substituted hydroxy group, an optionally substituted lower alkyl group and an optionally substituted amino group are preferable.

In the above formulas (I), (I-1) and (I-2), $R^2$ is a hydrogen atom or an optionally substituted hydrocarbon group.

Examples of the "optionally substituted hydrocarbon represented by $R^2$ are similar to the above-mentioned "optionally substituted hydrocarbon group" as substituents of the "amino group" represented by $R^1$.

As the group shown by $R^2$, hydrogen atom is preferable.

In the above formulas (I), (I-1) and (I-2), $R^3$ is an optionally esterified or amidated carboxyl group.

As the "optionally esterified or amidated carboxyl group" represented by $R^3$, a carboxyl group or a group convertible to a substituent of an physiologically active compound in a living body when the compounds (I), (I-1) and (I-2) are administered as a pro-drug is preferable. Examples of the "optionally esterified or amidated carboxyl group" include a group of the formula:

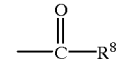

[wherein $R^8$ is a hydroxy group, a $C_{1-6}$ alkoxy group, a $C_{3-8}$ alkenyloxy group, a $C_{7-12}$ aralkyloxy group, or an optionally substituted amino group], etc.

As the "$C_{1-6}$ alkoxy group" represented by $R^8$, for example, methoxy, ethoxy, propoxy, butoxy, etc. are used.

As the "$C_{2-8}$ alkenyloxy" represented by $R^8$, for example, allyloxy, butenyloxy, etc. are used.

As the "$C_{7-12}$ aralkyloxy group" represented by $R^8$, for example, benzyloxy, phenethyloxy, 3-phenylpropyloxy, etc. are used.

As the "optionally substituted amino group" represented by $R^8$, for example, a group of the formula:

etc. are used.

In the formula:

$R^9$ and $R^{10}$ are the same or different a hydrogen atom, a $C_{1-6}$ alkyl group (e.g. methyl, ethyl, propyl, butyl, hexyl, etc.), a $C_{2-8}$ alkenyl group (e.g. allyl, 2-butenyl, 3-pentenyl, etc.), or a $C_{7-12}$ aralkyl group (e.g. benzyl, phenethyl, phenylpropyl, etc.), and, the aryl group (e.g. phenyl) in the aralkyl group may be unsubstituted or optionally substituted with one or two substituents as exemplified by a nitro group, a halogen atom (e.g. chlorine, fluorine, bromine, etc.), a $C_{1-6}$ alkyl group (e.g. methyl, ethyl, propyl, etc.) and a $C_{1-6}$ alkoxy group (e.g. methoxy, ethoxy, propoxy, etc.).

When the compounds (I), (I-1) and (I-2) are used as a pro-drug suitable for oral administration, preferable examples of Re include a hydroxy group, an optionally substituted amino group (e.g. amino, mono-$C_{1-6}$ alkylamino, di-$C_{1-6}$ alkylamino, etc.) or an optionally substituted $C_{1-6}$ alkoxy group [e.g. $C_{1-6}$ alkoxy groups optionally substituted with 1 to 3 substituents selected from the class consisting of a hydroxy group, an optionally substituted amino (e.g. amino, mono-$C_{1-6}$ alkylamino, di-$C_{1-6}$ alkylamino, cyclic amino such as piperidino and morpholino, etc., etc.), a halogen atom (e.g. chloro, fluoro, bromo, etc.), $C_{1-6}$ alkoxy (e.g. methoxy, ethoxy, propoxy, etc.), $C_{1-6}$ alkylthio (e.g. methylthio, etc.), $C_{1-6}$ alkoxy-carbonyl (e.g. methoxycarbonyl, ethoxycarbonyl, propoxycarbonyl, t-butyloxycarbonyl, etc.), propylidene, 3-phthalidylidene, and an optionally substituted dioxolenyl (e.g. 5-methyl-2-oxo-1,3-dioxolan-4-yl, etc.)], etc.; or a group of the formula:

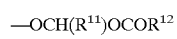

in which $R^{11}$ is hydrogen, a straight-chain or branched $C_{1-6}$ alkyl group, or a $C_{5-7}$ cycloalkyl group, and $R^{12}$ is i) a straight-chain or branched $C_{1-6}$ alkyl group, a $C_{2-8}$ alkenyl group, a $C_{5-7}$ cycloalkyl group or a $C_{1-3}$ alkyl group substituted with $C_{5-7}$ cycloalkyl or $C_{6-10}$ aryl, ii) a $C_{2-3}$ alkenyl group substituted with $C_{5-7}$ cycloalkyl or $C_{6-10}$ aryl, iii) an optionally substituted $C_{6-10}$ aryl group, a straight-chain or branched $C_{1-6}$ alkoxy group, a straight-chain or branched $C_{2-8}$ alkenyloxy group, a $C_{5-7}$ cycloalkyloxy group, a $C_{1-3}$ alkoxy group substituted with $C_{5-7}$ cycloalkyl group or optionally substituted $C_{6-10}$ aryl, iv) a $C_{2-3}$ alkenyloxy group substituted with $C_{5-7}$ cycloalkyl group or optionally substituted $C_{6-10}$ aryl, or v) an optionally substituted $C_{6-10}$ aryloxy group, and the aryl moiety in the group $R^{12}$ may have 1 to 3 substituents selected from the class consisting of a halogen atom, a nitro group and a $C_{1-6}$ alkyl group.

Examples of the "straight-chain or branched $C_{1-6}$ alkyl group" represented by $R^{11}$ include methyl, ethyl, n-propyl, isopropyl, n-butyl, isobutyl, t-butyl, n-pentyl, isopentyl, neopentyl, etc. and examples of the "$C_{5-7}$ cycloalkyl group" represented by $R^{11}$ include cyclopentyl, cyclohexyl, cycloheptyl, etc.

Specific examples of $R^{12}$ include, as the above-mentioned i), a straight-chain or branched $C_{1-6}$ alkyl group (e.g. methyl, ethyl, n-propyl, isopropyl, n-butyl, isobutyl, sec-butyl, t-butyl, n-pentyl, isopentyl, neopentyl, etc.), a $C_{2-8}$ alkenyl group (e.g. vinyl, propenyl, allyl, isopropenyl, etc.), a $C_{5-7}$ cycloalkyl group (e.g. cyclopentyl, cyclohexyl, cycloheptyl, etc.), a $C_{1-3}$ alkyl group substituted with $C_{5-7}$ cycloalkyl (e.g. cyclopentyl, cyclohexyl, cycloheptyl, etc.) or $C_{6-10}$ aryl (e.g. phenyl, etc.) such as benzyl, p-chlorobenzyl, phenethyl, cyclopentylmethyl, cyclohexylmethyl, etc.);

as the above-mentioned ii), a $C_{2-3}$ alkenyl group substituted with $C_{5-7}$ cycloalkyl (e.g. cyclopentyl, cyclohexyl, cycloheptyl) or $C_{6-10}$ aryl (e.g. phenyl, etc.) such as cinnamyl, etc. having alkenyl moiety such as vinyl, propenyl, allyl, isopropenyl, etc.;

as the above-mentioned iii), a $C_{6-10}$ aryl group optionally substituted with 1 to 3 $C_{1-6}$ alkyl groups (e.g. phenyl, p-tolyl, naphthyl, etc.), a straight-chain or branched $C_{1-6}$ alkoxy group (e.g. methoxy, ethoxy, n-propoxy, isopropoxy, n-butoxy, isobutoxy, sec-butoxy, t-butoxy, n-pentyloxy, isopentyloxy, neopentyloxy, etc.), a straight-chain or branched $C_{2-8}$ alkenyloxy group (e.g. allyloxy, isobutenyloxy, etc.), a $C_{5-7}$ cycloalkyloxy group (e.g. cyclopentyloxy, cyclohexyloxy, cycloheptyloxy, etc.), a $C_{1-3}$ alkoxy group substituted with $C_{5-7}$ cycloalkyl (e.g. cyclopentyl, cyclohexyl, cycloheptyl) or $C_{6-10}$ aryl optionally substituted with 1 to 3 $C_{1-6}$ alkyl groups (e.g. phenyl, etc.) such as benzyloxy, phenethyloxy, cyclopentylmethyloxy, cyclohexylmethyloxy, etc. having alkoxy moiety such as methoxy, ethoxy, n-propoxy, isopropoxy, etc.;

as the above-mentioned iv), a $C_{2-3}$ alkenyloxy group substituted with $C_{5-7}$ cycloalkyl (e.g. cyclopentyl, cyclohexyl, cycloheptyl, etc.) or $C_{6-10}$ aryl optionally substituted with 1 to 3 $C_{1-6}$ alkyl groups (e.g. phenyl, etc.) such as cinnamyloxy, etc. having alkenyloxy moiety such as vinyloxy, propenyloxy, allyloxy, isopropenyloxy, etc.; or as the above-mentioned v), a $C_{6-10}$ aryloxy group optionally substituted with 1 to 3 $C_{1-6}$ alkyl or nitro groups (e.g. phenoxy, p-nitrophenoxy, naphthoxy, etc.), etc.

Among others, preferable examples of the "optionally sterified carboxyl group" as $R^3$, when the compounds (I), (I-1) and (I-2) are used as a pro-drug, include ethoxycarbonyl, ethoxycarbonyl, t-butoxycarbonyl, propoxycarbonyl, pivaloyloxymethoxycarbonyl, 1-(cyclohexyloxycarbonyloxy)ethoxycarbonyl, 5-methyl-2-oxo-1,3-dioxolan-4-ylmethoxycarbonyl, acetoxymethyloxycarbonyl, propionyloxymethoxycarbonyl, n-butyryloxymethoxycarbonyl, isobutyryloxymethoxycarbonyl, 1-(ethoxycarbonyloxy)ethoxycarbonyl, 1-(acetyloxy)ethyloxycarbonyl, 1-(isobutyryloxy)ethoxycarbonyl, cyclohexylcarbonyloxymethoxycarbonyl, benzoyloxymethoxycarbonyl, cinnamyloxycarbonyl, cyclopentylcarbonyloxymethoxycarbonyl, N,N-dimethylaminocarbonyl, 2-(isobutyryloxycarbonyl)-2-propylideneethoxycarbonyl, 3-(phthalidylidene)ethoxycarbonyl, etc.

As $R^3$, a carboxyl group or a group convertible thereinto in a living body is preferable. Among others, a $C_{1-6}$ alkoxycarbonyl group (e.g. methoxy-carbonyl, ethoxycarbonyl, propoxycarbonyl, tert-butyloxy-carbonyl, etc.) is preferable.

In the above formulas (I), (I-1) and (I-2), D is a lower alkyl group substituted with an optionally esterified carboxyl group.

Examples of the "lower alkyl group" in the "lower alkyl group substituted with an optionally esterified carboxyl group" represented by D include a $C_{1-6}$ alkyl group (e.g. methyl, ethyl, propyl, isopropyl, isobutyl, sec-butyl, t-butyl, etc.).

Examples of the "optionally esterified carboxyl group" as substituents of "lower alkyl group substituted with an optionally esterified carboxyl group" represented by D are similar to the "optionally esterified carboxyl group" in the above-mentioned "optionally esterified or amidated carboxyl group" represented by $R^3$.

Examples of the "optionally esterified carboxyl group" include a group of the formula:

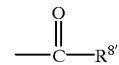

[wherein $R^{8'}$ has the same meaning as the above-mentioned $R^8$, provided that $R^{8'}$ is not an optionally substituted amino group], etc.

As D, a lower alkoxycarbonyl-lower alkyl group (e.g. a $C_{1-6}$ alkoxy-carbonyl-$C_{1-6}$ alkyl group etc., such as methoxy-carbonylmethyl, methoxy-carbonylethyl, ethoxycarbonylmethyl, ethoxycarbonylethyl, etc.) is preferable.

Among the compound (I), a compound of the formula (I) wherein the ring A is pyridyl, pyrimidinyl or piperidyl; the ring B is phenylene, piperidinediyl or piperazinediyl;

Y is a methylene group;

$R^1$ is (A) a hydrogen atom, (B) a hydroxy group optionally substituted with a $C_{1-6}$ alkyl-carbonyl group, (C) an amino group optionally substituted with one or two substituents selected from the class consisting of (1) a formyl group, (2) $C_{2-6}$ alkanoyl group, (3) a $C_{1-6}$ alkyl group, (4) a $C_{1-6}$ alkoxy-carbonyl group, (5) a $C_{1-6}$ alkylthio-carbonyl group, (6) a $C_{7-12}$ aralkyl group which may have 1 to 3 substituents selected from the class consisting of a halogen atom, a $C_{1-6}$ alkyl group and a $C_{1-6}$ alkoxy group, (7) a benzoyl group which may have 1 to 3 substituents selected from the class consisting of a halogen atom, a $C_{1-6}$ alkyl group and a $C_{1-6}$ alkoxy group, (8) a benzenesulfonyl group which may have 1 to 3 substituents selected from the class consisting of a halogen atom, a $C_{1-6}$ alkyl group and a $C_{1-6}$ alkoxy group, and (9) a $C_{1-6}$ alkoxy-carbonyl group which may be substituted with $C_{1-6}$ alkanoyloxy, benzoyloxy, $C_{1-6}$ alkoxy-carbonyloxy, $C_{3-8}$ cycloalkyloxy-carbonyloxy, $C_{3-8}$ cycloalkyl-carbonyloxy, pyridyl-carbonyloxy or 5-methyl-2-oxo-1,3-dioxolan-4-yl, or (D) a $C_{1-6}$ alkyl group optionally substituted with a $C_{6-10}$ aryl group which may have 1 to 3 substituents selected from the class consisting of a halogen atom, a $C_{1-6}$ alkyl group and a $C_{1-6}$ alkoxy group;

$R^2$ is a hydrogen atom;

$R^3$ is a carboxyl group or a $C_{1-6}$ alkoxy-carbonyl group; and

D is a $C_{1-6}$ alkoxy-carbonyl-$C_{1-6}$ alkyl group; or a salt thereof is preferable.

Among the compound (I-1), a compound of the formula (I-1) wherein the ring $A^1$ is pyridyl or pyrimidinyl;

the ring B is phenylene, piperidinediyl or piperazinediyl;

$Y^1$ is an imino group;

$R^1$ is (A) a hydrogen atom, (B) a hydroxy group optionally substituted with a $C_{1-6}$ alkyl-carbonyl group, (C) an amino group optionally substituted with one or two substituents selected from the class consisting of (1) a formyl group, (2) $C_{2-6}$ alkanoyl group, (3) a $C_{1-6}$ alkyl group, (4) a $C_{1-6}$ alkoxy-carbonyl group, (5) a $C_{1-6}$ alkylthio-carbonyl group, (6) a $C_{7-12}$ aralkyl group which may have 1 to 3 substituents selected from the class consisting of a halogen atom, a $C_{1-6}$ alkyl group and a $C_{1-6}$ alkoxy group, (7) a benzoyl group which may have 1 to 3 substituents selected from the class consisting of a halogen atom, a $C_{1-6}$ alkyl group and a $C_{1-6}$ alkoxy group, (8) a benzenesulfonyl group which may have 1 to 3 substituents selected from the class consisting of a halogen atom, a $C_{1-6}$ alkyl group and a $C_{1-6}$ alkoxy group, and (9) a $C_{1-6}$ alkoxy-carbonyl group which may be substituted with $C_{1-6}$ alkanoyloxy, benzoyloxy, $C_{1-6}$ alkoxy-carbonyloxy, $C_{3-8}$ cycloalkyloxy-carbonyloxy, $C_{3-8}$ cycloalkyl-carbonyloxy, pyridyl-carbonyloxy or 5-methyl-2-oxo-1,3-dioxolan-4-yl, or (D) a $C_{1-6}$ alkyl group optionally substituted with a $C_{6-10}$ aryl group which may have 1 to 3 substituents selected from the class consisting of a halogen atom, a $C_{1-6}$ alkyl group and a $C_{1-6}$ alkoxy group;

$R^2$ is a hydrogen atom;

$R^3$ is a carboxyl group or a $C_{1-6}$ alkoxy-carbonyl group; and

D is a $C_{1-6}$ alkoxy-carbonyl-$C_{1-6}$ alkyl group; or a salt thereof is preferable. In particular, a compound of the formula (I-1) wherein the ring $A^1$ is pyridyl; the ring B is phenylene or piperidinediyl; $Y^1$ is an imino group; $R^1$ is (A) a hydrogen atom or (B) a $C_{1-6}$ alkyl group optionally substituted with a $C_{6-10}$ aryl group which may have a $C_{1-6}$ alkoxy group; $R^2$ is a hydrogen atom; $R^3$ is a carboxyl group or a $C_{1-6}$ alkoxy-carbonyl group; and D is a $C_{1-6}$ alkoxy-carbonyl-$C_{1-6}$ alkyl group; or a salt thereof is preferable.

Among the compound (I-2), a compound of the formula (I-2) wherein the ring $A^2$ is piperidyl;

the ring $B^1$ is phenylene;

$Y^1$ is an imino group;

$R^1$ is (A) a hydrogen atom, (B) a hydroxy group optionally substituted with a $C_{1-6}$ alkyl-carbonyl group, (C) an amino group optionally substituted with one or two substituents selected from the class consisting of (1) a formyl group, (2) $C_{2-6}$ alkanoyl group, (3) a $C_{1-6}$ alkyl group, (4) a $C_{1-6}$ alkoxy-carbonyl group, (5) a $C_{1-6}$ alkylthio-carbonyl group, (6) a $C_{7-12}$ aralkyl group which may have 1 to 3 substituents selected from the class consisting of a halogen atom, a $C_{1-6}$ alkyl group and a $C_{1-6}$ alkoxy group, (7) a benzoyl group which may have 1 to 3 substituents selected from the class consisting of a halogen atom, a $C_{1-6}$ alkyl group and a $C_{1-6}$ alkoxy group, (8) a benzenesulfonyl group which may have 1 to 3 substituents selected from the class consisting of a halogen atom, a $C_{1-6}$ alkyl group and a $C_{1-6}$ alkoxy group, and (9) a $C_{1-6}$ alkoxy-carbonyl group which may be substituted with $C_{1-6}$ alkanoyloxy, benzoyloxy, $C_{1-6}$ alkoxy-carbonyloxy, $C_{3-8}$ cycloalkyloxy-carbonyloxy, $C_{3-8}$ cycloalkyl-carbonyloxy, pyridyl-carbonyloxy or 5-methyl-2-oxo-1,3-dioxolan-4-yl, or (D) a $C_{1-6}$ alkyl group optionally substituted with a $C_{6-10}$ aryl group which may have 1 to 3 substituents selected from the class consisting of a halogen atom, a $C_{1-6}$ alkyl group and a $C_{1-6}$ alkoxy group;

$R^2$ is a hydrogen atom;

$R^3$ is a carboxyl group or a $C_{1-6}$ alkoxy-carbonyl group; and

D is a $C_{1-6}$ alkoxy-carbonyl-$C_{1-6}$ alkyl group; or a salt thereof is preferable. In particular, a compound of the formula (I-2) wherein the ring $A^2$ is piperidyl; the ring $B^1$ is phenylene; $Y^1$ is an imino group; $R^1$ is (A) a hydrogen atom or (B) a $C_{1-6}$ alkyl group optionally substituted with a $C_{6-10}$ aryl group which may have a $C_{1-6}$ alkoxy group; $R^2$ is a hydrogen atom; $R^3$ is a carboxyl group or a $C_{1-6}$ alkoxy-carbonyl group; and D is a $C_{1-6}$ alkoxy-carbonyl-$C_{1-6}$ alkyl group; or a salt thereof is preferable.

Among others, (S,S)-[4-[2-(4-methoxybenzenesulfonylamino)-4-oxo-(4-pyridin-4-yl-piperazin-1-yl)butyryl]-3-methoxycarbonylmethyl-2-oxo-piperazin-1-yl] acetic acid, (S,S)-[4-[2-(4-methoxy-benzylamino)-4-oxo-(4-pyridin-4-ylpiperazin-1-yl)-butyryl]-3-methoxy-carbonylmethyl-2-oxo-piperazin-1-yl]-acetic acid, or a pharmaceutically acceptable salt thereof; is preferable.

The compounds (I) of this invention can be produced by, for example, methods as described below or those similar to the methods described below.

a) The compounds (I) of this invention can be produced by subjecting a compound (II) of the formula:

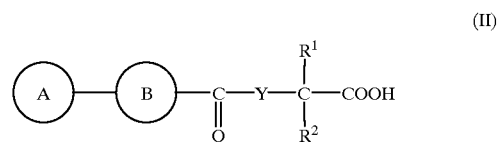

(II)

wherein each symbol is of the same meaning as defined above, or a salt thereof and a compound (III) of the formula:

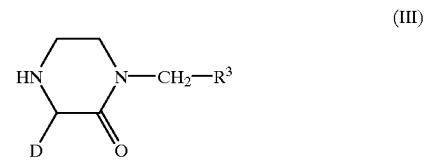

(III)

wherein each symbol is of the same meaning as defined above, or a salt thereof to condensation reaction.

The compounds (I-1) of this invention can be produced by, for example, methods as described below or those similar to the methods described below.

a-1) The compounds (I-1) of this invention can be produced by subjecting a compound (II-1) of the formula:

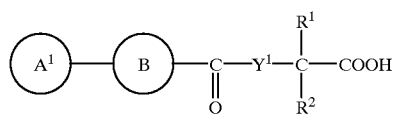 (II-1)

wherein each symbol is of the same meaning as defined above, or a salt thereof and a compound (III) of the formula:

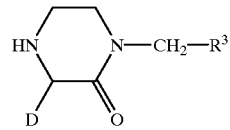 (III)

wherein each symbol is of the same meaning as defined above, or a salt thereof to condensation reaction.

The compounds (I-2) of this invention can be produced by, for example, methods as described below or those similar to the methods described below.

a-2) The compounds (I-2) of this invention can be produced by subjecting a compound (II-2) of the formula:

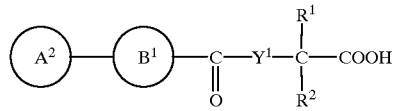 (II-2)

wherein each symbol is of the same meaning as defined above, or a salt thereof and a compound (III) of the formula:

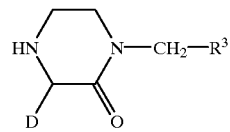 (III)

wherein each symbol is of the same meaning as defined above, or a salt thereof to condensation reaction.

In addition, b) the compounds (I-1) can be produced by subjecting a compound (IV) of the formula:

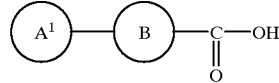 (IV)

wherein each symbol is of the same meaning as defined above, or a salt thereof and a compound (V) of the formula:

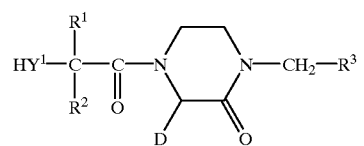 (V)

wherein each symbol is of the same meaning as defined above, or a salt thereof to condensation reaction.

In addition, c) the compounds (I) wherein the ring B is an optionally substituted piperazinedlyl group can be produced by subjecting a compound (VI) of the formula:

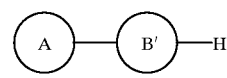 (VI)

wherein B' is an optionally substituted piperazinediyl group and the other symbols are of the same meaning as defined above, or a salt thereof and a compound (VII) of the formula:

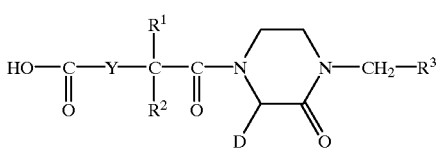 (VII)

wherein each symbol is of the same meaning as defined above, or a salt thereof to condensation reaction.

The compounds (I) wherein $R^1$ is an optionally substituted amino group can be produced by the following method:

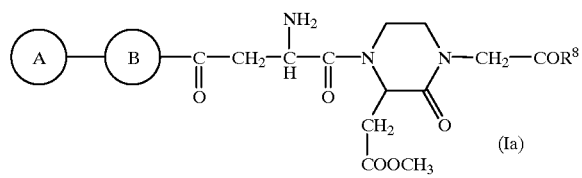

(Ia)

[wherein each symbol is as defined above]

↓ acylation

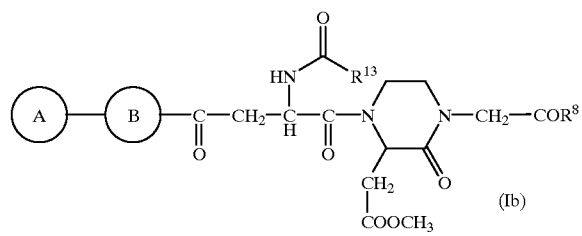

(Ib)

wherein $R^{13}$ is $C_{1-6}$ alkyl group, $C_{7-12}$ aralkyl group, $C_{1-6}$ alkoxy group or $C_{1-6}$ alkylthio group, and the other symbols are of the same meaning as defined above.

Compound (Ib)

↓ $R^{14}SO_2Cl$

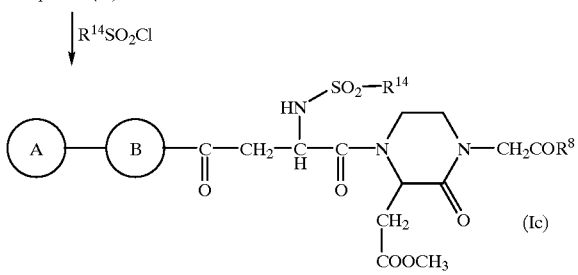

wherein $R^{14}$ is $C_{1-6}$ alkyl group, $C_{7-12}$ aralkyl group or $C_{6-10}$ aryl group, and the other symbols are of the same meaning as defined above.

Compound (Ib)

$NaBH_3CN$ ↓ $R^{15}CHO$

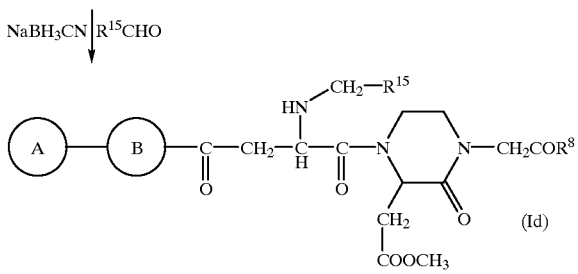

wherein $R^{15}$ is $C_{1-6}$ alkyl group, $C_{7-12}$ aralkyl group or $C_{6-10}$ aryl group, and the other symbols are of the same meaning as defined above.

Compound (Id)

$NaBH_3CN$ ↓ $R^{16}CHO$

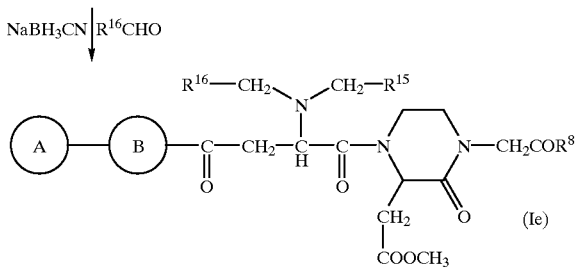

wherein $R^{16}$ is $C_{1-6}$ alkyl group, $C_{7-12}$ aralkyl group or $C_{6-10}$ aryl group, and the other symbols are of the same meaning as defined above.

In the above formula (Ib), examples of $C_{1-6}$ alkyl group represented by $R^{13}$ include methyl, ethyl, propyl, isopropyl, butyl, isobutyl, tert-butyl, sec-butyl, etc.

In the above formula (Ib), examples of $C_{7-12}$ aralkyl group represented by $R^{13}$ include phenyl-$C_{1-6}$ alkyl group such as benzyl, phenethyl, etc., etc.

In the above formula (Ib), examples of $C_{1-6}$ alkoxy group represented by $R^{13}$ include methoxy, ethoxy, propoxy, isopropoxy, butoxy, isobutoxy, tert-butoxy, sec-butoxy, etc.

In the above formula (Ib), examples of $C_{1-6}$ alkylthio group represented by $R^{13}$ include methylthio, ethylthio, propylthio, isopropylthio, butylthio, isobutylthio, tert-butylthio, sec-butylthio, etc.

In the above formula (Ic), examples of $C_{1-6}$ alkyl group and $C_{7-12}$ aralkyl group represented by $R^{14}$ are similar to the above-mentioned $C_{1-6}$ alkyl group and $C_{7-12}$ aralkyl group represented by $R^{13}$.

In the above formula (Ic), examples of $C_{6-10}$ aryl group represented by $R^{14}$ include phenyl, naphthyl, etc.

In the above formula (Id), examples of $C_{1-6}$ alkyl group, $C_{7-12}$ aralkyl group and $C_{6-10}$ aryl group represented by $R^{15}$ are similar to the above-mentioned $C_{1-6}$ alkyl group, $C_{7-12}$ aralkyl group and $C_{6-10}$ aryl group represented by $R^{14}$.

In the above formula (Ie), examples of $C_{1-6}$ alkyl group, $C_{7-12}$ aralkyl group and $C_{6-10}$ aryl group represented by $R^{16}$ are similar to the above-mentioned $C_{1-6}$ alkyl group, $C_{7-12}$ aralkyl group and $C_{6-10}$ aryl group represented by $R^{14}$.

The condensation reaction in the methods a), a-1), a-2), b) and c) as the methods for producing the compounds (I), (I-1) and (I-2) of this invention can be carried out by an amide-linkage formation reaction in a conventional peptide synthesis, for example, the method using active ester, mixed acid anhydride or acid chloride.

For example, the condensation reaction between the compound (II) and the compound (III), the compound (II-1) and the compound (III), the compound (II-2) and the compound (III), the compound (IV) and the compound (V), or the compound (VI) and the compound (VII) can be conducted by subjecting the compound (II), the compound (II-1), the compound (II-2), the compound (IV), or the compound (VI) to condensation with a phenol such as 2,4,5-trichlorophenol, pentachlorophenol, 2-nitrophenol or 4-nitrophenol or an N-hydroxy compound such as N-succinimide, N-hydroxy-5-norbornen-endo-2,3-dicarboxyimide (HONB), 1-hydroxy-benztriazole (HOBt) or N-hydroxypiperidine in the presence of a reagent such as dicyclohexylcarbodiimide to convert into an active ester thereof, followed by condensation. Alternatively, the compound (II), the compound (II-1), the compound (II-2), the compound (IV), or the compound (VI) is allowed to react with isobutyl chloroformate to give a mixed acid anhydride, which is then subjected to condensation.

The condensation between the compound (II) and the compound (III), the compound (II-1) and the compound (III). the compound (II-2) and the compound (III), the compound (IV) and the compound (V), or the compound (VI) and the compound (VII) can also be performed by using singly a peptide-formation reagent such as dicyclohexylcarbodiimide, N,N'-carbonyldiimidazole, diphenylphosphoryl azide or diethyl cyanophosphate.

Any of the above-mentioned condensation reactions can be promoted by the addition of preferably an organic base (e.g. triethylamine, N-methylpiperidine, 4-N,N-dimethylaminopyridine). The reaction temperature ranges usually from −20 to +50° C., preferably from 0° C. to about room temperature. Examples of solvents usually employed include dioxane, tetrahydrofuran, acetonitrile, pyridine, N,N-dimethylformamide (DMF), dimethyl sulfoxide, N-methylpyrrolidone, chloroform and methylene chloride, and these can be used singly or as a mixture.

The protective group of the carboxyl group contained in the product of the final method can be removed by a per se known method. For example, a compound having a benzyl ester group can be converted to a carboxylic acid derivative by subjecting the compound to hydrogenation in the presence of a precious metal catalyst such as palladium or platinum, and a compound having a tert-butyl ester group can be converted to a carboxylic acid derivative by processing the compound with an acid such as trifluoroacetic acid or hydrogen chloride.

While salts of the compounds (I), (I-1) and (I-2) can be obtained by the reaction for producing the compounds (I), (I-1) and (I-2) itself, they can be produced also by adding, upon necessity, an acid, alkali or base.

Thus-obtained object compounds (I), (I-1) and (I-2) of this invention can be isolated from the reaction mixture by a conventional separation and purification means such as extraction, concentration, neutralization, filtration, recapitalization, column chromatography and thin-layer chromatography.

In the compounds (I), (I-1) and (I-2), at least two stereoisomers can be present. These individual isomers or a mixture thereof are included in the scope of the present invention. And, it is also possible to produce these isomers individually.

The compounds (I), (I-1) and (I-2) may be hydrated or solvated.

By conducting the reaction as described using a single isomer of the compound (II), the compound (II-1), the compound (II-2), the compound (III), the compound (VI), the compound (V), the compound (VI), or the compound (VII) a single optical isomer of the compound (I), (I-1) or (I-2) can be obtained.

And, when the product is a mixture of two or more isomers, it can be separated into respective isomers by a conventional separation method, for example, a method of causing formation of a salt with an optically active acid (e.g. camphor sulfonic acid, tartaric acid and dibenzoyl tartaric acid), an optically active base (e.g. cinchonine, cinchonidine, quinine, quinidine, α-methylbenzylamine and dehydroabietylamine), or various chromatographic means or fractional recrystallization.

The starting compounds (II), (II-1), (II-2) and (III) in the present invention can be produced in a manner analogous to per se known methods. For example, the compound (III) can be produced by the methods shown by the following reaction scheme.

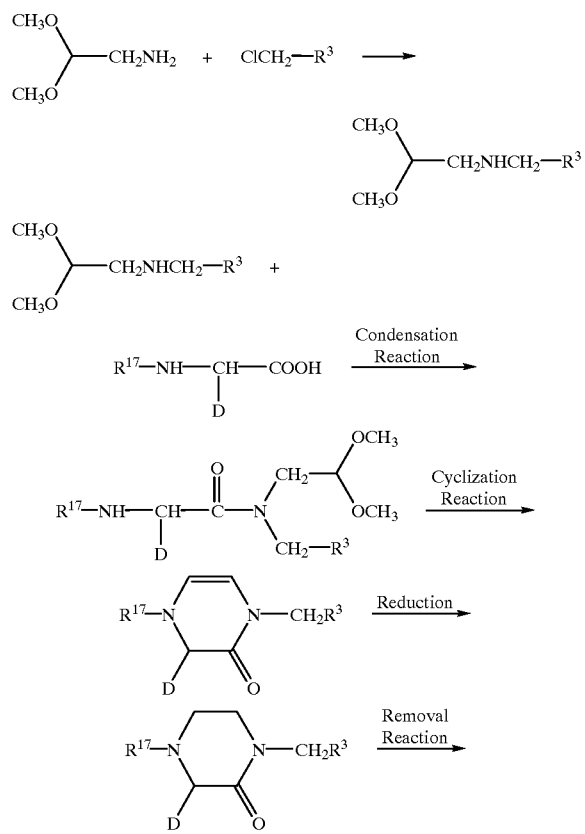

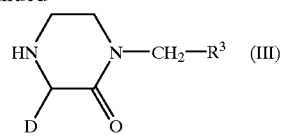

In the above reaction formulae, $R^{17}$ is an amino-protective group and the other symbols are as defined above. Examples of an amino-protective group represented by $R^{17}$ include $C_{7-12}$ aralkyloxy-carbonyl (e.g. benzyloxycarbonyl, etc.), $C_{1-6}$ alkoxy-carbonyl (e.g. tert-butoxycarbonyl, etc.), etc.

In the above-mentioned methods of producing the compound (I), (I-1) or (I-2) and its intermediates, compounds to be employed for the reactions may, unless undesirable effects are brought about, be in the form of a salt with, for example, an inorganic base such as hydrochloride, hydrobromide, sulfate, nitrate or phosphate, an organic base such as acetate, tartrate, citrate, fumarate, maleate, toluenesulfonate or methanesulfonate, a metal salt such as sodium salt, potassium salt or aluminum salt, or a salt with a base such as triethylamine salt, guanidine salt, ammonium salt, hydrazine salt or quinine salt.

When the compound (I), (I-1) or (I-2) is obtained in the free form by the above-mentioned production method, it can be converted to a salt thereof by a conventional method, and when the compound (I), (I-1) or (I-2) is obtained as a salt, it can be converted to the compound (I), (I-1) or (I-2) by a conventional method.

The compounds of the formula (I), (I-1) or (I-2) (including their hydrates) are low in toxicity and are used safely, and inhibit both the binding of fibrinogen, fibronectin and von Willebrand factor to the fibrinogen receptor of blood platelets (Glycoprotein IIb/IIIa) and the binding thereof and other adhesive proteins, such as vitronectin collagen and laminin, to the corresponding receptors on the surface of various types of cells.

Hence, the compounds of this invention exert influence on cell-cell and cell-matrix interactions. They prevent, in particular, the development of thrombus and can be used for treatment or prophylaxis of diseases such as angina pectoris, unstable angina, acute myocardial infarction, Kawasaki disease, acute or chronic heart failure, transient ischemic attack (TIA), cerebral apoplexy, cerebral ischemic disturbance in acute phase of cerebral thrombosis, dissecting aneurysm of the aorta, cerebral vasospasm after subarachnoid hemorrhage, acute or chronic renal disease, chronic and acute glomerulonephrits, diabetic nephropathy and nerve disturbance, nephrotic syndrome, liver diseases, pulmonary embolism, bronchial asthma, pulmonary edema, adult respiratory distress syndrome (ARDS), arteriosclerotic obliteration, peripheral arterial obstruction, deep vein thrombosis, vibration disease, peripheral obstruction complicated with diabetes mellitus, thrombotic thrombocytopenic purpura (TTP), disseminated intravascular coagulation (DIC), sepsis, surgical or infective shock, postoperative and post-delivery trauma, premature separation of placenta, incompatible blood transfusion, systemic lupus erythematosus, Raynaud's disease, inflammations, arteriosclerosis, hemolytic uremic syndrome, symmetric peripheral necrosis, bedsore and hemorrhoids in mammals including humans (e.g. mouse, rat, guinea pig, dog, rabbit and human). And, the compound (I), (I-1) or (I-2) of this invention can be used for preventing thrombosis due to cardiopulmonary bypass surgical operation, surgical operation for pump oxygenator, atrial fibrillation or fracture of hip joint, prosthetic valve replacement, artificial blood vessel and organs, or preventing thrombocytopenia during artificial dialysis, and further for secondary prophylaxis of myocardial infarction. The preventing thrombocytopenia during artificial dialysis also means preventing coagulation or non-washable blood in shunt of extracorporeal dialysis.

Further, the compound (I), (I-1) or (I-2) of this invention can be used for coronary thrombolytic therapy (e.g. enhancing the action of thrombolytic agent such as tissue plasminogen activator (TPA)) and for preventing reobstruction, for preventing reobstruction and restenosis of coronary arteries after PTCA (percutaneous transluminal coronary angioplasty) or stent-indwelling and atherectomy, for preventing reobstruction and restenosis after surgical operation for coronary artery bypass, for preventing ischemic complication (e.g. myocardial infarction, death) after PTCA or coronary thrombolytic therapy, and, besides the compound (I), (I-1) or (I-2) inhibits metastasis of tumors and can be used as an antitumor agent.

And, in case where the compound of this invention is used together with a pharmaceutical preparation whose pharmacological actions are the same or different from that of the compound of this invention, two or more kinds of drugs may be incorporated into one and the same pharmaceutical preparation, or these components can be incorporated into one and the same pharmaceutical preparation (e.g. powdery preparation and injection) at the time of administration. Further, pharmaceutical preparations independently formulated may be administered to one and the same subject simultaneously or at an optional time lag.

Pharmaceutical compositions containing compounds of the formula (I), (I-1) and (I-2) (including their hydrates) can be administered orally in the form of, for example, tablets, lacquered tablets, sugar-coated tablets, hard and soft gelatin capsules, solutions, emulsions or suspensions, or rectally in the form of suppositories, or as spray. However, administration can also be performed non-orally, for example in the form of injectable solutions.

Pharmaceutical preparations of the above-mentioned forms can be formulated by respectively conventional methods using, when necessary, adequate excipients.

The content of the compound (I), (I-1) or (I-2) in the pharmaceutical composition of this invention varies depending on a kind of formulations and is usually about 0.01 to about 100 weight %, preferably about 0.1 to about 50 weight %, more preferably about 0.5 to about 20 weight % based on the total weight of the composition.

To prepare tablets, lacquered tablets, sugar-coated tablets and gelatin capsules, an active compound can be mixed with pharmaceutically inert inorganic or organic excipients. Typical examples of such excipients, which can be used for tablets, sugar-coated tablets and gelatin capsules, include lactose, corn starch or derivatives thereof, talc, and stearic acid or salts thereof. Examples of suitable excipients for soft gelatin capsules are vegetable oil, wax, fat, and, semisolid or liquid polyol. However, no excipients whatever are necessary with soft gelatin capsules when the characteristic features of the active compound are appropriate.

Examples of suitable excipients for the preparation of solutions and syrupy preparations are water, polyol, sucrose, invert sugar and glucose. Suitable examples for injectable solution are water, alcohol, polyol, glycerol and vegetable oil.

Suitable examples for suppositories are natural or hardened oil, wax, fat and semiliquid or liquid polyol. The pharmaceutical compositions can additionally contain a preservative, asolubilizer, astabilizer, awettingagent, an emulsifier, a sweetener, a colorant, a flavoring, a salt to alter the osmotic pressure, a buffer, a coating agent or an antioxidant.

The dosage of the active compound for controlling or preventing the diseases referred to hereinbef ore can vary within a wide range and can, of course, be adjusted to suit the individual circumstances in each particular case. While the dosage varies with the subject diseases, symptoms, subject patients and administration routes, when administered orally to a patient of unstable angina, or, ischemic complication or reobstruction of coronary or restenosis of coronary after PTCA or coronary thrombolytic therapy, a dose of about 1 to 500 mg, preferably about 10 to 200 mg of the compound (I), (I-1) or (I-2), per day for an adult (60 kg), divided into one to three times, is appropriate. When administered non-orally to a patient of transient ischemic attack (TIA), unstable angina, or, ischemic complication or reobstruction of coronary or restenosis of coronary after PTCA or coronary thrombolytic therapy, a dose of about 0.05 to 50 mg, preferably about 1 to 20 mg/kg of the compound (I), (I-1) or (I-2) per day to an adult (60 kg), divided into one to three times, is appropriate.

BEST MODE FOR CARRYING OUT THE INVENTION

The following formulation examples, working examples, test examples and reference examples will describe the present invention in further detail, but they are not intended to limit the present invention in any way.

The proton nuclear magnetic resonance ($^1$H-NMR) spectra were recorded on a Varian Gemini-200 (200 MHz) spectrometer using tetramethylsilane as the internal standard and chemical shifts are given in δ values (ppm). In the mixture of solvents, the value indicated in the parentheses means the ration of each solvent. The symbol % stands for weight percent unless otherwise indicated.

```
s: singlet
d: doublet
t: triplet
q: quartet
dd: double doublet
m: multiplet
br: broad
J: coupling constant
```

Test Example 1

Inhibitory Effect on Platelet Aggregation in Guinea Pigs

Test Method

Blood was collected from abdominal aorta of male guinea pigs under anesthesia with pentobarbital (20 mg/kg, i.p.) using sodium citrate as an anticoagulant (final concentration: 0.315%). The sodium citrate-supplemented blood was centrifuged at 1000 g for 3–5 seconds to obtain platelet rich plasma (PRP), which was further centrifuged at 1000 g for 10 minutes respectively at room temperature to obtain platelet poor plasma (PPP). The number of platelet was counted at automatic platelet counter (Sysmex E2500, Toaiyo-denshi). PRP was diluted with PPP to adjust the number of platelets to be about 400,000/µl. Platelet aggregation was measured as follows, using an 8-channel aggregometer (NBS HEMA TRACER VI, Niko Bioscience Inc.): The PRP (250 µl) was incubated at 37° C. for 2 minutes, to n added 25 μl of a test drug solution. Two minutes later, 25 μl of an agent (ADP; finalconcentration: 1 μM) for causing agglutination. The effect of the test drug was shown by the inhibition rate of the maximum aggregation rate of the test group against that of the control group.

The results are shown in Table 1.

TABLE 1

Inhibitory effects of the compounds of Working Examples on platelet aggregation in guinea pigs induced by ADP

| W. Ex. No. | Inhibition of platelet aggregation by ADP, $IC_{50}$ (M) |
| --- | --- |
| 9 | $7.0 \times 10^{-8}$ |
| 12 | $3.8 \times 10^{-8}$ |
| 14 | $7.5 \times 10^{-8}$ |
| 20 | $4.4 \times 10^{-8}$ |
| 24 | $6.2 \times 10^{-8}$ |
| 31 | $6.0 \times 10^{-8}$ |
| 33 | $2.4 \times 10^{-7}$ |
| 36 | $2.2 \times 10^{-7}$ |
| 40 | $5.8 \times 10^{-8}$ |
| 43 | $9.9 \times 10^{-8}$ |

Reference Example 1 tert-Butyl (S,S)-[4-(2-benzyloxycarbonylamino-propionyl)-3-methoxycarbonylmethyl-2-oxopiperazin-1-yl]acetate tert-Butyl (S)-(3-methoxycarbonylmethyl-2-oxo-piperazin-1-yl)acetate (3.0 g) and benzyloxycarbonyl-L-alanine (2.61 g) were dissolved in acetonitrile (40 ml). While stirring the solution at room temperature, 1-ethyl-3-(3-dimethylaminopropyl)carbodiimide hydrochloride (2.45 g) was added to the solution, and the mixture was stirred for 3 hours at room temperature. The reaction mixture was poured into a 5% aqueous solution of potassium hydrogen sulfate and the solution was extracted with ethyl acetate, washed with a saturated aqueous solution of sodium hydrogen carbonate and dried over anhydrous magnesium sulfate ($MgSO_4$). The solution was concentrated under reduced pressure. The residue was purified by means of a silica gel column chromatography (eluent:hexane:ethyl acetate=1:4) to give the titled compound (3.83 g) as a pale yellow amorphous powdery product.

IR(KBr): 2980, 1738, 1657, 1439, 1370, 1231, 1157, 1067 $cm^{-1}$.

$^1$H-NMR(200 MHz, $CDCl_3$) δ: 1.35(3H, d, J=6.8 Hz), 1.47(9H, s), 2.97(1H, dd, J=16.0, 5.2 Hz), 3.11(1H, dd, J=16.0, 5.2 Hz), 3.26–3.40(1H, m), 3.65(3H, s), 3.56–4.12 (3H, m), 3.91(1H, d,J=17.2 Hz),4.28(1H, d, J=17.2 Hz), 4.53–4.75(1H, m),5.00(1H, t, J=4.8Hz), 5.11(2H, s), 5.77 (1H, d, J=8.0 Hz),7.36(5H, s).

Reference Example 2

(S)-4-(2,4-Dimethoxycarbonylmethyl-3-oxopiperazin-1-yl)-4-oxobutanoic Acid

To a mixture of (S)-(3-methoxycarbonylmethyl-2-oxopiperazin-1-yl)acetic acid methyl ester (3.67 g) and succinic anhydride (1.5 g) in dimethylformamide (25 ml) was added 4-dimethylaminopyridine (0.2 g) and the solution was stirred for 3 hours at 60° C. The reaction mixture was concentrated under reduced pressure and the concentrate was purified by means of CHP-20 column chromatography ($H_2O$→50% acetonitrile aqueous solution) to give the titled compound (3.44 g) as a colorless oily substance.

$^1$H-NMR($CD_3OD$) δ: 2.50–4.65 (12H, m), 3.65 (3H, s), 3.74 (3H, s), 5.13(1H, t, J=5.7 Hz).

Reference Example 3

4-Oxo-4-(4-pyridin-2-ylpiperazin-1-yl)butanoic Acid

A solution of 1-(2-pyridyl)piperazine (1.63 g) and succinic anhydride (1.1 g) in dimethylf ormamide (5 ml) was stirred for 24 hours at room temperature. The reaction mixture was reduced under reduced pressure and the concentrate was recrystallized from ethanol to give the titled compound (1.7 g) as a pale yellow crystal.

m.p.: 125–127° C.

Elemental Analysis for $C_{13}H_{17}N_3O_3$ Calcd.: C, 59.30; H, 6.51; N, 15.96. Found: C, 59.02; H, 6.56; N, 15.91.

$^1$H-NMR ($CD_3OD$) δ: 2.50–2.76 (4H, m), 3.45–3.75 (8H, m), 6.70 (1H, m), 6.85 (1H, d, J=8.8 Hz), 7.58 (1H, m), 8.10 (1H, m).

IR (KBr): 3200, 1740, 1620 $cm^{-1}$.

Reference Example 4

4-Oxo-4-(4-pyrimidin-2-ylpiperazin-1-yl)butanoic Acid

A solution of 1-(2-pyrimidinyl)piperazine (3.28 g) and succinic anhydride (2.2 g) in dimethylformamide (15 ml) was stirred for 1 hour at room temperature. The reaction mixture was concentrated under reduced pressure and the concentrate was recrystallized from ethanol/ethyl ether to give the titled compound (3.73 g) as a colorless crystal.

m.p.: 168–170° C.

Elemental Analysis for $C_{12}H_{16}N_4O_3$ Calcd.: C, 54.54; H, 6.10; N, 21.20. Found: C, 54.48; H, 5.92; N, 21.24.

$^1$H-NMR ($CD_3OD$) δ: 2.73 (4H, s), 3.50–3.95 (8H, m), 6.56 (1H, t, J=4.8 Hz), 8.35 (2H, d, J=4.8 Hz).

IR (KBr): 3220, 1730, 1725, 1620 $cm^{-1}$.

Reference Example 5

4-Oxo-4-(4-pyridin-4-ylpiperazin-1-yl)butanoic Acid

To an aqueous solution (10 ml) of 1-(4-pyridyl)-piperazine (1.63 g) were added 2N sodium hydroxide (5.5 ml) and ethylsuccinyl chloride at 0° C. and the solution was stirred for 1 hour at room temperature 1 hour. The reaction solution was saturated with sodium chloride, extracted with ethyl acetate three times and dried over $Na_2SO_4$. The solution was removed under reduced pressure and the residue was dissolved in methanol (10 ml). To the solution was added 2N sodium hydroxide (11 ml) and the solution was stirred for 1 hour at room temperature. The pH of the reaction mixture was adjusted to 5 with acetic acid and the solution was concentrated under reduced pressure and the concentrate was recrystallized from ethanol to give the titled compound (1.4 g) as a colorless crystal.

m.p.: 261–263° C.

Elemental Analysis for $C_{13}H_7N_3O_3$ Calcd.: C, 58.90; H, 6.54; N, 15.85. Found: C, 58.98; H, 6.55; N, 15.93.

$^1$H-NMR ($CD_3OD$) δ: 2.44–2.75 (4H, s),3.50–3.90 (8H, m), 7.04 (2H, d, J=7.2 Hz), 8.16 (2H, d, J=7.2 Hz).

Reference Example 6

(S)-4-(4-tert-Butoxycarbonylmethyl-2-methoxycarbonyl-methyl-3-oxopiperazin-1-yl)-4-oxobutanoic Acid A mixture of (S)-(3-methoxycarbonylmethyl-2-oxo-piperazin-1-yl)acetic acid tert-butyl ester (1.0 g) and succinic anhydride (0.7 g) in dimethylformamide (15 ml) was stirred for 5 hours at room temperature. The reaction mixture was concentrated under reduced pressure. The concentrate was dissolved in water (10 ml) and purified by means of CHP-20 column chromatography ($H_2O \rightarrow 30\%$ acetonitrile aqueous solution) to give the titled compound (1.3 g) as a colorless oily product.

$^1$H-NMR (CD$_3$OD) δ: 1.47 (9H, s), 2.52–4.65 (12H, m), 3.65 (3H, s), 5.11 (1H, t, J=6.0 Hz).

IR (KBr): 2980, 1736, 1655 cm$^{-1}$.

Reference Example 7

2-(4-Methoxybenzyl)succinic acid 1-methyl ester

To a solution of 2-(4-methoxybenzylidene)succinic acid 1-methyl ester (3 g) in methanol (100 ml) was added 10% palladium on carbon (0.6 g) and the solution was stirred for 16 hours under hydrogen atomosphere at room temperature. The catalyst was filtered off and the filtrate was concentrated under reduced pressure to give the titled compound (3 g) as a colorless oily substance.

$^1$H-NMR (CD$_3$OD) δ: 2.33–3.18 (5H, m), 3.67 (3H, s), 3.79 (3H, s), 6.83 (2H, d, J=8.8 Hz), 7.07 (2H, d, J=8.8 Hz).

IR (KBr): 1732, 1713, 1613 cm$^{-1}$.

Reference Example 8

2-(4-Methoxybenzyl)-4-oxo-4-(4-pyridin-4-ylpiperazin-1-yl)butanoic Acid Methyl Ester To a solution of 2-(4-methoxybenzyl)succinic acid 1-methyl ester (3 g) in acetonitrile (60 ml) were added HOBt (1-hydroxy-1H-benzotriazole monohydrate) (1.84 g) and 1-ethyl-3-(3-dimethylamgnopropyl)carbodiiide hydrochloride (2.76 g) and the solution was stirred for 10 minutes. To the solution was added 1-(4-pyridyl)-piperazine (1.96 g) and the solution was stirred for 30 minutes at room temperature. The reaction mixture was concentrated and the concentrate was made basic with an aqueous solution of sodium hydrogen carbonate to give an alkaline solution, which was extracted with ethyl acetate twice. The extract was washed with saturated brine and dried over Na$_2$SO$_4$. The solution was concentrated under reduced pressure and recrystallized from ethyl acetate/hexane to give the titled compound (4.25 g) as colorless needles.

m.p.: 143–145° C.

Elemental Analysis for: C$_{22}$H$_{27}$N$_3$O$_4$ Calcd.: C, 66.48; H, 6.85; N, 10.57. Found: C, 66.37; H, 6.78; N, 10.69.

$^1$H-NMR (CD$_3$OD) δ: 2.42–3.00 (4H, m), 3.00–3.25 (1H, m), 3.30–3.55 (4H, m), 3.55–3.75 (4H, m), 3.61 (3H, s), 3.75 (3H, s), 6.84 (2H, d, J=8.8 Hz), 6.84 (2H, d, J=6.6 Hz), 7.09 (2H, d, J=8.8 Hz), 8.14 (2H, d, J=6.6 Hz).

IR (KBr): 1723, 1632, 1595 cm$^{-1}$.

Reference Example 9

2-(4-Methoxybenzyl)-4-oxo-4-(4-pyridin-4-ylpiperazin-1-yl)butanoic Acid

To a solution of 2-(4-methoxybenzyl)-4-oxo-4-(4-pyridin-4-ylpiperazin-1-yl)butanoic acid methyl ester (3.94 g) in methanol (30 ml) was added 2N sodium hydroxide (12 ml) and the solution was stirred for 6 hours. To the solution was added acetic acid (1.5 ml) and the reaction solution was concentrated. The concentrate was purified by CHP-20 column chromatography ($H_2O \rightarrow 30\%$ acetonitrile aqueous solution) and recrystallized with acetone to give the titled compound (3.49 g) as a colorless crystal.

m.p.: 202–203° C.

Elemental Analysis for: C$_{21}$H$_{25}$N$_3$O$_4$ Calcd.: C, 65.78; H, 6.57; N, 10.96. Found: C, 65.57; H, 6.53; N, 11.02.

$^1$H-NMR (CD$_3$OD-DCl) δ: 2.33–3.25 (5H, m), 3.58–3.92 (8H, m), 3.76 (3H, s), 6.58 (2H, d, J=8.8 Hz), 7.15 (2H, d, J=8.8 Hz), 7.16 (2H, d, J=7.6 Hz), 8.17 (2H, d, J=7.6 Hz).

IR (KBr): 1624, 1530 cm$^{-1}$.

Reference Example 10

(R,S)-3-tert-Butoxycarbonylamino-4-(4-tert-butoxycarbonylmethyl-2-methoxycarbonylmethyl-3-oxopiperazin-1-yl)-4-oxobutanoic Acid Benzyl Ester In acetonitrile (50 ml) were dissolved (S)-(3-methoxycarbonylmethyl-2-oxopiperazin-1-yl)acetic acid tert-butyl ester oxalic acid salt (3.8 g) and tert-butoxycarbonyl-D-aspartic acid β-benzyl ester(4.08 g). To the solution was added 1-ethyl-3-(3-dimethylamino-propyl)carbodiimide hydrochloride (2.80 g) while stirring at room temperature and the mixture was stirred for 4 hours at room temperature. The reaction mixture was poured into a 5% saturated aqueous solution of potassium hydrogen sulfate and extracted with ethyl acetate. The extract was washed with a saturated aqueous solution of sodium hydrogen carbonate, dried over anhydrous magnesium sulfate and concentrated under reduced pressure. The residue was purified by means of silica gel column chromatography (eluent:ethyl acetate:hexane=1:3) to give the titled compound (6.62 g) as a white amorphous powdery product.

IR (KBr): 2978, 1740, 1655, 1439, 1368, 1163 cm$^{-1}$.

$^1$H NMR(200 MHz, CDCl$_3$) δ: 1.42 (9H, s), 1.46 (9H, s), 2.57–2.73 (1H, m), 2.76–3.10 (3H, m), 3.16–3.31 (1H, m), 3.54–3.91 (2H, m), 3.64 (3H, s), 3.98 (1H, d, J=17.4 Hz), 4.16 (1H, d, J=17.4 Hz), 4.16–4.34 (1H, m), 4.90–5.16 (2H, m), 5.12 (2H, s), 5.43 (1H, d, J=8.8 Hz), 7.35 (5H, s).

Reference Example 11

(S,S)-3-tert-Butoxycarbonylamino-4-(4-tert-butoxycarbonylmethyl-2-methoxycarbonylmethyl-3-oxopiperazin-1-yl)-4-oxobutanoic Acid Benzyl Ester In substantially the same manner as in Reference Example 10, the titled compound was produced as a white amorphous powdery product (80%).

IR(KBr): 2978, 1740, 1661, 1439, 1368, 1161 cm$^{-1}$.

$^1$H NMR (200 MHz, CDCl$_3$) δ: 1.43 (9H, s), 1.47(9H, s), 2.60–2.80 (1H, m), 2.80–3.10 (3H, m), 3.10–3.35 (1H, m), 3.45–4.30(5H, m), 3.66 (3H, s), 4.85–5.40 (5H, m), 7.34 (5H, s).

Working Example 1

(S, S)-[3-Methoxycarbonylmethyl-2-oxo-4-[2-(4-pyridin-4-ylbenzoylamino)propionyl]piperazin-1-yl] acetic acid tert-butyl ester A mixture of (S,S)-[4-(2-benzyloxycarbonylamino-propionyl)-3-methoxycarbonyl-2-oxopiperazin-1-yl]acetic acid tert-butyl ester (0.74 g) produced in Reference Example 1, 10% palladium on carbon (0.15 g) and methanol (7.4 ml) was stirred for 1 hour under hydrogen atmosphere at room temperature 1 hour. The catalyst was filtered off and the filtrate was concentrated. Thus produced amino derivative and 4-(pyridin-4-yl)benzoic acid (0.3 g) were dissolved in DMF (dimethylformamide) (7.4 ml). To the solution was added 1-ethyl-3-(3-dimethylaminopropyl)carbodiimide hydrochloride (0.32 g) while stirring and the solution was stirred for 4 hours at room temperature. The reaction solution was poured into a saturated aqueous solution of sodium hydrogen carbonate and extracted with ethyl acetate. The extract was dried over anhydrous magnesium sulfate and concentrated under reduced if pressure. The residue was purified by means of a silica gel column chromatography (eluent:ethyl acetate:methanol=20:1) to give the titled compound (0.2 g) as a white amorphous powdery product.

IR(KBr): 1740, 1655, 1431, 1370, 1231, 1155 cm$^{-1}$.

$^1$H NMR(200 MHz, CD$_3$OD) δ: 1.47 (9H, s), 1.30–1.70 (3H, m), 2.80–4.40 (8H, m), 3.63 (3H, s), 5.00–5.20 (2H, m), 7.74 (2H, d, J=6.0 Hz), 7.84 (2H, d, J=8.0 Hz), 8.00 (2H, d, J=8.0 Hz), 8.61 (2H, d, J=6.0 Hz).

Working Example 2

(S,S)-[3-Methoxycarbonylmethyl-2-oxo-4-[2-(4-pyridin-4-ylbenzoylamino)propionyl]piperazin-1-yl] acetic Acid Trifluoroacetic Acid Salt To a solution of (S,S)-[3-methoxycarbonylmethyl-2-oxo-4-[2-(4-pyridin-4-ylbenzoylamino)propionyl]-piperazin-1-yl]acetic acid tert-butyl ester (0.2 g) produced in Working Example 1 in toluene (2.0 ml) was added trifluoroacetic acid (2.0 ml) and the solution was stirred for 1 hour at room temperature. The reaction mixture was concentrated under reduced pressure and recrystallized from methanol-ethyl ether to give the titled compound (0.18 g) as a colorless crystal.

Specific Optical Rotation: [α]$_D^{20}$+81.9° (C=0.496, MeOH)

Elemental Analysis for C$_{24}$H$_{26}$N$_4$O$_7$·CF$_3$COOH·0.5H$_2$O Calcd.: C, 51.57; H, 4.66; N, 9.25. Found: C, 51.59; H, 4.69; N, 9.31.

IR(KBr): 1742, 1644, 1493, 1300, 1202, 1175 cm$^{-1}$.

$^1$H NMR(200 MHz, CD$_3$OD) δ: 1.47 (3H, d, J=7.0 Hz), 2.94 (2H, d, J=5.6 Hz), 3.00–4.40 (4H, m), 3.63 (3H, s), 4.08 (1H, d, J=17.4 Hz), 4.32 (1H, d, J=17.4 Hz), 5.00–5.20 (2H,m), 7.90–8.15 (4H, m), 8.28 (2H, d, J=6.8 Hz), 8.84 (2H, d, J=6.8 Hz).

Working Example 3

(S,S)-[3-Methoxycarbonylmethyl-2-oxo-4-[2-(4-piperidin-4-ylbenzoylamino)propionyl]piperazin-1-yl]acetic Acid Trifluoroacetic Acid Salt A mixture of (S,S)-[3-methoxycarbonylmethyl-2-oxo-4-[2-(4-pyridin-4-ylbenzoylamino)propionyl]piperazin-1-yl] acetic acid trifluoroacetic acid salt (0.11 g) produced in Working Example 2, platinum oxide (0.011 g) and acetic acid (1.1 ml) was stirred for 6 hours under hydrogen atmosphere at room temperature. The catalyst was filtered off and the filtrate was concentrated under reduced pressure. The residue was purified by means of CHP-20 column chromatography (eluent:H$_2$O). The desired fraction was concentrated and subjected to lyophilization to give the titled compound (0.1 g) as a white amorphous powdery product.

Specific Optical Rotation: [α]$_D^{20}$+48.0° (C=0.503, H$_2$O)

Elemental Analysis for C$_{24}$H$_{32}$N$_4$O$_7$·CF$_3$COOH·1.6H$_2$O Calcd.: C, 49.46; H, 5.78; N, 8.87. Found: C, 49.77; H, 6.13; N, 9.18.

IR(KBr): 1732, 1651, 1535, 1503, 1453, 1202 cm$^{-1}$.

Working Example 4

(S,S)-[3-Methoxycarbonylmethyl-4-[3-(4-methoxyphenyl) -2-(4-pyridin-4-ylbenzoylamino) propionyl]-2-oxo-piperazin-1-yl]acetic Acid tert-butyl ester A mixture of (S,S)-[4-[2-benzyloxycarbonylamino-3-(4-methoxyphenyl)propionyl]-3-methoxycarbonylmethyl-2-oxopiperazin-1-yl]acetic acid tert-butyl ester (0.96 g), 10% palladium on carbon (0.18 g) and methanol (9.6 ml) was stirred for 1 hour under hydrogen atmosphere at room temperature. The catalyst was filtered off and the filtrate was concentrated under reduced pressure. To the concentrate were added 4-(pyridin-4-yl)benzoic acid (0.35 g) and dimethylformamide (9.6 ml). To the solution was added 1-ethyl-3-(3-dimethylaminopropyl)carbodiimide hydrochloride (0.37 g) and the solution was stirred for 6 hours at room temperature. The reaction mixture was poured into an aqueous solution of saturated sodium hydrogen carbonate and extracted with ethyl acetate. The extract was dried over anhydrous magnesium sulfate and concentrated under reduced pressure. The residue was purified by means of a silica gel column chromatography (eluent:ethyl acetate/methanol=30/1) and recrystallized from methanol/ethyl ether to give the titled compound (0.43 g) as colorless needles.

Specific Optical Rotation: [α]$_D^{20}$+62.6° (c=0.500, MeOH)

Elemental Analysis for C$_{35}$H$_{40}$N$_4$O$_8$ Calcd.: C, 65.20; H, 6.25; N, 8.69. Found: C, 65.02; H, 6.33; N, 8.68.

IR(KBr): 1742, 1632, 1512, 1447, 1240, 1157 cm$^{-1}$.

$^1$H NMR (200 MHz, CD$_3$OD+DCl) δ: 1.47 (9H, s), 2.60–2.80 (1H, m), 2.88 (2H, d, J=5.8 Hz), 3.02–4.14 (5H, m), 3.60 (3H, s), 3.77 (3H, s), 3.94 (2H, s), 5.02 (1H, t, J=5.4 Hz), 5.05–5.30 (1H, m), 6.87 (2H, d, J=8.4 Hz), 7.22 (2H, d, J=8.4 Hz), 7.94–8.17 (4H, m), 8.48 (2H, d, J=6.8 Hz), 8.93 (2H, d, J=6.8 Hz).

Working Example 5

(S,S)-[3-Methoxycarbonylmethyl-4-[3-(4-methoxyphenyl)-2-(4-pyridin-4-ylbenzoylamino) propionyl]-2-oxo-piperazin-1-yl]acetic Acid Trifluoroacetic Acid Salt A mixture (S,S)-[3-methoxycarbonylmethyl-4-[3-(4-methoxyphenyl)-2-(4-pyridin-4-ylbenzoylamino)-propionyl]-2-oxopiperazin-1-yl]acetic acid tert-butyl ester (0.46 g) produced in Working Example 4, trifluoroacetic acid (2.3 ml) and toluene (2.3 ml) was stirred for 1 hour at room temperature. The reaction mixture was concentrated under reduced pressure. The concentrate was purified by means of LH-20 column chromatography (eluent:methanol). The objected fraction was concentrated and subjected to lyophilization to give the titled compound (0.43 g) as a white amorphous powdery product.

Specific Optical Rotation: [α]$_D^{20}$+50.0° (C=0.500, MeOH)

Elemental Analysis for C$_{31}$H$_{32}$N$_4$O$_8$·CF$_3$COOH·H$_2$O Calcd.: C, 55.00; H. 4.90; N, 7.77. Found: C, 55.23; H, 4.63; N, 7.91.

IR(KBr): 1734, 1661, 1514, 1493, 1250, 1196 cm$^{-1}$.

$^1$H NMR (200 MHz, CD$_3$OD) δ: 2.58–4.28 (8H, m), 2.88 (2H, d, J=6.4 Hz), 3.58 (3H, s), 3.76 (3H, s), 5.00–5.11 (1H, m), 5.12–5.24 (1H, m), 6.86 (2H, d, J=8.6 Hz), 7.20 (2H, d, J=8.6 Hz), 7.90–8.10 (4H, m), 8.20–8.35 (2H, m), 8.70–8.95 (2H, m).

Working Example 6

(S,S)-[3-Methoxycarbonylmethyl-4-[3-(4-methoxyphenyl)-2-(4-piperidin-4-ylbenzoylamino)propionyl]-2-oxo-piperazin-1-yl]acetic Acid A mixture of (S,S)-[3-methoxycarbonylmethyl-4-[3-(4-methoxyphenyl)-2-(4-pyridin-4-ylbenzoylamino)-propionyl]-2-oxopiperazin-1-yl]acetic acid trifluoro-acetic acid salt (0.30 g) produced in Working Example 5, platinum oxide (0.030 g) and acetic acid (3 ml) was stirred for 7 hours under hydrogen atmosphere at room temperature. The catalyst was filtered off and the filtrate was concentrated under reduced pressure. The concentrate was purified by means of CHP-20 column chromatography (eluent:$H_2O \rightarrow 20\%$ acetonitrile aqueous solution). The objected fraction was concentrated and subjected to lyophilization to give the titled compound (0.15 g) as a white amorphous powdery product.

Optical Rotation: $[\alpha]_D^{20}$+63.1° (C=0.538, $H_2O$)

Elemental Analysis for $C_{31}H_{38}N_4O_8 \cdot 3.5H_2O$ Calcd.: C, 56.61; H, 6.90; N, 8.52. Found: C, 56.60; H, 6.93; N, 8.66.

IR(KBr): 1732, 1634, 1512, 1449, 1383, 1302, 1248, 1181 $cm^{-1}$.

$^1$H NMR (200 MHz, $D_2O$) δ: 1.20–2.25 (6H, m), 2.25–2.53 (1H, m), 2.65–3.38 (6H, m), 3.38–3.88 (4H, m), 3.55 (3H, s), 3.81 (3H, s), 3.88–4.15 (2H, m), 4.95–5.19 (2H, m), 6.94 (2H, d, J=8.2 Hz), 7.22 (2H, d, J=8.2 Hz), 7.44 (2H, d, J=8.2 Hz), 7.75 (2H, d, J=8.2 Hz).

Working Example 7

(S,S)- [3-Methoxycarbonylmethyl-2-oxo-4-[2-[(3,4,5,6-tetrahydro-2H-[1,4']bipyridinyl-4-carbonyl)amino]-propionyl]piperazin-1-yl]acetic Acid In substantially the same manner as in Working Example 2, the titled compound (0.22 g, 26%) was produced as a white amorphous powdery product.

Specific Optical Rotation: $[\alpha]_D^{20}$+17.3° (C=0.501, $H_2O$)

Elemental Analysis for $C_{23}H_{31}N_5O_7 \cdot 1.5H_2O \cdot 0.2MeOH$ Calcd.: C, 53.28; H, 6.71; N, 13.39. Found: C, 53.31; H, 7.10; N, 13.48.

IR(KBr): 1730, 1644, 1549, 1447, 1385, 1217 $cm^{-1}$.

$^1$H NMR (200 MHz, $D_2O$) δ: 1.37 (3H, d, J=7.0 Hz), 1.58–2.08 (4H, m), 2.64–4.32 (13H, m), 3.67 (3H, s), 4.70–4.90 (1H, m), 5.12 (1H, t, J=6.2 Hz), 7.06 (2H, d, J=7.4 Hz), 8.03 (2H, d, J=7.4 Hz).

Working Example 8

(S)-[3-Methoxyarbonylmethyl-2-oxo-4-[[(3,4,5,6-tetrahydro-2H-[1,4']bipyridinyl-4-carbonyl)amino]-acetyl]piperazin-1-yl]acetic Acid To a solution of (S)-(4-benzyloxycarbonylamino-3-methoxycarbonylmethyl-2-oxopiperazin-1-yl)acetic acid tert-butyl ester (1.0 g) in methanol (50 ml) was added 10% palladium on carbon (0.3 g) and the solution was stirred for 1 hour under hydrogen atmosphere. The catalyst was filtered off and the filtrate was concentrated under reduced pressure. To the residue were added dimethyl-formamide (10 ml) and water (10 ml). To the solution were added 1-(4-pyridyl)piperidin-4-carboxylic acid (0.71 g), N-hydroxy-5-norbornen-2,3-dicarboxyimide (0.39 g) and dicyclohexyldiimide (0.68 g) and the solution was stirred for 24 hours at room temperature. Insoluble materials were filtered off and the filtrate was concentrated under reduced pressure. The concentrate was dissolved in water (20 ml) and was purified by CHP-20 column chromatography ($H_2O \rightarrow 40\%$ acetonitrile aqueous solution). To the produced ester derivative was added trifluoroacetic acid (6 ml) and the solution was stirred for 3 hours at room temperature. The reaction mixture was concentrated under reduced pressure and the concentrate was purified by CHP-20 column chromatography ($H_2O \rightarrow 10\%$ acetonitrile aqueous solution). The objected fraction was concentrated and subjected to lyophilization to give the titled compound (0.28 g) as a white amorphous powdery product.

Elemental Analysis for $C_{22}H_{29}N_5O_7 \cdot 2H_2O$ Calcd.: C, 51.66; H, 6.50; N, 13.69. Found: C, 51.68; H, 6.49; N, 13.71.

$^1$H-NMR ($D_2O$) δ: 1.60–1.88 (2H, m), 1.92–2.15 (2H, m), 2.70–4.58 (15H, m), 3.67 (3H, s), 5.11 (1H, t, J=6.2 Hz), 7.04 (2H, d, J=7.6 Hz), 8.00 (2H, d, J=7.6 Hz).

IR (KBr): 1733, 1646 $cm^{-1}$.

Working Example 9

(S,S) -[3 -Methoxycarbonylmethyl- 4-[3-(4-methoxyphenyl) -2-[(3,4,5,6-tetrahydro-2H-[1,4'] bipyridinyl-4-carbonyl)amino]propionylI-2-oxopiperazin-1-yl]acetic Acid To a solution of (S,S)-[4-[2-benzyloxycarbonyl-amino-3-(4-methoxyphenyl)propionyl]-3-methoxycarbonyl-methyl-2-oxopiperazinl-yl]acetic acid tert-butyl ester (1.09 g) in methanol (50 ml) was added 10% palladium on carbon (0.3 g) and the solution was stirred for 1 hour under hydrogen atmosphere. The catalyst was filtered off and the filtrate was concentrated under reduced pressure. To the residue were added dimethylformamide (15 ml) and water (15 ml). To the solution were added 1-(4-pyridyl)-piperidin-4-carboxylic acid (0.71 g), N-hydroxy-5-norbornen-2,3-dicarboxyimide (0.36 g) and dicyclo-hexylcarbodiimide (0.56 g) and the solutionwas stirred for 24 hours at room temperature. Insoluble materials were filtered off and the filtrate was concentrated under reduced pressure. The concentrate was dissolved in water (20 ml) and was purified by CHP-20 column chromatography ($H_2O \rightarrow$methanol). To the produced ester derivative was added trifluoroacetic acid (8 ml) and the solution was stirred for 2 hours at room temperature. The reaction mixture was concentrated under reduced pressure and the concentrate was purified by means of CHP-20 column chromatography ($H_2O \rightarrow 20\%$ acetonitrile aqueous solution). The objected fraction was concentrated and subjected to lyophilization to give the titled compound (0.98 g) as a colorless crystal.

m.p.: 142–145° C.

Elemental Analysis for $C_{30}H_{37}N_5O_8 \cdot 3.5H_2O$ Calcd.: C, 54.70; H, 6.73; N, 10.63. Found: C, 54.81; H, 6.55; N, 10.76.

$^1$H-NMR ($D_2O$-DCl) δ: 1.35–2.00 (4H, m), 2.25–4.35 (15H, m), 3.59 (3H, s), 3.76 (3H, s), 4.80–5.02 (2H, m), 6.89 (2H, d, J=8.6 Hz), 6.98 (2H, d, J=7.6 Hz), 7.15 (2H, d, J=8.6 Hz), 7.96 (2H, d, J=7.6 Hz).

IR (KBr): 1739, 1646 $cm^{-1}$.

Working Example 10

(S)-[3-Methoxycarbonylmethyl-2-oxo-4-[4-oxo-4-(4-pyridin-4-ylpiperazin-1-yl)butyryl]piperazin-1-yl] acetic Acid Methyl Ester To a solution of (S)-4-(2,4-dimethoxycarbonylmethyl-3-oxopiperazin-1-yl)-4-oxobutanoic acid (0.62 g) produced in Reference Example 2 and 4-pyridylpiperazine (0.3 g) in dimethylformamide (20 ml) were added HOBt (0.28 g) and dicyclohexylcarbodiimide (0.41 g) and the solution was stirred for 24 hours at room temperature. Insoluble materials were filtered off and the filtrate was concentrated under reduced pressure. The residue was dissolved in water (20 ml). The solution was adjusted to pH 3 with 1N hydrochloric acid and was purified by means of CHP-20 column chromatography ($H_2O \rightarrow 5\%$ acetonitrile aqueous solution). The objected fraction was concentrated and subjected to lyophilization to give the titled compound (0.31 g) as a white amorphous powdery product.

Elemental Analysis for $C_{23}H_{31}N_5O_7 \cdot HCl \cdot 1.2H_2O$ Calcd.: C, 50.45; H, 6.33; N, 12.79. Found: C, 50.42; H, 6.46; N, 12.78.

$^1$H-NMR (CD$_3$OD) δ: 2.60–4.65 (20H, m)., 3.64 (3H, s)s, 3.74 (3H, s), 5.10 (1H, t, J=5.0 Hz), 7.19 (2H, d, J=7.8 Hz), 8.29 (2H, d, J=7.8 Hz).

Working Example 11

(S)-[3-Methoxycarbonylmethyl-2-oxo-4-[4-oxo-4-(4-pyridin-4-ylpiperazin-1-yl)butyryl]piperazin-1-yl] acetic Acid To a solution of (S)-(3-methoxycarbonylmethyl-2-oxo-piperazin-1-yl)acetic acid tert-butyl ester (0.39 g), 4-oxo-4-(4-pyridin-4-ylpiperazin-1-yl)butanoic acid (0.37 g) produced in Reference Example 5 and HOBt (0.21 g) in dimethylformamide (30 ml) was added 1-ethyl-3-(3-dimethylaminopropyl)carbodiimide hydrochloride (0.52 g) and the solution was stirred for 24 hours at room temperature. The reaction mixture was concentrated under reduced pressure and the concentrate was purified by means of CHP-20 column chromatography ($H_2O \rightarrow 30\%$ acetonitrile aqueous solution). To the produced ester derivative was added trifluoroacetic acid (10 ml) and the solution was stirred for 2 hours at room temperature. The reaction mixture was concentrated under reduced pressure and the concentrate was purified by means of CHP-20 column chromatography ($H_2O \rightarrow 10\%$ acetonitrile aqueous solution). The objected fraction was concentrated and subjected to lyophilization to give the titled compound (0.44 g) as a white amorphous powdery product.

Elemental Analysis for $C_{22}H_{29}N_5O_7 \cdot 2.5H_2O$ Calcd.: C, 50.76; H, 6.58; N, 13.45. Found: C, 50.56; H, 6.53; N, 13.56.

$^1$H-NMR (CD$_3$OD) δ: 2.60–4.65 (20H, m), 3.63 (3H, s), 5.14 (1H, t, J=6.1 Hz), 7.14 (2H, d, J=7.6 Hz), 8.17 (2H, d, J=7.6 Hz).

IR (KBr): 1733, 1646 cm$^{-1}$.

Working Example 12

(S)-[3-Methoxycarbonylmethyl-2-oxo-4-[4-oxo-4-(4-pyridin-2-ylpiperazin-1-yl)butyryl]piperazin-1-yl] acetic Acid Methyl Ester To a solution of (S)-4-(2,4-dimethoxycarbonyl-methyl-3-oxopiperazin-1-yl)-4-oxobutanoic acid (0.50 g) produced in Reference Example 3 and 1-(2-pyridyl)-piperazin (0.26 g) in tetrahydrofuran (20 ml) was added 1-ethyl-3-(3-dimethylaminopropyl)carbodiimide hydrochloride (0.34 g) and the solution was stirred for 5 hours at room temperature. The reaction mixture was concentrated under reduced pressure. The concentrate was dissolved in water (10 ml). The solution was adjusted to pH 2 with 1N hydrochloric acid was purified by means of CHP-20 column chromatography ($H_2O \rightarrow 30\%$ acetonitrile aqueous solution). The objected fraction was concentrated and subjected to lyophilization to give the titled compound (0.55 g) as a white amorphous powdery product.

Elemental Analysis for $C_{23}H_{31}N_5O_7 \cdot 0.5H_2O$ Calcd.: C, 55.41; H, 6.47; N, 14.05. Found: C, 55.69; H, 6.53; N, 14.01.

$^1$H-NMR (CD$_3$OD) δ: 2.60–4.65 (20H, m), 3.65 (3H, s), 3.74 (3H, s), 5.11 (1H, t, J=5.9 Hz), 6.70 (1H, m), 6.85 (2H, d, J=8.6 Hz), 7.58 (1H, m), 8.11 (1H, m).

IR (KBr): 1735, 1654 cm$^{-1}$.

Working Example 13

(S)-[3-Methoxycarbonylmethyl-2-oxo-4-[4-oxo-4-(4-pyridin-2-ylpiperazin-1-yl)butyryl]piperazin-1-yl] acetic Acid To suspension of (S)-(3-methoxycarbonylmethyl-2-oxopiperazin-1-yl)acetic acid tert-butyl ester (0.64 g) and 4-oxo-4-(4-pyridin-2-ylpiperazin-1-yl)butanoic acid (0.65 g) produced in Reference Example 3 in acetonitrile (20 ml) was added 1-ethyl-3-(3-dimethylaminopropyl)-carbodiimide hydrochloride (0.52 g) and the suspension was stirred for 5 hours at room temperature. The reaction mixture was concentrated under reduced pressure and the concentrate was purified by means of a silica gel column chromatography (acetonitrile/methanol=9/1). To the produced ester derivative was added trifluoroacetic acid (10 ml) and the solution was stirred for 2 hours at room temperature. The reaction mixture was concentrated under reduced pressure and the concentrate was purified by means of CHP-20 column chromatography ($H_2O \rightarrow 10\%$ acetonitrile aqueous solution). The objected fraction was concentrated and subjected to lyophilization to give the titled compound (0.84 g) as a white amorphous powdery product.

Elemental Analysis for $C_{22}H_{29}N_5O_7 \cdot 1.5H_2O$ Calcd.: C, 52.58; H, 6.42; N, 13.94. Found: C, 52.62; H, 6.12; N, 13.76.

$^1$H-NMR (CD$_3$OD) δ: 2.60–4.65 (20H, m), 3.64 (3H, s), 5.13 (1H, t, J=5.8 Hz), 6.73 (1H, m), 6.89 (1H, d, J=8.8 Hz), 7.62 (1H, m), 8.10 (1H, m).

IR (KBr): 1730, 1640 cm$^{-1}$.

Working Example 14

(S)-[3-Methoxycarbonylmethyl-2-oxo-4-[4-oxo-4-(4-pyrimidin-2-ylpiperazin-1-yl)butyryl]piperazin-1-yl]acetic Acid Methyl Ester To a solution of (S)-(2,4-dimethoxycarbonyl-methyl-3-oxopiperazin-1-yl)-4-oxobutanoic acid (0.74 g), 4-(2-pyrimidinyl)piperazine (0.39 g) and HOBt (0.33 g) in tetrahydrofuran (30 ml) was added 1-ethyl-3-(3-dimethylaminopropyl)carbodiimide hydrochloride (0.5 g) and the solution was stirred for 14 hours at room temperature. The reaction mixture was concentrated under reduced pressure. To the concentrate were added saturated brine and a saturated aqueous solution of sodium hydrogen carbonate to give an alkaline solution, which was extracted with ethyl acetate. The extract was concentrated under reduced pressure. To the concentrate were added water and 1N hydrochloric acid and the solution was adjusted to pH 2, which was purified by means of CHP-20 column chromatography ($H_2O \rightarrow 20\%$ acetonitrile aqueous solution). The objected fraction was concentrated and subjected to lyophilization to give the titled compound (0.74 g) as a white amorphous powdery product.

Elemental Analysis for $C_{22}H_{30}N_6O_7 \cdot 0.2H_2O$ Calcd.: C, 53.48; H, 6.20; N, 17.01. Found: C, 53.35; H, 6.19; N, 17.05.

$^1$H-NMR (CD$_3$OD) δ: 2.60–4.65 (20H, m), 3.65 (3H, s), 3.74 (3H, s), 5.12 (1H, t, J=5.8 Hz), 6.63 (1H, t, J=4.8 Hz), 8.35 (1H, d, J=4.8 Hz).

IR (KBr): 1740, 1640 cm$^{-1}$.

Working Example 15

(S)-[3-Methoxycarbonylmethyl-2-oxo-4-[4-oxo-4-(4-pyrimidin-2-ylpiperazin-1-yl)butyryl]piperazin-1-yl]acetic Acid To a suspension of (S)-(3-methoxycarbonylmethyl-2-oxopiperazin-1-yl)acetic acid tert-butyl ester (0.45 g) and 4-oxo-4-(4-pyrimidin-2-ylpiperazin-1-yl)butanoic acid (0.46 g) produced in Reference Example 4 in acetonitrile (20 ml) and dimethylformamide (2 ml) was added 1-ethyl-3-(3-dimethylaminopropyl)carbodiimide hydrochloride (0.36 g) and the suspension was stirred for 15 hours at room temperature. The reaction mixture was concentrated under reduced pressure. To the solution was added saturated brine and the solution was extracted with ethyl acetate. The extract was dried over $Na_2SO_4$ and was concentrated under reduced pressure. To the produced ester derivative was added trifluoroacetic acid (10 ml) and the mixture was stirred for 2 hours at room temperature. The reaction mixture was concentrated under reduced pressure and the concentrate was purified by CHP-20 column chromatography ($H_2O \rightarrow 30\%$ acetonitrile aqueous solution). The objected fraction was concentrated and subjected to lyophilization to give the titled compound (0.45 g) as a white amorphous powdery product.

Elemental Analysis for $C_{21}H_{28}N_6O_7 \cdot 1.25H_2O$ Calcd.: C, 50.55; H, 6.16; N, 16.84. Found: C, 50.46; H, 5.97; N, 16.69.

$^1$H-NMR (CD$_3$OD) δ: 2.60–4.65 (20H, m), 3.65 (3H, s), 5.13 (1H, t, J=5.9 Hz), 6.63 (1H, dd, J=4.6, 4.6 Hz), 8.35 (1H, d, J=4.6 Hz).

IR (KBr): 1730, 1640 cm$^{-1}$.

Working Example 16

(S)-[4-(4-[4,4']-Bipiperidinyl-1-yl-4-oxobutyryl)-3-methoxycarbonylmethyl-2-oxopiperazin-1-yl]acetic Acid To a suspension of (S)-4-(4-tert-butoxycarbonyl-methyl-2-methoxycarbonylmethyl-3-oxopiperazin-1-yl)-4-oxobutanoic acid (0.7 g) and 4,4'-bipiperidine dihydrochloride (0.482 g) in dimethylformamide (30 ml) were added 1-ethyl-3-(3-dimethylaminopropyl)carbodiimide hydrochloride (0.57 g) and triethylamine (0.6 ml) and the suspension was stirred for 24 hours at room temperature. The reaction mixture was concentrated under reduced pressure and the concentrate was dissolved in water (10 ml). The solution was purified by means of CHP-20 column chromatography ($H_2O \rightarrow 30\%$ acetonitrile aqueous solution). To the produced ester derivative was added trifluoroacetic acid (8 ml) and the mixture was stirred for 3 hours at room temperature. The reaction mixture was concentrated under reduced pressure and the concentrate was purified by means of CHP-20 column chromatography ($H_2O \rightarrow 30\%$ acetonitrile aqueous solution). The objected fraction was concentrated and subjected to lyophilization to give the titled compound (0.22 g) as a white amorphous powdery product.

Elemental Analysis for $C_{23}H_{36}N_4O_7 \cdot 0.75H_2O$ Calcd.: C, 51.98; H, 6.54; N, 9.90. Found: C, 52.08; H, 6.18; N, 10.25.

$^1$H-NMR (D$_2$O) δ: 0.90–1.50 (4H, m), 1.58–1.86 (2H, m), 3.62 (3H, s), 5.08 (1H, t, J=6.2 Hz).

IR (KBr): 1736, 1640 cm$^{-1}$.

Working Example 17

(RS,S)-[4-[2-(4-Methoxybenzyl)-4-oxo-4-[4-(pyridin-4-yl)piperazin-1-yl]butyryl]-3-methoxycarbonylmethyl-2-oxopiperazin-1-yl]acetic Acid To a suspension of (S)-(3-methoxycarbonylmethyl-2-oxopiperazin-1-yl)acetic acid tert-butyl ester (0.29 g) and 2-(4-methoxybenzyl)-4-oxo-4-(4-pyridin-4-ylpiperazin-1-yl)butanoic acid (0.385 g) produced in Reference Example 9 in acetonitrile (30 ml) was added 1-ethyl-3-(3-dimethylaminopropyl)carbodiimide hydrochloride (0.4 g) and the suspension was stirred for 24 hours at room temperature. The reaction mixture was concentrated under reduced pressure and purified by means of a silica gel column chromatography (acetonitrile:methanol=7:3). To the produced ester derivative was added trifluoroacetic acid (6 ml) and the solution was stirred for 2 hours at room temperature. The reaction mixture was concentrated under reduced pressure and the concentrate was purified by means of CHP-20 column chromatography ($H_2O \rightarrow 20\%$ acetonitrile aqueous solution). The objected fraction was concentrated and subjected to lyophilization to give the titled compound (0.35 g) as a white amorphous powdery product.

Elemental Analysis for $C_{30}H_{37}N_5O_8 \cdot 2H_2O$ Calcd.: C, 57.04; H, 6.54; N, 11.09. Found: C, 56.81; H, 6.67; N, 11.36.

$^1$H-NMR (D$_2$O) δ: 2.45–4.10 (23H, m), 3.70 (3H, s), 4.20–4.45 (1H, m), 4.89 (1H, m), 6.77 (2H, d, J=8.8 Hz), 6.91 (2H, d, J=7.0 Hz), 7.02 (2H, m); 8.01 (2H, d, J=7.0 Hz).

IR (KBr): 1736, 1640 cm$^{-1}$.

Working Example 18

(RS,S)-[4-[2-(4-Methoxybenzyl)-4-oxo-4-[4-(pyridin-4-yl)piperazin-1-yl]butyryl]-3-methoxycarbonylmethyl-2-oxopiperazin-1-yl]acetic Acid Ethyl Ester By converting (RS,S)-[4-[2-(4-methoxybenzyl)-4-oxo-4-[4-(pyridin-4-yl)piperazin-1-yl]butyryl]-3-methoxycarbonylmethyl-2-oxopiperazin-1-yl]acetic acid into ethyl ester, the titled compound was produced as a white amorphous powdery product(0.5 g).

Elemental Analysis for $C_{32}H_{41}N_5O_8 \cdot CF_3COOH \cdot 1.5H_2O$ Calcd.: C, 53.40; H, 5.93; N, 9.16. Found: C, 53.43; H, 6.18; N, 9.36.

$^1$H-NMR (D$_2$O) δ: 1.20 (3H, t, J=7.1 Hz), 2.30–4.25 (25H, m), 3.75 (3H, s), 4.25–4.55 (1H, m), 4.92 (1H, m), 6.87 (2H, m), 6.98 (2H, d, J=7.4 Hz), 7.13 (2H, m), 8.04 (2H, d, J=7.4 Hz).

IR (KBr): 1736, 1642 cm$^{-1}$.

Working Example 19

(R,S)-[4-[2-tert-Butoxycarbonylamino-4-oxo-4-(4-pyridin-4-ylpiperazin-1-yl)butyryl]-3-methoxycarbonyl-methyl-2-oxopiperazin-1-yl]acetic Acid Tert-butyl Ester A mixture of (R,S)-3-tert-butoxycarbonylamino-4-(4-tert-butoxycarbonylmethyl-2-methoxycarbonylmethyl-3-oxopiperazin-1-yl)-4-oxobutanoic acid benzylester (2.0 g) produced in Reference Example 10, 10% palladium on carbon(0.4 g) and ethyl acetate (20 ml) was stirred for 1 hour under hydrogen atmosphere at room temperature. The catalyst was filtered off and the filtrate was concentrated. The produced carboxylic acid derivative was dissolved in DMF (20 ml). To the solution were added 1-(pyridin-4-yl)-piperazine (0.83 g) and 1-ethyl-3-(3-dimethylamino-propyl) carbodiimide (0.84 g), and the solution was stirred for 3 hours. The reaction solution was poured into a saturated aqueous solution of sodium hydrogen carbonate, extracted with ethyl acetate. The extract solution was dried over anhydrous magnesium sulfate. The solution was concentrated under reduced pressure. The obtained residue was subjected to silica gel column chromatography (eluent:aceton:water=3:1) to give the titled compound (2.0 g) as a white amorphous powdery product.

IR(KBr): 2978, 1740, 1651, 1599, 1441, 1368, 1231, 1161 cm$^{-1}$.

$^1$H NMR (200 MHz, CD$_3$OD) δ: 1.43 (9H, s), 1.47 (9H, s), 2.55–2.75 (1H, m), 2.80–2.93 (2H, m), 2.95–3.18 (1H, m), 3.26–3.94 (11H, m), 3.64 (3H, s), 3.95 (1H, d, J=17.2 Hz), 4.21 (1H, d, J=17.2 Hz), 4.28–4.42 (1H, m), 4.90–5.15 (2H, 30 m), 6.85 (2H, d, J=6.4 Hz), 8.14 (2H, d, J=6.4 Hz).

Working Example 20

(S,S)-[4-[2-tert-Butoxycarbonylamino-4-oxo-4-(4-pyridin-4-ylpiperazin-1-yl)butyryl]-3-methoxycarbonyl-methyl-2-oxopiperazin-1-yl]acetic Acid Tert-butyl Ester In substantially the same manner as in Working Example 19, the titled compound was produced as a white amorphous powdery product (91%).

IR(KBr) : 2978, 1740, 1647, 1597, 1439, 1368, 1233, 1161 cm$^{-1}$.

$^1$H NMR (200 MHz, CD$_3$OD) δ: 1.43 (9H, s), 1.48 (9H, s), 2.55–2.73 (1H, m), 2.90 (2H, d, J=5.8 Hz), 3.03–3.23 (1H, m), 3.35–4.20 (13H, m), 3.65 (3H, s), 4.27–4.42 (1H, m), 4.92–5.13 (2H, m), 6.85 (2H, d, J=6.8 Hz), 8.14 (2H, d, J=6.8 Hz).

Working Example 21

(R,S)-[4-[2-Amino-4-oxo-4-(4-pyridin-4-ylpiperazin-1-yl)butyryl]-3-methoxycarbonylmethyl-2-oxopiperazin-1-yl]acetic Acid Trifluoroacetic Acid Salt To a solution of (R,S)-[4-(2-tert-butoxycarbonyl-amino-4-oxo-4-(4-pyridin-4-ylpiperazin-1-yl)butyryl]-3-methoxycarbonylmethyl-2-oxopiperazin-1-yl]acetic acid tert-butyl ester (2.0 g) produced in Working Example 19 in toluene (10 ml) was added trifluoroacetic acid (10 ml) and the solution was stirred for 1 hour. The reaction mixture was concentrated under reduced pressure and the residue was purified by CHP-20 column chromatography (eluent:H$_2$→5% acetonitrile aqueous solution). The objected fraction was concentrated and subjected to lyophilization to give the titled compound (1.77 g) as a white amorphous powdery product.

Specific Optical Rotation: [α]$_D^{20}$+62.7° (C=1.021, H$_2$O)

Elemental Analysis for C$_{22}$H$_{30}$N$_6$O$_7$·1.5CF$_3$COOH·1.5H$_2$O Calcd.: C, 43.61; H, 5.05; N, 12.20. Found: C, 43.47; H, 5.07; N, 12.37.

IR(KBr): 2953, 1734, 1653, 1545, 1449, 1202, 1132 cm$^{-1}$.

$^1$H NMR (200 MHz, D$_2$O) δ: 2.85–3.25 (4H, m), 3.35–4.35 (14H, m), 3.72 (3H, s), 4.85–5.05 (1H, m), 5.24 (1H, t, J=6.0 Hz), 7.07 (2H, d, J=7.6 Hz), 8.13 (2H, d, J=7.6 Hz).

Working Example 22

(S,S)-[4-[2-Amino-4-oxo-4-(4-pyridin-4-ylpiperazin-1-yl)butyryl]-3-methoxycarbonylmethyl-2-oxopiperazin-1-yl]acetic Acid Trifluoroacetic Acid Salt In substantially the same manner as in Working Example 21, the titled compound (2.44 g, 88%) was produced as a white amorphous powdery product.

Specific Optical Rotation: [α]$_D^{20}$+46.4° (C=1.015, H$_2$O)

Elemental Analysis for C$_{22}$H$_{30}$N$_6$O$_7$·1.7CF$_3$COOH·2H$_2$O Calcd.: C, 42.35; H, 5.00; N, 11.67. Found: C, 42.19; H, 4.86; N, 11.78.

IR(KBr): 2949, 1734, 1653, 1545, 1449, 1202, 1134 cm$^{-1}$.

$^1$H NMR (200 MHz, D$_2$O) δ: 2.95–3.30 (4H, m), 3.40–4.40 (14H, m), 3.74 (3H, s), 4.80–5.00 (1H, m), 5.12 (1H, t, J=5.8 Hz), 7.06 (2H, d, J-7.6 Hz), 8.12 (2H, d, J=7.6 Hz).

Working Example 23

(R,S)-[4-[2-Methoxycarbonylamino-4-oxo-4-(4-pyridin-4-ylpiperazin-1-yl)butyryl]-3-methoxycarbonylmethyl-2-oxopiperazin-1-yl]acetic Acid Hydrochloride To a mixture of (R,S)-[4-[2-amino-4-oxo-4-[4-(pyridin-4-yl)piperazin-1-yl]butyryl]-3-methoxy-carbonylmethyl-2-oxopiperazin-1-yl]acetic acid trifluoroacetic acid salt (0.30 g) produced in Working Example 21, an aqueous solution of sodium hydrogen carbonate (0.18 g), water (3 ml) and 1,4-dioxane (3 ml) was added methyl chloroformate (0.051 ml) and the solution was stirred for 1 hour at room temperature. To the reaction solution was added 1N hydrochloric acid and the solution was adjusted to pH 3, which was then concentrated. The concentrate was purified by means of CHP-20 column chromatography (eluent:H$_2$O→10% acetonitrile aqueous solution). The objected fraction was concentrated and subjected to lyophilization to give the titled compound (0.25 g) as a white amorphous powdery product.

Specific Optical Rotation: [α]$_D^{20}$+91.6° (C=0.504, H$_2$O)

Elemental Analysis for C$_{24}$H$_{32}$N$_6$O$_9$·HCl·H$_2$O Calcd.: C, 47.80; H, 5.85; N, 13.94. Found: C, 47.91; H, 6.18; N, 14.01.

IR(KBr): 1721, 1642, 1545, 1443, 1381, 1289, 1221 cm$^{-1}$.

$^1$H NMR (200 MHz, D$_2$O) δ: 2.76–3.16 (4H, m), 3.32–4.30 (17H, m), 3.69 (3H, s), 4.97–5.10 (1H, m), 5.15 (1H, t, J=6.4 Hz), 7.06 (2H, d, J=7.2 Hz), 8.11 (2H, d, J=7.2 Hz).

Working Example 24

(S,S-[4-[2-Methoxycarbonylamino-4-oxo-4-(4-pyridin-4-ylpiperazin-1-yl)butyryl]-3-methoxycarbonylmethyl-2-oxopiperazin-1-yl]acetic Acid Hydrochloride To a mixture of (S,S)-[4-[2-amino-4-oxo-4-[4-(pyridin-4-yl)piperazin-1-yl]butyryl]-3-methoxy-carbonylmethyl-2-oxopiperazin-1-yl]acetic acid trifluoroacetic acid salt (0.30 g) produced in Working Example 22, an aqueous solution of sodium hydrogen carbonate (0.18 g), water (3 ml) and 1,4-dioxane (3 ml) was added methyl chloroformate (0.048 ml) and the solution was stirred for 1 hour at room temperature. To the reaction solution was added 1N hydrochloric acid and the solution was adjusted to pH 3, which was then concentrated under reduced pressure. The concentrate was purified by means of CHP-20 column chromatography (eluent:H$_2$O→10% acetonitrile aqueous solution). The objected fraction was concentrated and subjected to lyophilization to give the titled compound (0.2 g) as a white amorphous powdery product.

Specific Optical Rotation: [α]$_D^{20}$+20.4° (C=1.003, H$_2$O )

Elemental Analysis for C$_{24}$H$_{32}$N$_6$O$_9$·HCl·1.5H$_2$O Calcd.: C, 47.10; H, 5.93; N, 13.73. Found: C, 47.41; H, 6.19; N, 13.81.

IR(KBr): 1721, 1644, 1545, 1447, 1291, 1221 cm$^{-1}$.

$^1$H NMR (200 MHz, D$_2$O) δ: 2.70–3.16 (4H, m), 3.22–4.00 (15H, m), 3.64 (3H, s), 4.10 (1H, d, J=17.0 Hz), 4.28 (1H, d, J=8.8 Hz), 4.92–5.15 (2H, m), 7.01 (2H, d, J=7.6 Hz), 8.05 (2H, d, J=7.6 Hz).

Working Example 25

(R,S)-[4-[2-Methylthiocarbonylamino-4-oxo-4-(4-pyridin-4-ylpiperazin-1-yl)butyryl]-3-methoxycarbonylmethyl-2-oxopiperazin-1-yl]acetic Acid To a mixture of (R,S)-[4-[2-amino-4-oxo-4-[4-(pyridin-4-yl)piperazin-1-yl]butyryl]-3-methoxy-carbonylmethyl-2-oxopiperazin-1-yl]acetic acid trifluoroacetic acid salt (0.25 g) produced in Working Example 21, an aqueous solution of sodium hydrogen carbonate (0.15 g), water (2.5 ml) and 1,4-dioxane (2.5 ml)was added methyl chlorothioformate (0.047 ml) and the solution was stirred for 1 hour at room temperature. To the reaction solution was added 1N hydrochloric acid and the solution was adjusted to pH 3, which was concentrated under reduced pressure. The concentrate was purified by CHP-20 column chromatography (eluent:H$_2$O→10% acetonitrile aqueous solution). The objected fraction was concentrated and subjected to lyophilization to give the titled compound (0.18 g) as a white amorphous powdery product.

Specific Optical Rotation: $[α]_D^{20}$+105.6° (c=0.506, H$_2$O)

Elemental Analysis for C$_{24}$H$_{32}$N$_6$O$_8$S·2H$_2$O Calcd.: C, 47.99; H, 6.04; N, 13.99. Found: C, 48.19; H, 6.07; N, 14.21.

IR(KBr): 1728, 1642, 1545, 1443, 1381, 1217 cm$^{-1}$.

$^1$H NMR (200 MHz, D$_2$O) δ: 2.32 (3H, s), 2.76–3.18 (4H, m), 3.30–4.24 (14H, m), 3.70 (3H, s), 5.14 (1H, t, J=6.4 Hz), 5.28 (1H, t, J=7.0 Hz), 7.07 (2H, d, J=7.4 Hz), 8.11 (2H, d, J=7.4 Hz).

Working Example 26

(S,S)-[4-[2-Methylthiocarbonylamino-4-oxo-4-(4-pyridin-4-ylpiperazin-1-yl)butyryl]-3-methoxycarbonylmethyl-2-oxopiperazin-1-yl]acetic Acid In substantially the same manner as in Working Example 25, the titled compound (0.18 g, 84%) was produced as a white amorphous powdery product, from the compound produced in Working Example 25 (0.25 g).

Specific Optical Rotation: $[α]_D$+13.7° (C=0.516, H$_2$O)

Elemental Analysis for C$_{24}$H$_{32}$N$_6$O$_8$S·2H$_2$O Calcd.: C, 47.99; H, 6.04; N, 13.99. Found: C, 47.73; H, 6.12; N, 13.93.

IR(KBr): 1732, 1642, 1543, 1441, 1381, 1217 cm$^{-1}$.

$^1$H NMR (200 MHz, D$_2$O) δ: 2.32 (3H, s), 2.78–3.22 (4H, m), 3.30–4.36 (14H, m), 3.70 (3H, s), 5.12 (1H, t, J=6.2 Hz), 5.20–5.33 (1H, m), 7.07 (2H, d, J-7.2 Hz), 8.11 (2H, d, 0 J=7.2 Hz).

Working Example 27

(R,S)-[4-[2-N-Formylamino-4-oxo-4-(4-pyridin-4-ylpiperazin-1-yl)butyryl]-3-methoxycarbonylmethyl-2-oxopiperazin-1-yl]acetic Acid A mixture of formic acid (0.1 ml) and acetic anhydride (0.21 ml) was heated for 2 hours at 60° C. After cooling, to the reaction solution was added tetrahydrofuran (1.5 ml). To the solution was added the compound (0.3 g) produced in Working Example 21 in DMF (1.5 ml) and the solution was stirred for 1.5 hours at room temperature. The reaction mixture was concentrated under reduced pressure and the concentrate was purified by CHP-20 column chromatography (eluent:H$_2$O→10% acetonitrile aqueous solution). The objected fraction was concentrated and subjected to lyophilization to give the titled compound (0.18 g) as a white amorphous powdery product.

Specific Optical Rotation: $[α]_D^{20}$+110.6 (C=0.552, H$_2$O)

Elemental Analysis for C$_{23}$H$_{30}$N$_6$O$_8$·2H$_2$O Calcd.: C, 49.82; H, 6.18; N, 15.15. Found: C, 50.09; H, 6.16; N, 15.15.

IR(KBr): 1732, 1644, 1543, 1445, 1387, 1219 cm$^{-1}$.

$^1$H NMR (200 MHz, D$_2$O) δ: 2.76–3.24 (4H, m), 3.28–3.52 (2H, m), 3.54–4.28 (12H, m), 3.68 (3H, s), 5.14 (1H, t, J=6.2 Hz), 5.35 (1H, dd, J=5.4, 6.0 Hz), 7.05 (2H, d, J=7.6 Hz), 8.10 (2H, d, J=7.6 Hz).

Working Example 28

(R,S)-[4-[2-N,N-Dimethylamino-4-oxo-4-(4-pyridin-4-ylpiperazin-1-yl)butyryl]-3-methoxycarbonylmethyl-2-oxopiperazin-1-yl]acetic Acid Hydrochloride To a solution of (R,S)-[4-[2-amino-4-oxo-4-[4-(pyridin-4-yl)piperazin-1-yl]butyryl]-3-methoxy-carbonylmethyl-2-oxopiperazin-1-yl]acetic acid trifluoroacetic acid salt (0.30 g) produced in Working Example 21, 37% aqueous solution of formaldehyde (0.33 ml) and acetic acid (0.075 ml) in acetonitrile (3 ml) was added sodium cyanoborohydride (0.041 g) and the solution was stirred for 2.5 hours at room temperature. To the reaction solution 1N hydrochloric acid was added and the solution was adjusted to pH 3, which was concentrated under reduced pressure. The concentrate was purified by means of CHP-20 column chromatography (eluent:H$_2$O→10% acetonitrile aqueous solution). The objected fraction was concentrated and subjected to lyophilization to give the titled compound (0.15 g) as a white amorphous powdery product.

Specific Optical Rotation: $[α]_D^{20}$+92.5(C=0.510, H$_2$O)

Elemental Analysis for C$_{24}$H$_{34}$N$_6$O$_7$·HCl·1.1H$_2$O Calcd.: C, 50.15; H, 6.52; N, 14.62. Found: C, 49.94; H, 6.76; N, 14.87.

IR(KBr): 1732, 1644, 1541, 1441, 1381, 1287, 1219 cm$^{-1}$.

$^1$H NMR (200 MHz, D$_2$O) δ: 2.43 (6H, s), 2.70–3.25 (4H, m), 3.30–4.21 (13H, m), 3.69 (3H, s), 4.25–4.45 (2H, m), 5.15 (1H, t, J=6.0 Hz), 7.07 (2H, d, J=7.8 Hz), 8.12 (2H, d, J=7.8 Hz).

Working Example 29

(R,S)-[4-[2-(4-Methoxybenzoylamino)-4-oxo-4-(4-pyrdidn-4-ylpiperazin-1-yl)butyryl]-3-methoxycarbonylmethyl-2-oxopiperazin-1-yl]acetic Acid Hydrochloride To a mixture of (R,S)-[4-[2-amino-4-oxo-4-[4-(pyridin-4-yl)piperazin-1-yl]butyryl]-3-methoxy-carbonylmethyl-2-oxopiperazin-1-yl]acetic acid trifluoroacetic acid salt (0.21 g) produced in Working Example 21 and an aqueous solution of sodium hydrogen carbonate (0.13 g) in water (2.1 ml)-dioxane (2.1 ml) was added 4-methoxybenzoylchloride (0.061 g) and the mixture was stirred for 1 hour at room temperature. The pH of the reaction solution was adjusted to 3 with 1N hydrochloric acid and the solution was concentrated under reduced pressure. The concentrate was purified by means of CHP-20 column chromatography (eluent:$H_2O \rightarrow 5\%$ acetonitrile aqueous solution 10% acetonitrile aqueous solution 15% acetonitrile aqueous solution 30% acetonitrile aqueous solution). The objected fraction was concentrated and subjected to lyophilization to give the titled compound (0.13 g) as a white amorphous powdery product.

Specific Optical Rotation: $[\alpha]_D^{20}$+97.0° (C=1.012, $H_2O$)
Elemental Analysis for $C_{30}H_{36}N_6O_9 \cdot HCl \cdot 1.5H_2O$ Calcd.: C, 52.36; H, 5.86; N, 12.21. Found: C, 52.29; H, 6.08; N, 12.39.
IR(KBr): 2951, 1734, 1638, 1545, 1443, 1256, 1026 cm$^{-1}$.
$^1$H NMR (200 MHz, $D_2O$) δ: 2.80–3.20 (4H, m), 3.25–4.30 (20H, m), 5.19 (1H, t, J=6.2 Hz), 5.47 (1H, t, J=7.0 Hz), 6.98 (2H, d, J=7.4 Hz), 7.03 (2H, d, J=8.8 Hz), 7.78 (2H, d, J=8.8 Hz), 8.09 (2H, d, J=7.4 Hz).

Working Example 30

(S,S)-[4-[2-(4-Methoxybenzoylamino)-4-oxo-4-(4-pyridin-4-ylpiperazin-1-yl)butyryl]-3-methoxycarbonylmethyl-2-oxopiperazin-1-yl]acetic Acid Hydrochloride In substantially the same manner as in Working Example 29, the titled compound (52%) was produced as a white amorphous powdery product.

Specific Optical Rotation: $[\alpha]_D^{20}$+13.9° (C=1.022, $H_2O$)
Elemental Analysis for $C_{30}H_{36}N_6O_9 \cdot HCl \cdot 1.5H_2O$ Calcd.: C, 52.36; H, 5.86; N, 12.21. Found: C, 52.21; H, 6.06; N, 12.33.
IR(KBr): 2951, 1734, 1638, 1539, 1443, 1258, 1026 cm$^{-1}$.
$^1$H NMR (200 MHz, $D_2O$) δ: 2.85–3.30 (4H, m), 3.35–4.40 (20H, m), 5.13 (1H, t, J=5.8 Hz), 5.41 (1H, t, J=6.8 Hz), 6.90–7.10 (4H, m), 7.75 (2H, d, J=8.8 Hz), 8.08 (2H, d, J=7.0 Hz).

Working Example 31

(R,S)-[4-[2-(4-Methoxybenzenesulfonylamino)-4-oxo-4-(4-pyridin-4-ylpiperazin-1-yl)butyryl]-3-methoxycarbonyl-methyl-2-oxopiperazin-1-yl]acetic Acid Trifluoroacetic Acid Salt In substantially the same manner as in Working Example 29, the titled compound (58%) was produced as a white amorphous powdery product.

Specific Optical Rotation: $[\alpha]_D^{20}$+47.60 (C=0.996, $H_2O$)
Elemental Analysis for $C_{29}H_{36}N_6O_{10}S \cdot 0.6CF_3COOH \cdot H_2O$ Calcd.: C, 48.55; H, 5.21; N, 11.25. Found: C, 48.70; H, 5.55; N, 10.86.
IR(KBr): 1732, 1644, 1543, 1445, 1260, 1155, 1028 cm$^{-1}$.
$^1$H NMR (200 MHz, $D_2O$) δ: 2.62–2.88 (4H, m), 3.28–4.18 (14H, m), 3.61 (3H, s), 3.83 (3H, s), 4.50–4.95 (2H, m), 6.97 (2H, d, J=7.8 Hz), 7.07 (2H, d, J=9.0 Hz), 7.75 (2H, d, J=9.0 Hz), 8.05 (2H, d, J=7.8 Hz).

Working Example 32

(R,S)-[4-[2-(4-Fluorobenzenesulfonylamino)-4-oxo-4-(4-pyridin-4-ylpiperazin-1-yl)butyryl]-3-methoxycarbonyl-methyl-2-oxopiperazin-1-yl]acetic Acid In substantially the same manner as in Working Example 29, the titled compound (40%) was produced as a white amorphous powdery product.

Specific Optical Rotation: $[\alpha]_D^{20}$+53.0° (C=0.989, $H_2O$)
Elemental Analysis for $C_{28}H_{33}FN_6O_9S \cdot 3H_2O$ Calcd.: C, 47.86; H, 5.59; N, 11.96. Found: C, 48.19; H, 5.23; N, 11.58.
IR(KBr): 1732, 1644, 1545, 1443, 1221, 1155 cm$^{-1}$.
$^1$H NMR (200 MHz, $D_2O$) δ: 2.65–2.95 (4H, m), 3.20–3.90 (12H, m), 3.62 (3H, s), 3.89 (1H, d, J=17.0 Hz), 4.06 (1H, d, J=17.0 Hz), 4.60–4.83 (2H, m), 7.01 (2H, d, J=7.6 Hz), 7.25–7.40 (2H, m), 7.82–7.95 (2H, m), 8.07 (2H, d, J=7.6 Hz).

Working Example 33

(S,S)-[4-[2-(4-Methoxybenzenesulfonylamino)-4-oxo-4-(4-pyridin-4-ylpiperazin-1-yl)butyryl]-3-methoxycarbonyl-methyl-2-oxopiperazin-1-yl]acetic Acid Hydrochloride In substantially the same manner as in Working Example 29, the titled compound (66%) was produced as a white amorphous powdery product.

Specific Optical Rotation: $[\alpha]_D^{20}$+51.9° (C=0.999, $H_2O$)
Elemental Analysis for $C_{29}H_{36}N_6O_{10}S \cdot HCl \cdot 2H_2O$ Calcd.: C, 47.51; H, 5.64; N, 11.46. Found: C, 47.75; H, 5.73; N, 11.36.
IR(KBr): 1732, 1644, 1545, 1443, 1260, 1157, 1026 cm$^{-1}$.
$^1$H NMR (200 MHz, $D_2O$) δ: 2.35 (1H, dd, J=15.8, 5.4 Hz), 2.52 (1H, dd, J=15.8, 6.6 Hz), 2.66–2.98 (2H, m), 2.98–4.30 (14H, 20 m), 3.69 (3H, s), 3.85 (3H, s), 4.65–4.95 (2H, m), 6.99 (2H, d, J=7.8 Hz), 7.11 (2H, d, J=9.0 Hz), 7.79 (2H, d, J=9.0 Hz), 8.06 (2H, d, J=7.8 Hz).

Working Example 34

(R,S)-[4-[2-(4-Fluorobenzoylamino)-4-oxo-4-(4-pyridin-4-ylpiperazin-1-yl)butyryl]-3-methoxycarbonylmethyl-2-oxopiperazin-1-yl]acetic Acid To a mixture of (R,S)-[4-[2-amino-4-oxo-4-[4-(pyridin-4-yl)piperazin-1-yl]butyryl]-3-methoxy-carbonylmethyl-2-oxopiperazin-1-yl]acetic acid trifluoroacetic acid salt (0.25 g) produced in Working Example 21, an aqueous solution of sodium hydrogen carbonate (0.15 g), water (2.5 ml) and 1,4-dioxane (2.5 ml) was added 4-fluorobenzoyl chloride (0.051 ml) and the solution was stirred for 1 hour at room temperature. The pH of the reaction solution was adjusted to 3 with 1N hydrochloric acid and the solution was concentrated under reduced pressure. The concentrate was purified by means of CHP-20 column chromatography (eluent:$H_2O \rightarrow 15\%$ acetonitrile aqueous solution→20% acetonitrile aqueous solution→25% acetonitrile aqueous solution→30% acetonitrile aqueous solution). The objected fraction was concentrated and subjected to lyophilization to give the titled compound (0.10 g) as a white amorphous powdery product.

Specific Optical Rotation: $[\alpha]_D^{20}$+93.9° (C=1.009, $H_2O$)
Elemental Analysis for $C_{29}H_{33}FN_6O_8 \cdot 3.7H_2O$ Calcd.: C, 51.28; H. 5.99; N, 12.37. Found: C, 51.22; Hg 5.94; N, 12.42.
IR(KBr): 1736, 1644, 1545, 1443, 1223 cm$^{-1}$.
$^1$H NMR (200 MHz, $D_2O$) δ: 2.75–3.22 (4H, m), 3.22–4.27 (14H, m), 3.68 (3H, s), 5.15 (1H, t, J=6.2 Hz), 5.44 (1H, t, J=7.0 Hz), 6.97 (2H, d, J=7.8 Hz), 7.11–7.27 (2H, m), 7.71–7.86 (2H, m), 8.06 (2H, d, J=7.8 Hz).

Working Example 35

(S,S)-[4-[2-(4-Fluorobenzoylamino)-4-oxo-4-(4-pyridin-4-ylpiperazin-1-yl)butyryl]-3-methoxycarbonylmethyl-2-oxopiperazin-1-yl]acetic Acid Hydrochloride In substantially the same manner as in Working Example 34, the titled compound (43%) was produced as a white amorphous powdery product.

Specific Optical Rotation: $[\alpha]_D^{20}$+12.9° (C=0.981, H$_2$O)

Elemental Analysis for C$_{29}$H$_{33}$FN$_6$O$_8$·HCl·H$_2$O Calcd.: C, 52.21; H, 5.44; N, 12.60. Found: C, 52.08; H, 5.57; N, 12.49.

IR(KBr): 1734, 1638, 1541, 1439, 1223 cm$^{-1}$.

$^1$H NMR (200 MHz, D$_2$O) δ: 2.80–3.29 (4H, m), 3.29–4.00 (12H, m), 3.50 (3H, s), 4.05–4.35 (2H, m), 5.08 (1H, t, J=6.0 Hz), 5.36 (1H, t, J=6.6 Hz), 6.97 (2H, d, J=7.6 Hz), 7.10–7.27 (2H, 35 m), 7.64–7.84 (2H, m), 8.04 (2H, d, J=7.6 Hz).

Working Example 36

(S,S)-[4-[2-(4-Methoxybenzylamino)-4-oxo-4-(4-pyridin-4-ylpiperazin-1-yl)butyryll-3-methoxycarbonylmethyl-2-oxopiperazin-1-yl]acetic Acid To a solution of (S,S)-[4-[2-amino-4-oxo-4-[4-(pyridin-4-yl)piperazin-1-yl]butyryl]-3-methoxy-carbonylmethyl-2-oxopiperazin-1-yl]acetic acid trifluoroacetic acid salt (0.3 g) produced in Working Example 22 and 4-methoxybenzaldehyde (0.061 ml) in DMF (3 ml) was added sodium cyanoborohydride (0.034 g) and the solution was stirred for 2 hours at room temperature. To the reaction solution was added 1N hydrochloric acid and the solution was adjusted to pH 3, which was concentrated under reduced pressure. The concentrate was purified by means of CHP-20 column chromatography (eluent:H$_2$O→5% acetonitrile aqueous solution→20% acetonitrile aqueous solution). The objected fraction was concentrated and subjected to lyophilization to give the titled compound (0.1 g) as a white amorphous powdery product.

Specific Optical Rotation: $[\alpha]_D^{20}$+62.7° (C=0.961, H$_2$O)

Elemental Analysis for C$_{30}$H$_{38}$N$_6$O$_8$·2.7H$_2$O Calcd.: C, 54.65; H, 6.63; N, 12.75. Found: C, 54.69; H, 6.78; N, 12.90.

IR(KBr): 2951, 1732, 1642, 1541, 1441, 1246 cm$^{-1}$.

$^1$H NMR (200 MHz, D$_2$O) δ: 2.50–2.96 (4H, m), 3.20–4.25 (16H, m), 3.68 (3H, s), 3.78 (3H, s), 4.70–4.90 (1H, m), 4.98 (1H, t, J=6.2 Hz), 6.85–7.10 (4H, m), 7.27 (2H, d, J=8.8 Hz), 8.05 (2H, d, J=7.6 Hz).

Working Example 37

(R,S)-[4-[2-(4-Methoxybenzylamino)-4-oxo-4-(4-pyridin-4-ylpiperazin-1-yl)butyryl)-3-methoxycarbonylmethyl-2-oxopiperazin-1-yl]acetic Acid Trifluoroacetic Acid Salt In substantially the same manner as in Working Example 36, the titled compound (31%) was produced as a white amorphous powdery product.

Specific Optical Rotation: $[\alpha]_D^{20}$+46.5° (C=0.967, H$_2$O)

Elemental Analysis for C$_{30}$H$_{38}$N$_6$O$_8$·1.5CF$_3$COOH·2H$_2$O Calcd.: C, 48.47; H. 5.36; N, 10.28. Found: C, 48.61; H, 5.23; N, 9.98.

IR(KBr): 2940, 1730, 1645, 1545, 1447, 1250 cm$^{-1}$.

$^1$H NMR (200 MHz, D$_2$O) δ: 2.70–4.45 (23H, m), 3.65 (3H, s), 4.60–5.00 (2H, m), 6.90–7.15 (4H, m), 7.42 (2H, d, J=8.4 Hz), 8.07 (2H, d, J=7.2 Hz).

Working Example 38

(R,S)-[4-[2-Benzylamino-4-oxo-4-[4-(pyridin-4-yl)piperazin-1-yl]butyryl]-3-methoxycarbonylmethyl-2-oxopiperazin-1-yl]acetic Acid To a solution of (R,S)-[4-[2-amino-4-oxo-4-[4-(pyridin-4-yl)piperazin-1-yl]butyryl]-3-methoxy-carbonylmethyl-2-oxopiperazin-1-yl]acetic acid trifluoroacetic acid salt (0.5 g) produced in Working Example 21, benzaldehyde (0.096 ml) and acetic acid (0.125 ml) in acetonitrile (5.0 ml) was added sodium cyanoborohydride (0.091 g) and the solution was stirred for 1 hour at room temperature. To the reaction solution was added 1N hydrochloric acid and the solution was adjusted to pH 3, which was concentrated. The concentrate was purified by means of CHP-20 column chromatography (H$_2$O→15% acetonitrile aqueous solution). The objected fraction was concentrated and subjected to lyophilization to give the titled compound (0.29 g) as a white amorphous powdery product.

$^1$H-NMR (DMSO-d$_6$) δ: 2.54–2.90 (4H, m), 3.10–4.28 (18H, m), 3.53 (3H, s), 4.96 (1H, t, J=6.0 Hz), 6.84 (2H, d, J=6.4 Hz), 7.13–7.35 (5H, m), 8.18 (2H, d, J=6.4 Hz).

IR (KBr): 1732, 1644 cm$^{-1}$.

Working Example 39

(R,S)-[4-[2-(N-Benzyl-N-methylamino)-4-oxo-4-[4-(pyridin-4-yl)piperazin-1-yl]butyryl]-3-methoxycarbonylmethyl-2-oxopiperazin-1-yl]acetic Acid To a solution of (R,S)-[4-[2-benzylamino-4-oxo-4-[4-(pyridin-4-yl)piperazin-1-yl]butyryl]-3-methoxy-carbonylmethyl-2-oxopiperazin-1-yl]acetic acid (0.29 g) produced in Working Example 38, 37% aqueous solution of formaldehyde (0.37 ml) and acetic acid (0.086 ml) in acetonitrile (2.9 ml) was added sodium cyanoborohydride (0.047 g) and the solution was stirred for 4 hours at room temperature. To the reaction solution was added 1N hydrochloric acid and the solution was adjusted to pH 3, which was concentrated. The concentrate was purified by means of CHP-20 column chromatography (H$_2$O→15% acetonitrile aqueous solution). The objected fraction was concentrated and subjected to lyophilization to give the titled compound (0.28 g) as a white amorphous powdery product.

$^1$H-NMR (CD$_3$OD) δ: 2.45 (3H, s), 2.54–2.70 (1H, m), 2.70–2.94 (4H, m), 3.10–4.10 (16H, m), 3.59 (3H, s), 4.12 (1H, d, J=16.8 Hz), 4.18–4.30 (1H, m), 5.10 (1H, t, J=6.0 Hz), 7.12 (2H, d, J=7.4 Hz), 7.18–7.40 (5H, m), 8.16 (2H, d, J=7.4 Hz).

IR (KBr): 1736, 1640 cm$^{-1}$.

Working Example 40

(S,R)-(3-Methoxycarbonylmethyl-4-(2-N-methylamino-4-oxo-4-[4-(pyridin-4-yl)piperazin-1-yl]butyryl]-2-oxo-piperazin-1-yl]acetic Acid To a solution of (R,S)-[4-[2-(N-benzyl-N-methylamino)-4-oxo-4-[4-(pyridin-4-yl)piperazin-1-yl]butyryl]-3-methoxycarbonylmethyl-2-oxopiperazin-1-yl]acetic acid (0.28 g) produced in Working Example 39 and 1N hydrochloric acid (0.47 ml) in methanol (2.8 ml) was added 10% palladium on carbon (0.056 g) and the solution was stirred for 3 hours under hydrogen atmosphere. The catalyst was filtered off and the filtrate concentrated. The concentrate was purified by means of CHP-20 column chromatography (eluent:H$_2$O). The objected fraction was concentrated and subjected to lyophilization to give the titled compound (0.26 g) as a white amorphous powdery product.

Specific Optical Rotation: $[\alpha]_D^{20}$+78.9° (C=0.510, H$_2$O)

Elemental Analysis for C$_{23}$H$_{32}$N$_6$O$_7$·5H$_2$O Calcd.: C, 46.46; H, 7.12; N, 14.13. Found: C,46.14; H. 7.13; N, 14.14.

$^1$H-NMR (D$_2$O) δ: 2.78 (3H, s), 2.84–3.08 (2H, m), 3.08–3.26 (2H, m), 3.30–5.05 (15H, m), 3.68 (3H, s), 5.22 (1H, t, J=6.2 Hz), 7.05 (2H, d, J=7.8 Hz), 8.10 (2H, d, J=7.8 Hz).

IR (KBr): 1732, 1645 cm$^{-1}$.

Working Example 41

(R,S)-[4-[2-(1-Acetoxyethoxycarbonylamino)-4-oxo-4-[4-(pyridin-4-yl)piperazin-1-yl]butyryl]-3-methoxy-carbonylmethyl-2-oxopiperazin-1-yl]acetic Acid A solution of (R,S)-[4-[2-amino-4-oxo-4-(pyridin-4-yl)piperazin-1-yl]butyryl]-3-methoxycarbonylmethyl-2-oxopiperazin-1-yl]acetic acid trifluoroacetic acid salt (0.5 g) produced in Working Example 21, α-acetoxyethyl p-nitrophenylcarbonate (0.49 g), HOBt (0.14 g) and N-methylmorpholin (0.12 ml) in dimethylformamide (5.0 ml) was stirred for 1 hour at room temperature for 1 hour. To the reaction solution was added 1N hydrochloric acid and the solution was adjusted to pH 3, which was concentrated. The concentrate was purified by means of CHP-20 column chromatography ($H_2O \rightarrow 10\%$ acetonitrile aqueous solution). The objected fraction was concentrated and subjected to lyophilization to give the titled compound (0.16 g) as a white amorphous powdery product.

Specific Optical Rotation: $[\alpha]_D^{20}$+86.4° (C=0.507, $H_2O$)

Elemental Analysis for $C_{27}H_{36}N_6O_{11} \cdot 2.5H_2O$ Calcd.: C,48.72; H, 6.21; N, 12.63. Found: C,48.55; H, 6.03; N, 12.51.

$^1$H-NMR ($D_2O$) δ: 1.48 (3H, d, J=5.4 Hz), 2.08 and 2.10 (3H, s), 2.74–3.20 (4H, m), 3.30–4.25 (14H, m), 3.69 (3H, s), 4.98–5.20 (2H, m), 6.66–6.80 (1H, m), 7.07 (2H, d, J=7.4 Hz), 8.11 (2H, d, J=7.4 Hz).

IR (KBr): 1736, 1644 $cm^{-1}$.

Working Example 42

(S,R)-[3-Methoxycarbonylmethyl-4-[2-(nicotinyloxy-methoxycarbonylamino)-4-oxo-4-[4-(pyridin-4-yl)-piperazin-1-yl]butyryl]-2-oxopiperazin-1-yl]acetic Acid A solution of (R,S)-[4-[2-amino-4-oxo-4-[4-(pyridin-4-yl)piperazin-1-yl]butyryl]-3-methoxy-carbonylmethyl-2-oxopiperazin-1-yl]acetic acid trifluoroacetic acid salt (0.5 g) produced in Working Example 21, nicotinoyloxymethyl p-nitrophenylcarbonate (0.39 g), HOBt (0.14 g) and N-methylmorpholin (0.12 ml) in 15 dimethylformamide (5.0 ml) was stirred at room temperature for 1 hour. To the reaction solution was added 1N hydrochloric acid and the solution was adjusted to pH 3, which was concentrated. The concentrate was purified by means of CHP-20 column chromatography ($H_2O$+15% acetonitrile aqueous solution). The objected fraction was concentrated and subjected to lyophilization to give the titled compound (0.18 g) as a white amorphous powdery product.

Elemental Analysis for $C_{30}H_{35}N_7O_{11} \cdot 3.5H_2O$ Calcd.: C,49.18; H, 5.78; N, 13.38. Found: C,49.47; H, 5.52; N, 13.53.

$^1$H-NMR ($D_2O$) δ: 2.65–3.10 (4H, m), 3.20–4.25 (14H, m), 3.69 (3H, m), 5.00–5.21 (2H, m), 5.92–6.10 (2H, m), 6.95 (2H, d, J=7.4 Hz), 7.52–7.70 (1H, m), 8.08 (2H, d, J=7.4 Hz), 8.42 (1H, dt, J=1.8, 8.0 Hz), 8.71 (1H, d, J=4.2 Hz), 9.10 (1H, s).

IR (KBr): 1738, 1644 $cm^{-1}$.

Working Example 43

(S, R)-[3-Methoxycarbonylmethyl-2-oxo-4-[4-oxo-2-N-pivaloyloxymethoxycarbonylamino-4-(4-pyridin-4-yl-piperazin-1-yl)butyryl]piperazin-1-yl]acetic Acid Hydrochloride In substantially the same manner as in Working Example 41, the titled compound (yield 16%) was produced as a colorless amorphous powder, by using the compound produced in Working Example 21.

Elemental Analysis for $C_{29}H_{40}N_6O_{11} \cdot 1.0HCl \cdot 1.5H_2O$ Calcd.: C,48.91; H,6.23; N,11.80. Found: C,48.88; H,6.22; N,11.88.

$^1$H NMR(200 MHz, $D_2O$) δ: 1.17 (9H, s), 2.68–3.20 (4H, m), 3.30–4.44 (14H, m), 3.70 (3H, s), 4.96–5.22 (2H, m), 5.58–5.82 (2H, m), 7.06 (2H, d, J=7.6 Hz), 8.10 (2H, d, J=7.6 Hz).

IR(KBr): 1745, 1646, 1540, 1442, 1220 $cm^{-1}$.

Working Example 44

(S,S)-[4-[2-Acetoxy-4-oxo-4-(pyridin-4-ylpiperazin-1-yl)butyryl]-3-methoxycarbonylmethyl-2-oxopiperazin-1-yl]acetic Acid To a solution of (S)-(3-methoxycarbonylmethyl-2-oxopiperazin-1-yl)acetic acid tert-butyl ester (0.29 g) in acetonitrile (20 ml) was added 3-acetoxy-2,5-dioxo-tetrahydrofuran (0.24 g) and the solution was stirred for 2 hours at room temperature. The solution was concentrated to remive acetonitrile. To the residue was added ethyl acetate and water. The organic layer was washed with saturated brine and dried over $Na_2SO_4$. The solution was concentrated under reduced pressure and the residue was dissolved in acetonitrile (30 ml). To the solution were added 1-(4-pyridyl)piperazine (0.164 g) and 1-ethyl-3-(3-dimethylaminopropyl)carbodiimide hydrochloride (0.30 g) and the solution was stirred for 5 hours at room temperature. The solution was concentrated to remove acetonitrile. The residue was dissolved in water (10 ml) and purified by means of CHP-20 column chromatography ($H_2O \rightarrow 40\%$ acetonitrile aqueous solution). To the produced tert-butyl ester derivative (0.18 g) was added trifluoroacetic acid (6 ml) and the solution was stirred for 2 hours at room temperature. The reaction solution was concentrated and the residue was dissolved in water (10 ml), which was purified by means of CHP-20 column chromatography ($H_2O \rightarrow$+10% acetonitrile aqueous solution). The objected fraction was concentrated and subjected to lyophilization to give the titled compound (0.10 g) as a white amorphous powdery product.

Elemental Analysis for $C_{24}H_{31}N_5O_9 \cdot 2.25H_2O$ Calcd.: C, 50.21; H, 6.23; N, 12.20. Found: C, 50.26; H, 5.93; N, 12.05.

$^1$H-NMR ($CD_3OD$) δ: 2.07 (3H, s), 2.74–4.40 (18H, m), 3.64 (3H, s), 5.06 (1H, t, J=5.9 Hz), 5.83 (1H, t, J=6.6 Hz), 7.13 (2H, d, J=7.4 Hz), 8.17 (2H, d, J=7.4 Hz).

IR(KBr): 1735, 1643 $cm^{-1}$.

Working Example 45

(S,S)-[4-[2-Hydroxy-4-oxo-4-[4-(pyridin-4-yl)piperazin-1-yl]butyryl]-3-methoxycarbonylmethyl-2-oxopiperazin-1-yl]acetic Acid To a suspension of (S)-(3-methoxycarbonylmethyl-2-oxopiperazin-1-yl)acetic acid tert-butyl ester (0.29 g) and 2-hydroxy-4-oxo-4-(4-pyridin-4-ylpiperazin-1-yl)-butanoic acid (0.30 g) in dimethylformamide (15 ml) was added 1-ethyl-3-(3-dimethylaminopropyl)carbodiimide hydrochloride (0.30 g) and the solution was stirred for 24 hours at room temperature. The solution was concentrated to remove dimethylformamide and the residue was purified by means of CHP-20 column chromatography ($H_2O \rightarrow 30\%$ acetonitrile aqueous solution). To the produced tert-butyl ester derivative (0.20 g) was added trifluoroacetic acid (6 ml) and the solution was stirred for 1 hour at room temperature. The reaction solution was concentrated and the residue was dissolved in water (10 ml), which was purified by means of CHP-20 column chromatography (H$_2$O→5% acetonitrile aqueous solution). The objected fraction was concentrated and subjected to lyophilization to give the titled compound (0.08 g) as a white amorphous powdery product.

Elemental Analysis for C$_{22}$H$_{29}$N$_5$O$_8$·3H$_2$O Calcd.: C, 48.44; H, 6.47; N, 12.84. Found: C, 48.14; H, 6.18; N, 12.64.

$^1$H-NMR(CD$_3$OD) δ: 2.70–4.60 (18H, m), 3.65 (3H, s), 5.10 (1H, t, J=5.9 Hz), 5.34 (1H, t, J=6.3 Hz), 7.13 (2H, d, J=7.2 Hz), 8.17 (2H, d, J=7.2 Hz).

IR (KBr): 1735, 1641 cm$^{-1}$.

Working Example 46

(R,S)-[4-[2-N-Ethylamino-4-oxo-4-(4-pyridin-4-yl-piperazin-1-yl)butyryl]-3-methoxycarbonylmethyl-2-oxopiperazin-1-yl]acetic Acid Hydrochloride In substantially the same manner as in Working Example 40, the titled compound (yield 41%) was produced as a colorless amorphous powder, by using the compound produced in Working Example 39.

Elemental Analysis for C$_{24}$H$_{34}$N$_6$O$_7$·1.0HCl·1.0H$_2$O Calcd.: C,50.30; H,6.51; N,14.67. Found: C,50.07; H,6.59; N,14.95.

$^1$H NMR(200 MHz, D$_2$O) δ: 1.11 (3H, t, J=7.2 Hz), 2.66 (2H, q, J=7.2 Hz), 2.76–3.06 (4H, m), 3.06–4.00 (12H, m), 3.69 (3H, s), 4.10 (1H, d, J=17.2 Hz), 4.22–4.48 (2H, m), 5.19 (1H, t, J=6.0 Hz), 7.05 (2H, d, J=7.6 Hz), 8.11 (2H, d, J=7.6 Hz).

IR(KBr): 1733, 1646, 1600, 1540, 1448, 1386, 1222.

Working Example 47

(S,R)-[3-Methoxycarbonylmethyl-2-oxo-4-[4-oxo-2-N-propylamino-4-(4-pyridin-4-ylpiperazin-1-yl) butyryl]-piperazin-1-yl]acetic Acid Hydrochloride In substantially the same manner as in Working Example 40, the titled compound (yield 45%) was produced as a colorless amorphous powder, by using the compound produced in Working Example 39.

Elemental Analysis for C$_{25}$H$_{36}$N$_6$O$_7$·1.0HCl·1.0H$_2$O Calcd.: C, 51.15; H, 6.70; N, 14.32. Found: C, 51.27; H, 6.89; N, 14.34.

$^1$H NMR (200 MHz, D$_2$O) δ: 0.90 (3H, t, J=7.2 Hz), 1.34–1.62 (2H, m), 2.38–2.64 (2H, m), 2.70–3.06 (4H, m), 3.06–3.92 (11H, m), 3.69 (3H, s), 3.92 (1H, d, J=17.0 Hz), 4.09 (1H, d, J=17.0 Hz), 4.20–4.44 (2H, m), 5.18 (1H, t, J=6.0 Hz), 7.04 (2H, d, J=7.2 Hz), 8.11 (2H, d, J=7.2 Hz).

IR(KBr): 1733, 1646, 1602, 1540, 1448, 1386, 1220 cm$^{-1}$.

Industrial Applicability

The present invention provides compounds and medicines effective for prophylaxis and therapy of various diseases by controlling or inhibiting cell-adhesion. Especially, the compounds of this invention perform platelet aggregation action without remarkable elongation of hemorrhagic period and can be used as a safe and long-acting antithrombotic drug, as compared with known substances showing the same activity.

What is claimed is:
1. A compound of the formula:

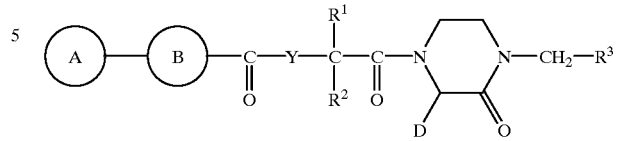

wherein the ring A is a basic 5- to 7-membered heterocyclic group which may be substituted; the ring B is a divalent 5- to 7-membered nitrogen containing heterocyclic group which may be substituted or a divalent 5- to 7-membered cyclic hydrocarbon group which may be substituted; Y is an optionally substituted methylene group; R$^1$ is a hydrogen atom, an optionally substituted hydroxy group, an optionally substituted amino group or an optionally substituted hydrocarbon group which may be bound through a carbonyl group, a thio group, a sulfinyl group or a sulfonyl group; R$^2$ is a hydrogen atom or an optionally substituted hydrocarbon group; R$^3$ is an optionally esterified or amidated carboxyl group; and D is a lower alkyl group substituted with an optionally esterified carboxyl group; or a salt thereof.

2. A compound according to claim 1, wherein the ring A is a basic 5- to 7-membered heterocyclic group containing, besides carbon atoms, 1 to 3 hetero-atoms selected from oxygen atom, sulfur atom and nitrogen atom, which may have 1 to 5 substituents selected from the class consisting of (1) a C$_{1-6}$ alkyl group, (2) a C$_{2-6}$ alkenyl group, (3) a C$_{2-6}$ alkynyl group, (4) a C$_{3-8}$ cycloalkyl group, (5) a C$_{3-8}$ cycloalkenyl group, (6) a C$_{7-12}$ aralkyl group, (7) a C$_{6-10}$ aryl group, (8) a C$_{1-6}$ alkoxy group, (9) a phenoxy group, (10) a C$_{1-6}$ alkanoyl group, (11) a benzoyl group, (12) a C$_{1-6}$ alkanoyloxy group, a benzoyloxy group, (13) a carboxyl group, (14) a C$_{1-6}$ alkoxy-carbonyl group, (15) a carbamoyl group, (16) a N-mono-C$_{1-6}$ alkyl-carbamoyl group, (17) a N,N-di-C$_{1-6}$ alkyl-carbamoyl group, (18) a cyclic amino-carbonyl group, (19) a halogen atom, (20) a halogeno C$_{1-6}$ alkyl group, (21) an oxo group, (22) an amidino group, (23) an imino group, (24) an amino group, (25) a mono-C$_{1-6}$ alkylamino group, (26) a di-C$_{1-6}$ alkylamino group, (27) a 3- to 6-membered cyclic amino group, (28) a C$_{1-6}$ alkanoylamido group, (29) a benzamido group, (30) a carbamoylamino group, (31) a N-mono-C$_{1-6}$ alkyl-carbamoylamino group, (32) a N,N-di-C$_{1-6}$ alkyl-carbamoylamino group, (33) a C$_{1-3}$ alkylenedioxy group, (34) a sulfamoyl group, (35) a C$_{1-6}$ alkylsulfamoyl group, (36) a di-C$_{1-6}$ alkylsulfamoyl group, (37) a C$_{1-6}$ alkylthio group, (38) a C$_{6-10}$ arylthio group, (39) a C$_{1-6}$ alkylsulfinyl group, (40) a C$_{6-10}$ arylsulfinyl group, (41) a C$_{1-6}$ alkylsulfonyl group and (42) a C$_{6-10}$ arylsulfonyl group;

the ring B is (A) a divalent 5- to 7-membered nitrogen containing heterocyclic group which contains, besides carbon atoms, 1 to 3 nitrogen atoms and which may have 1 to 5 substituents selected from the class consisting of (1) a C$_{1-6}$ alkyl group, (2) a C$_{2-6}$ alkenyl group, (3) a C$_{2-6}$ alkynyl group, (4) a C$_{3-8}$ cycloalkyl group, (5) a C$_{3-8}$ cycloalkenyl group, (6) a C$_{7-12}$ aralkyl group, (7) a C$_{6-10}$ aryl group, (8) a C$_{1-6}$ alkoxy group, (9) a phenoxy group, (10) a C$_{1-6}$ alkanoyl group, (11) a benzoyl group, (12) a C$_{1-6}$ alkanoyloxy group, a benzoyloxy group, (13) a carboxyl group, (14) a C$_{1-6}$ alkoxy-carbonyl group, (15) a carbamoyl group, (16) a N-mono-C$_{1-6}$ alkyl-carbamoyl group, (17) a N,N-di-C$_{1-6}$ alkyl-carbamoyl group, (18) a cyclic amino-carbonyl group, (19) a halogen atom, (20) a halogeno $C_{1-6}$ alkyl group, (21) an oxo group, (22) an amidino group, (23) an imino group, (24) an amino group, (25) a mono-$C_{1-6}$ alkylamino group, (26) a di-$C_{1-6}$ alkylamino group, (27) a 3- to 6-membered cyclic amino group, (28) a $C_{1-6}$ alkanoylamido group, (29) a benzamido group, (30) a carbamoylamino group, (31) a N-mono-$C_{1-6}$ alkyl-carbamoylamino group, (32) a N,N-di-$C_{1-6}$ alkyl-carbamoylamino group, (33) a $C_{1-3}$ alkylenedioxy group, (34) a sulfamoyl group, (35) a $C_{1-6}$ alkylsulfamoyl group, (36) a di-$C_{1-6}$ alkylsulfamoyl group, (37) a $C_{1-6}$ alkylthio group, (38) a $C_{6-10}$ arylthio group, (39) a $C_{1-6}$ alkylsulfinyl group, (40) a $C_{6-10}$ arylsulfinyl group, (41) a $C_{1-6}$ alkyl-sulfonyl group and (42) a $C_{6-10}$ arylsulfonyl group, or (B) a divalent 5- to 7-membered cyclic hydrocarbon group which may have 1 to 5 substituents selected from the class consisting of (1) a $C_{1-6}$ alkyl group, (2) a $C_{3-8}$ cycloalkyl group, (3) a $C_{2-6}$ alkenyl group, (4) a $C_{2-6}$ alkynyl group, (5) a $C_{3-8}$ cycloalkenyl group, (6) a $C_{6-10}$ aryl group, (7) a $C_{7-12}$ aralkyl group, (8) a nitro group, (9) an oxo group, (10) a thioxo group, (11) a cyano group, (12) a carbamoyl group, (13) a carboxyl group, (14) a $C_{1-6}$ alkoxy-carbonyl group, (15) a sulfo group, (16) a halogen atom, (17) a $C_{1-4}$ alkoxy group, (19) a $C_{6-10}$ aryloxy group, (20) a $C_{1-4}$ alkylthio group, (21) a $C_{6-10}$ arylthio group, (22) a $C_{1-6}$ alkylsulfinyl group, (23) a $C_{6-10}$ arylsulfinyl group, (24) a $C_{1-6}$ alkyl-sulfonyl group, (25) a $C_{6-10}$ arylsulfonyl group, (26) an amino group, (27) a $C_{1-6}$ alkanoylamino group, benzoylamino, (28) a mono- or di-$C_{1-6}$ alkylamino group, (29) a $C_{3-8}$ cyclo-alkylamino group, (30) a $C_{6-10}$ arylamino group, (31) a $C_{1-6}$ acyl group, (32) a $C_{6-10}$ aryl-carbonyl group and (33) 5- to 6-membered heterocyclic groups containing, besides carbon atoms, 1 to 3 hetero-atoms selected from oxygen atom, sulfur atom and nitrogen atom;

Y is a methylene group which may have 1 or 2 substituents selected from the class consisting of (1) a halogen atom, (2) a hydroxy group, (3) an oxo group, (4) a $C_{1-6}$ alkoxy group, (5) a di-$C_{1-6}$ alkylamino group, (6) a $C_{1-6}$ alkyl group substituted with 1 to 3 halogen atoms, (7) a $C_{1-6}$ acyl group, (8) a hydroxy-$C_{1-6}$ alkyl group, (9) a $C_{1-6}$ alkoxy-$C_{1-6}$ alkyl group and (10) a $C_{1-6}$ alkoxy-carbonyl group;

$R^1$ is (A) a hydrogen atom, (B) a hydroxy group optionally substituted by (1) a $C_{1-6}$ alkyl group which may have 1 to 4 substituents selected from the class consisting of a halogen atom, a $C_{6-10}$ aryl group, a $C_{7-12}$ aralkyl group and a nitro group, (2) a $C_{6-10}$ aryl group which may have 1 to 4 substituents selected from the class consisting of a halogen atom, a $C_{1-6}$ alkyl group, a $C_{6-10}$ aryl group, a $C_{7-12}$ aralkyl group and a nitro group, (3) a $C_{7-12}$ aralkyl group which may have 1 to 4 substituents selected from the class consisting of a halogen atom, a $C_{1-6}$ alkyl group, a $C_{6-10}$ aryl group, a $C_{7-12}$ aralkyl group and a nitro group, (4) a formyl group, (5) a $C_{1-6}$ alkyl-carbonyl group which may have 1 to 4 substituents selected from the class consisting of a halogen atom, a $C_{1-6}$ alkyl group, a $C_{6-10}$ aryl group, a $C_{7-12}$ aralkyl group and a nitro group, (6) a $C_{6-10}$ aryloxy-carbonyl group which may have 1 to 4 substituents selected from the class consisting of a halogen atom, a $C_{1-6}$ alkyl group, a $C_{6-10}$ aryl group, a $C_{7-12}$ aralkyl group and a nitro group, (7) a $C_{6-10}$ arylcarbonyl group which may have 1 to 4 substituents selected from the class consisting of a halogen atom, a $C_{1-6}$ alkyl group, a $C_{6-10}$ aryl group, a $C_{7-12}$ aralkyl group and a nitro group, (8) a 5-membered aromatic heterocyclic group which may have 1 to 4 substituents selected from the class consisting of a halogen atom, a $C_{1-6}$ alkyl group, a $C_{6-10}$ aryl group, a $C_{7-12}$ aralkyl group and a nitro group, or (10) a tri-$C_{1-4}$ alkylsilyl, (C) an amino group which may have 1 or 2 substituents selected from the class consisting of (C-1) an optionally substituted hydrocarbon group selected from the class consisting of (i) a $C_{1-6}$ alkyl group, (ii) a $C_{3-8}$ cycloalkyl group, (iii) a $C_{2-6}$ alkenyl group, (iv) a $C_{2-6}$ alkynyl group, (v) a $C_{3-8}$ cycloalkenyl group, (vi) a $C_{6-10}$ aryl group and (vii) a $C_{7-12}$ aralkyl group, each of said hydrocarbon group being unsubstituted or substituted by 1 to 4 substituents selected from the class consisting of (1) a nitro group, (2) a hydroxy group, (3) an oxo group, (4) a thioxo group, (5) a cyano group, (6) a carbamoyl group, (7) a carboxyl group, (8) a $C_{1-6}$ alkoxy-carbonyl group, (9) a halogen atom, (10) a $C_{1-6}$ alkoxy group, (11) a phenoxy group, (12) a phenoxy group substituted with 1 to 3 halogen atoms, (13) a $C_{1-6}$ alkylthio group, (14) a phenylthio group, (15) a $C_{1-6}$ alkylsulfinyl group, (16) a $C_{1-6}$ alkylsulfonyl group, (17) an amino group, (18) a $C_{1-6}$ alkanoylamino group, (19) a mono- or di-$C_{1-6}$ alkylamino group, (20) a $C_{1-6}$ acyl group, (21) a benzoyl group, (22) a 5- to 6-membered heterocyclic group containing, besides carbon atoms, 1 to 3 hetero-atoms selected from oxygen atom, sulfur atom and nitrogen atom which may have 1 to 4 substituents selected from the class consisting of (a) a halogen atom, (b) a $C_{1-6}$ alkyl group and (c) a phenoxy group substituted with 1 to 3 halogen atoms, (23) a $C_{1-6}$ alkyl group substituted with 1 to 3 halogen atoms, (24) a $C_{1-6}$ alkyl group and (25) a $C_{3-8}$ cycloalkyl group, and (C-2) an acyl group represented by the formula:

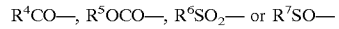

$R^4CO-$, $R^5OCO-$, $R^6SO_2-$ or $R^7SO-$ wherein $R^4$, $R^5$, $R^6$ and $R^7$ are independently (C-2-1) an optionally substituted hydrocarbon group selected from the class consisting of (i) a $C_{1-6}$ alkyl group, (ii) a $C_{3-8}$ cycloalkyl group, (iii) a $C_{2-6}$ alkenyl group, (iv) a $C_{2-6}$ alkynyl group, (v) a $C_{3-8}$ cycloalkenyl group, (vi) a $C_{6-10}$ aryl group and (vii) a $C_{7-12}$ aralkyl group, each of said hydrocarbon group being unsubstituted or substituted by 1 to 4 substituents selected from the class consisting of (1) a nitro group, (2) a hydroxy group, (3) an oxo group, (4) a thioxo group, (5) a cyano group, (6) a carbamoyl group, (7) a carboxyl group, (8) a $C_{1-6}$ alkoxy-carbonyl group, (9) a halogen atom, (10) a $C_{1-6}$ alkoxy group, (11) a phenoxy group, (12) a phenoxy group substituted with 1 to 3 halogen atoms, (13) a $C_{1-6}$ alkylthio group, (14) a phenylthio, (15) a $C_{1-6}$ alkylsulfinyl group, (16) a $C_{1-6}$ alkylsulfonyl group, (17) an amino group, (18) a $C_{1-6}$ alkanoylamino, (19) a mono- or di-$C_{1-6}$ alkylamino group, (20) a $C_{1-6}$ acyl group, (21) a benzoyl group, (22) a 5- to 6-membered heterocyclic group containing, besides carbon atoms, 1 to 3 hetero-atoms selected from oxygen atom, sulfur atom and nitrogen atom which may have 1 to 4 substituents selected from the class consisting of (a) a halogen atom, (b) a $C_{1-6}$ alkyl group and (c) a phenoxy group substituted with 1 to 3 halogen atoms, (23) a $C_{1-6}$ alkyl group substituted with 1 to 3 halogen atoms, (24) a $C_{1-6}$ alkyl group and (25) a $C_{3-8}$ cycloalkyl group, or (C-2-2) a basic 5- to 7-membered heterocyclic group containing, besides carbon atoms, 1 to 3 hetero-atoms selected from oxygen atom, sulfur atom and nitrogen atom, which may have 1 to 5 substituents selected from the class consisting of (1) a $C_{1-6}$ alkyl group, (2) a $C_{2-6}$ alkenyl group, (3) a $C_{2-6}$ alkynyl group, (4) a $C_{3-8}$ cycloalkyl group, (5) a $C_{3-8}$ cycloalkenyl group, (6) a $C_{7-12}$ aralkyl group, (7) a $C_{6-10}$ aryl group, (8) a $C_{1-6}$ alkoxy group, (9) a phenoxy group, (10) a $C_{1-6}$ alkanoyl group, (11) a benzoyl group, (12) a $C_{1-6}$ alkanoyloxy group, a benzoyloxy group, (13) a carboxyl group, (14) a $C_{1-6}$ alkoxy-carbonyl group, (15) a carbamoyl group, (16) a N-mono-$C_{1-6}$ alkyl-carbamoyl group, (17) a N,N-di-$C_{1-6}$ alkyl-carbamoyl group, (18) a cyclic amino-carbonyl group, (19) a halogen atom, (20) a halogeno $C_{1-6}$ alkyl group, (21) an oxo group, (22) an amidino group, (23) an imino group, (24) an amino group, (25) a mono-$C_{1-6}$ alkylamino group, (26) a di-$C_{1-6}$ alkylamino group, (27) a 3- to 6-membered cyclic amino group, (28) a $C_{1-6}$ alkanoylamido group, (29) a benzamido group, (30) a carbamoylamino group, (31) a N-mono-$C_{1-6}$ alkyl-carbamoylamino group, (32) a N,N-di-$C_{1-6}$ alkyl-carbamoylamino group, (33) a $C_{1-3}$ alkylenedioxy group, (34) a sulfamoyl group, (35) a $C_{1-6}$ alkylsulfamoyl group, (36) a di-$C_{1-6}$ alkylsulfamoyl group, (37) a $C_{1-6}$ alkylthio group, (38) a $C_{6-10}$ arylthio group, (39) a $C_{1-6}$ alkylsulfinyl group, (40) a $C_{6-10}$ arylsulfinyl group, (41) a $C_{1-6}$ alkylsulfonyl group and (42) a $C_{6-10}$ arylsulfonyl group, or (D) a hydrocarbon group which may be bound through a carbonyl group, a thio group, a sulfinyl group or a sulfonyl group, said hydrocarbon group being selected from the class consisting of (i) a $C_{1-6}$ alkyl group, (ii) a $C_{3-8}$ cycloalkyl group, (iii) a $C_{2-6}$ alkenyl group, (iv) a $C_{2-6}$ alkynyl group, (v) a $C_{3-8}$ cycloalkenyl group, (vi) a $C_{6-10}$ aryl group and (vii) a $C_{7-12}$ aralkyl group, and each of said hydrocarbon group being unsubstituted or substituted by 1 to 4 substituents selected from the class consisting of (1) a nitro group, (2) a hydroxy group, (3) an oxo group, (4) a thioxo group, (5) a cyano group, (6) a carbamoyl group, (7) a carboxyl group, (8) a $C_{1-6}$ alkoxy-carbonyl group, (9) a halogen atom, (10) a $C_{1-6}$ alkoxygroup, (11) aphenoxygroup, (12) a phenoxy group substituted with 1 to 3 halogen atoms, (13) a $C_{1-6}$ alkylthio group, (14) a phenylthio group, (15) a $C_{16}$ alkylsulfinyl group, (16) a $C_{1-6}$ alkylsulfonyl group, (17) an amino group, (18) a $C_{1-6}$ alkanoylamino group, (19) a mono- or di-$C_{1-6}$ alkylamino group, (20) a $C_{1-6}$ acyl group, (21) a benzoyl group, (22) a 5- to 6-membered heterocyclic group containing, besides carbon atoms, 1 to 3 hetero-atoms selected from oxygen atom, sulfur atom and nitrogen atom which may have 1 to 4 substituents selected from the class consisting of (a) a halogen atom, (b) a $C_{1-6}$ alkyl group and (c) a phenoxy group substituted with 1 to 3 halogen atoms, (23) a $C_{1-6}$ alkyl group substituted with 1 to 3 halogen atoms, (24) a $C_{1-6}$ alkyl group and (25) a $C_{3-8}$ cycloalkyl group;

$R^2$ is a hydrogen atom or an optionally substituted hydrocarbon group selected from the class consisting of (i) a $C_{1-6}$ alkyl group, (ii) a $C_{3-8}$ cycloalkyl group, (iii) a $C_{2-6}$ alkenyl group, (iv) a $C_{2-6}$ alkynyl group, (v) a $C_{3-8}$ cycloalkenyl group, (vi) a $C_{6-10}$ aryl group and (vii) a $C_{7-12}$ aralkyl group, each of said hydrocarbon group being unsubstituted or substituted by 1 to 4 substituents selected from the class consisting of (1) a nitro group, (2) a hydroxy group, (3) an oxo group, (4) a thioxo group, (5) a cyano group, (6) a carbamoyl group, (7) a carboxyl group, (8) a $C_{1-6}$ alkoxy-carbonyl group, (9) a halogen atom, (10) a $C_{1-6}$ alkoxy group, (11) aphenoxy group, (12) a phenoxy group substituted with 1 to 3 halogen atoms, (13) a $C_{1-6}$ alkylthio group, (14) a phenylthio group, (15) a $C_{1-6}$ alkylsulfinyl group, (16) a $C_{1-6}$ alkylsulfonyl group, (17) an amino group, (18) a $C_{1-6}$ alkanoylamino group, (19) a mono- or di-$C_{1-6}$ alkylamino group, (20) a $C_{1-6}$ acyl group, (21) a benzoyl group, (22) a 5- to 6-membered heterocyclic group containing, besides carbon atoms, 1 to 3 hetero-atoms selected from oxygen atom, sulfur atom and nitrogen atom which may have 1 to 4 substituents selected from the class consisting of (a) a halogen atom, (b) a $C_{1-6}$ alkyl group and (c) a phenoxy group substituted with 1 to 3 halogen atoms, (23) a $C_{1-6}$ alkyl group substituted with 1 to 3 halogen atoms, (24) a $C_{1-6}$ alkyl group and (25) a $C_{3-8}$ cycloalkyl group;

$R^3$ is a group of the formula:

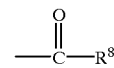

wherein $R^8$ is (A) a hydroxy group, (B) a $C_{1-6}$ alkoxy group optionally substituted with 1 to 3 substituents selected from the class consisting of (1) a hydroxy group, (2) an amino group, (3) a mono-$C_{1-6}$ alkylamino group, (4) a di-$C_{1-6}$ alkylaminogroup, (5) a piperidino group, (6) a morpholino group, (7) a halogen atom, (8) a $C_{1-6}$alkoxy group, (9) a $C_{1-6}$ alkylthio group, (10) a $C_{1-6}$ alkoxy-carbonyl group, (11) a propylidene group, (12) a 3-phthalidylidene group and (13) a 5-methyl-2-oxo-1,3-dioxolan-4-yl group, (C) a group of the formula: —OCH($R^{11}$)OCOR$^{12}$ in which $R^{11}$ is (1) a hydrogen atom, (2) a straight-chain or branched $C_{1-6}$ alkyl group or (3) a $C_{5-7}$ cycloalkyl group, and $R^{12}$ is (1) a straight-chain or branched $C_{1-6}$ alkyl group, (2) a $C_{2-8}$ alkenyl group, (3) a $C_{5-7}$ cycloalkyl group, (4) a $C_{1-3}$ alkyl group substituted with $C_{5-7}$ cycloalkyl or $C_{6-10}$ aryl, said aryl being optionally substituted with 1 to 3 substituents selected from the class consisting of a halogen atom, a nitro group and a $C_{1-6}$ alkyl group, (5) a $C_{2-3}$ alkenyl group substituted with $C_{5-7}$ cycloalkyl or $C_{6-10}$ aryl, said aryl being optionally substituted with 1 to 3 substituents selected from the class consisting of a halogen atom, a nitro group and a $C_{1-6}$ alkyl group, (6) a $C_{6-10}$ aryl group, said aryl being optionally substituted with 1 to 3 substituents selected from the class consisting of a halogen atom, a nitro group and a $C_{1-6}$ alkyl group, (7) a straight-chain or branched $C_{1-6}$ alkoxy group, (8) a straight-chain or branched $C_{2-8}$ alkenyloxy group, (9) a $C_{5-7}$ cycloalkyloxy group, (10) a $C_{1-3}$ alkoxy group substituted with $C_{5-7}$ cycloalkyl or $C_{6-10}$ aryl, said aryl being optionally substituted with 1 to 3 substituents selected from the class consisting of a halogen atom, a nitro group and a $C_{1-6}$ alkyl group, (11) a $C_{2-3}$ alkenyloxy group substituted with $C_{5-7}$ cycloalkyl or $C_{6-10}$ aryl, said aryl being optionally substituted with 1 to 3 substituents selected from the class consisting of a halogen atom, a nitro group and a $C_{1-6}$ alkyl group, or (12) a $C_{6-10}$ aryloxy group, said aryl being optionally substituted with 1 to 3 substituents selected from the class consisting of a halogen atom, a nitro group and a $C_{1-6}$ alkyl group, (D) a $C_{2-8}$ alkenyloxy group, (E) a $C_{7-12}$ aralkyloxy group, or (F) a group of the formula: —NR$^9$R$^{10}$ wherein R$^9$ and R$^{10}$ are the same or different (F-1) a hydrogen atom, (F-2) a $C_{1-6}$ alkyl group, (F-3) a $C_{2-8}$ alkenyl group, or (F-4) a $C_{7-12}$ aralkyl group, the aryl group of which is unsubstituted or substituted with one or two substituents selected from the class consisting of (1) a nitro group, (2) a halogen atom, (3) a $C_{1-6}$ alkyl group and (4) a $C_{1-6}$ alkoxy group; and D is a $C_{1-6}$ alkyl group substituted with a group of the formula:

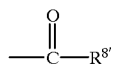

wherein $R^{8'}$ is (A) a hydroxy group, (B) a $C_{1-6}$ alkoxy group optionally substituted with 1 to 3 substituents selected from the class consisting of (1) a hydroxy group, (2) an amino group, (3) a mono-$C_{1-6}$alkylamino group, (4) a di-$C_{1-6}$ alkylamino group, (5) a piperidino group, (6) a morpholino group, (7) ahalogen atom, (8) a $C_{1-6}$ alkoxy group, (9) a $C_{1-6}$ alkylthio group, (10) a $C_{1-6}$ alkoxy-carbonyl group, (11) a propylidene group, (12) a 3-phthalidylidene group and (13) a 5-methyl-2-oxo-1,3-dioxolan-4-yl group, (C) a group of the formula: $-OCH(R^{11})OCOR^{12}$ in which $R^{11}$ is (1) a hydrogen atom, (2) a straight-chain or branched $C_{1-6}$ alkyl group or (3) a $C_{5-7}$ cycloalkyl group, and $R^{12}$ is (1) a straight-chain or branched $C_{1-6}$ alkyl group, (2) a $C_{2-8}$ alkenyl group, (3) a $C_{5-7}$ cycloalkyl group, (4) a $C_{1-3}$ alkyl group substituted with $C_{5-7}$ cycloalkyl or $C_{6-10}$ aryl, said aryl being optionally substituted with 1 to 3 substituents selected from the class consisting of a halogen atom, a nitro group and a $C_{1-6}$ alkyl group, (5) a $C_{2-3}$ alkenyl group substituted with $C_{5-7}$ cycloalkyl or $C_{6-10}$ aryl, said aryl being optionally substituted with 1 to 3 substituents selected from the class consisting of a halogen atom, a nitro group and a $C_{1-5}$ alkyl group, (6) a $C_{6-10}$ aryl group, said aryl being optionally substituted with 1 to 3 substituents selected from the class consisting of a halogen atom, a nitro group and a $C_{1-6}$ alkyl group, (7) a straight-chain or branched $C_{1-6}$ alkoxy group, (8) a straight-chain or branched $C_{2-8}$ alkenyloxy group, (9) a $C_{5-7}$ cycloalkyloxy group, (10) a $C_{1-3}$ alkoxy group substituted with $C_{5-7}$ cycloalkyl or $C_{6-10}$ aryl, said aryl being optionally substituted with 1 to 3 substituents selected from the class consisting of a halogen atom, a nitro group and a $C_{1-6}$ alkyl group, (11) a $C_{2-3}$ alkenyloxy group substituted with $C_{5-7}$ cycloalkyl or $C_{6-10}$ aryl, said aryl being optionally substituted with 1 to 3 substituents selected from the class consisting of a halogen atom, a nitro group and a $C_{1-6}$ alkyl group, or (12) a $C_{6-10}$ aryloxy group, said aryl being optionally substituted with 1 to 3 substituents selected from the class consisting of a halogen atom, a nitro group and a $C_{1-6}$ alkyl group, (D) a $C_{2-8}$ alkenyloxy group, or (E) a $C_{7-12}$ aralkyloxy group.

3. A compound according to claim 1, wherein the ring A is a basic 6-membered heterocyclic group which may be substituted and which contains 1 to 2 nitrogen atoms.

4. A compound according to claim 5, wherein the basic 6-membered heterocyclic group is pyridyl, pyrimidinyl or piperidyl.

5. A compound according to claim 3, wherein the basic 6-membered heterocyclic group is piperidyl.

6. A compound according to claim 3, wherein the basic 6-membered heterocyclic group is pyridyl.

7. A compound according to claim 2, wherein the ring $A^1$ is pyridyl.

8. A compound according to claim 1, wherein the ring B is a divalent 6-membered nitrogen containing heterocyclic group which contains 1 or 2 nitrogen atoms and which may be substituted or a phenylene group which may be substituted.

9. A compound according to claim 1, wherein the ring B is phenylene, piperidinedjyl or piperazinediyl, each of which may be substituted.

10. A compound according to claim 1, wherein the ring B is phenylene which may be substituted.

11. A compound according to claim 1, wherein the ring B is piperazinediyl which may be substituted.

12. A compound according to claim 1, wherein $R^1$ is a hydrogen atom, an optionally substituted hydroxy group, an optionally substituted lower alkyl group or an optionally substituted amino group.

13. A compound according to claim 1, wherein $R^1$ is a hydroxy group optionally substituted with a $C_{1-6}$ alkyl-carbonyl group.

14. A compound according to claim 1, wherein $R^1$ is an optionally substituted amino group selected from the class consisting of (1) an amino group optionally substituted with a $C_{1-6}$ acyl group, (2) a mono-$C_{1-6}$ alkylamino group, (3) a di-$C_{1-6}$ alkylamino group, (4) a $C_{1-6}$ alkoxy-carbonylamino group, (5) a $C_{1-6}$ alkylthio-carbonylamino group, (6) a $C_{7-12}$ aralkylamino group which may have 1 to 3 substituents selected from the class consisting of a halogen atom, a $C_{1-6}$ alkyl group and a $C_{1-5}$ alkoxy group, (7) a benzoylamino group which may have 1 to 3 substituents selected from the class consisting of a halogen atom, a $C_{1-6}$ alkyl group and a $C_{1-6}$ alkoxy group, (8) a benzene-sulfonylamino group which may have 1 to 3 substituents selected from the class consisting of a halogen atom, a $C_{1-6}$ alkyl group and a $C_{1-6}$ alkoxy group, and (9) a $C_{1-6}$ alkoxy-carbonylamino group which may be substituted with $C_{1-6}$ alkanoyloxy, benzoyloxy, $C_{1-6}$ alkoxy-carbonyloxy, $C_{3-8}$ cycloalkyl-oxycarbonyloxy, $C_{3-8}$ cycloalkyl-carbonyloxy, 6-membered aromatic heterocyclic group-carbonyloxy or 5-methyl-2-oxo-1,3-dioxolan-4-yl.

15. A compound according to claim 1, wherein $R^1$ is an optionally substituted hydrocarbon group which may be bound through a carbonyl group, a thio group, a sulfinyl group or a sulfonyl group, being selected from the class consisting of (1) a $C_{1-6}$ alkyl-carbonyl group, (2) a $C_{1-6}$ alkylthio group, (3) a $C_{1-6}$ alkylsulf inyl group, (4) a $C_{1-6}$ alkylsulfonyl group, (5) a benzoyl group which may have 1 to 3 substituents selected from the class consisting of a halogen atom, a $C_{1-6}$ alkyl group and a $C_{1-6}$ alkoxy group, (6) a phenylthio group which may have 1 to 3 substituents selected from the class consisting of a halogen atom, a $C_{1-6}$ alkyl group, a $C_{1-6}$ alkoxy group, (7) a phenylsulfinyl group which may have 1 to 3 substituents selected from the class consisting of a halogen atom, a $C_{1-6}$ alkyl group and a $C_{1-6}$ alkoxy group, (8) a phenylsulfonyl group which may have 1 to 3 substituents selected from the class consisting of a halogen atom, a $C_{1-6}$ alkyl group and a $C_{1-6}$ alkoxy group, (9) a $C_{7-12}$ aralkyl-carbonyl group which may have 1 to 3 substituents selected from the class consisting of a halogen atom, a $C_{1-6}$ alkyl group and a $C_{1-6}$ alkoxy group, (10) a $C_{7-12}$ aralkylthio group which may have 1 to 3 substituents selected from the class consisting of a halogen atom, a $C_{1-6}$ alkyl group and a $C_{1-6}$ alkoxy group, (11) a $C_{7-12}$ aralkyl-sulfinyl group which may have 1 to 3 substituents selected from the class consisting of a halogen atom, a $C_{1-6}$ alkyl group and a $C_{1-6}$ alkoxy group, (12) a $C_{7-12}$ aralkyl-sulfonyl group which may have 1 to 3 substituents selected from the class consisting of a halogen atom, a $C_{1-6}$ alkyl group and a $C_{1-6}$ alkoxy group, and (13) a $C_{1-6}$ alkyl group optionally substituted with a $C_{1-6}$ aryl group which may have 1 to 3 substituents selected from the class consisting of a halogen atom, a $C_{1-6}$ alkyl group and a $C_{1-6}$ alkoxy group.

16. A compound according to claim 1, wherein $R^2$ is a hydrogen atom.

17. A compound according to claim 1, wherein $R^3$ is a carboxyl group or a $C_{1-6}$ alkoxy-carbonyl group.

18. A compound according to claim 1, wherein $R^3$ is methoxycarbonyl, ethoxycarbonyl, t-butoxycarbonyl, propoxycarbonyl, pivaloyloxymethoxycarbonyl, 1-(cyclohexyloxycarbonyloxy)ethoxycarbonyl, 5-methyl-2-oxo-1,3-dioxolan-4-ylmethoxycarbonyl, acetoxymethyloxycarbonyl, propionyloxymethoxycarbonyl, n-butyryloxymethoxycarbonyl, isobutyryloxymethoxycarbonyl, 1-(ethoxycarbonyloxy)ethoxycarbonyl, 1-(acetyloxy)ethyloxycarbonyl, 1-(isobutyryloxy)ethoxycarbonyl, cyclohexylcarbonyloxymethoxycarbonyl, benzoyloxymethoxycarbonyl, cinnamyloxycarbonyl, cyclopentylcarbonyloxy-methoxycarbonyl, N,N-dimethylaminocarbonyl, 2-(iso-butyryloxycarbonyl)-2-propylideneethoxycarbonyl or 3-(phthalidylidene)ethoxycarbonyl.

19. A compound according to claim 1, wherein D is a $C_{1-6}$ alkoxy-carbonyl-$C_{1-6}$ alkyl group.

20. A compound according to claim 1, wherein the ring A is pyridyl, pyrimidinyl or piperidyl; the ring B is phenylene, piperidinediyl or piperazinediyl; Y is a methylene group; $R^1$ is (A) a hydrogen atom, (B) a hydroxy group optionally substituted with a $C_{1-6}$ alkyl-carbonyl group, (C) an amino group optionally substituted with one or two substituents selected from the class consisting of (1) a formyl group, (2) a $C_{26}$ alkanoyl group, (3) a $C_{1-6}$ alkyl group, (4) a $C_{1-6}$ alkoxy-carbonyl group, (5) a $C_{1-6}$ alkylthio-carbonyl group, (6) a $C_{7-12}$ aralkyl group which may have 1 to 3 substituents selected from the class consisting of a halogen atom, a $C_{1-6}$ alkyl group and a $C_{1-6}$ alkoxy group, (7) a benzoyl group which may have 1 to 3 substituents selected from the class consisting of a halogen atom, a $C_{1-6}$ alkyl group and a $C_{1-6}$ alkoxy group, (8) a benzenesulfonyl group which may have 1 to 3 substituents selected from the class consisting of a halogen atom, a $C_{1-6}$ alkyl group and a $C_{1-6}$ alkoxy group, and (9) a $C_{1-6}$ alkoxy-carbonyl group which may be substituted with $C_{1-6}$ alkanoyloxy, benzoyloxy, $C_{1-6}$ alkoxy-carbonyloxy, $C_{3-8}$ cycloalkyloxy-carbonyloxy, $C_{3-8}$ cycloalkyl-carbonyloxy, pyridyl-carbonyloxy or 5-methyl-2-oxo-1,3-dioxolan-4-yl, or (D) a $C_{1-6}$ alkyl group optionally substituted with a $C_{6-10}$ aryl group which may have 1 to 3 substituents selected from the class consisting of a halogen atom, a $C_{1-6}$ alkyl group and a $C_{1-6}$ alkoxy group; $R^2$ is a hydrogen atom; $R^3$ is a carboxyl group or a $C_{1-6}$ alkoxy-carbonyl group; and D is a $C_{1-6}$ alkoxy-carbonyl-$C_{1-6}$ alkyl group.

21. A compound of claim 1, which is (S,S)-[4-[2-(4-methoxybenzenesulfonylamino)-4-oxo-(4-pyridin-4-yl-piperazin-1-yl)butyryl]-3-methoxycarbonylmethyl-2-oxo-piperazin-1-yl]acetic acid, (S,S)-[4-[2-(4-methoxy-benzylamino)-4-oxo-(4-pyridin-4-ylpiperazin-1-yl)-butyryl]-3-methoxycarbonylmethyl-2-oxopiperazin-1-yl]-acetic acid, or a pharmaceutically acceptable salt thereof.

22. A pharmaceutical composition which comprises a compound or a salt thereof according to any one of claims 1–3.

23. A pharmaceutical composition for inhibiting cell-adhesion which comprises a compound or a salt thereof according to claim 1.

24. A pharmaceutical composition for treating or preventing angina pectoris, which comprises a compound or a salt thereof according to claim 1 in admixture with a pharmaceutically acceptable carrier or excipient.

25. A pharmaceutical composition for treating or preventing unstable angina, which comprises a compound or a salt thereof according to claim 1 in admixture with a pharmaceutically acceptable carrier or excipient.

26. A pharmaceutical composition for treating or preventing ischemic complication, reobstruction or restenosis after percutaneous transluminal coronary angioplasty or coronary thrombolytic therapy, which comprises a compound or a salt thereof according to claim 1, in admixture with a pharmaceutically acceptable carrier or excipient.

27. A method of using a compound or a salt thereof according to any claim 1 for manufacturing a pharmaceutical omposition.

28. A method of using a compound or a salt thereof according to claim 1 for manufacturing a pharmaceutical composition for inhibiting cell-adhesion.

29. A method of using a compound or a salt thereof according to claim 1 for manufacturing a pharmaceutical composition for treating or preventing angina pectoris.

30. A method of using a compound or a salt thereof according to claim 1 for manufacturing a pharmaceutical composition for treating or preventing unstable angina.

31. A method of using a compound or a salt thereof according to claim 1 for manufacturing a pharmaceutical composition for treating or preventing ischemic complication, reobstruction or restenosis after percutaneous transluminal coronary angioplasty or coronary thrombolytic therapy.

32. A method for inhibiting cell-adhesion in a mammal which comprises administering an effective amount of a compound or a salt thereof according to of claim 1 to said mammal.

33. A method for preventing or treating angina pectoris, in a mammal which comprises administering an effective amount of a compound or a salt thereof according to any one of claim 1 to said mammal.

34. A method for preventing or treating unstable angina in a mammal which comprises administering an effective amount of a compound or a salt thereof according to claim 1 to said mammal.

35. A method for preventing or treating ischemic complication, reobstruction or restenosis after percutaneous transluminal coronary angioplasty or coronary thrombolytic therapy in a mammal which comprises administering an effective amount of a compound or a salt thereof according to claim 1 to said mammal.

36. A method for producing a compound of the formula:

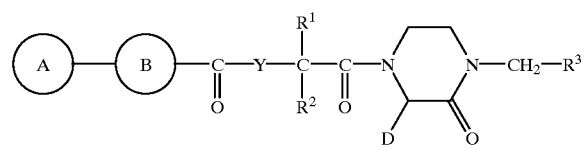

wherein the ring A is a basic 5- to 7-membered heterocyclic group which may be substituted; the ring B is a divalent 5- to 7-membered nitrogen containing heterocyclic group which may be substituted or a divalent 5- to 7-membered cyclic hydrocarbon group which may be substituted; Y is an optionally substituted methylene group; $R^1$ is a hydrogen atom, an optionally substituted hydroxy group, an optionally substituted amino group or an optionally substituted hydrocarbon group which may be bound through a carbonyl group, a thio group, a sulfinyl group or a sulfonyl group; $R^2$ is a hydrogen atom or an optionally substituted hydrocarbon group; $R^3$ is an optionally esterified or amidated carboxyl group; and D is a lower alkyl group substituted with an optionally esterified carboxyl group; or a salt thereof, which comprises subjecting a compound (II) of the formula:

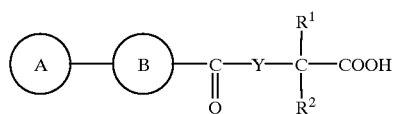

(II)

wherein each symbol is of the same meaning as defined above, or a salt thereof and a compound (III) of the formula:

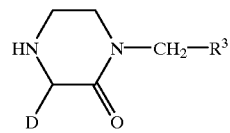

(III)

wherein each symbol is of the same meaning as defined above, or a salt thereof to condensation reaction.

37. A method for producing a compound of the formula:

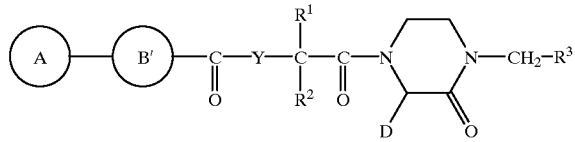

wherein the ring A is a basic 5- to 7-membered heterocyclic group which may be substituted; the ring B' is an optionally substituted piperazinediyl group; Y is an optionally substituted methylene group; $R^1$ is a hydrogen atom, an optionally substituted hydroxy group, an optionally substituted amino group or an optionally substituted hydrocarbon group which may be bound through a carbonyl group, a thio group, a sulfinyl group or a sulfonyl group; $R^2$ is a hydrogen atom or an optionally substituted hydrocarbon group; $R^3$ is an optionally esterified or amidated carboxyl group; and D is a lower alkyl group substituted with an optionally esterified carboxyl group; or a salt thereof, which comprises subjecting a compound (VI) of the formula:

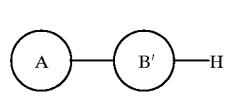

(VI)

wherein B' is an optionally substituted piperazinediyl group and the other symbols are of the same meaning as defined above, or a salt thereof and a compound (VII) of the formula:

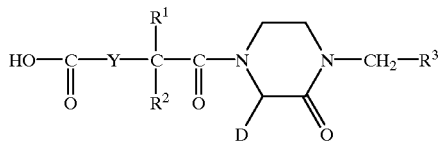

(VII)

wherein each symbol is of the same meaning as defined above, or a salt thereof to condensation reaction.

38. A compound of claim 1, which is (R,S)-(4-[2-Amino-4-oxo-4-(4-pyridin-4-ylpiperazin-1-yl)butyryl]-3-methoxycarbonylmethyl-2-oxopiperazin-1-yl)acetic acid trifluoroacetic acid salt.

* * * * *